(12) United States Patent
Van Criekinge et al.

(10) Patent No.: US 7,507,536 B2
(45) Date of Patent: Mar. 24, 2009

(54) METHYLATION MARKERS FOR DIAGNOSIS AND TREATMENT OF OVARIAN CANCER

(75) Inventors: Wim Van Criekinge, Sart-Tilman (BE); Josef Straub, Sart-Tilman (BE); Nathalie Sieben, Maastricht (NL)

(73) Assignees: The Johns Hopkins University, Baltimore, MD (US); OncoMethylome Sciences, S.A., Sart-Tilman (Liege) (BE)

( * ) Notice: Subject to any disclaimer, the term of this patent is extended or adjusted under 35 U.S.C. 154(b) by 0 days.

(21) Appl. No.: 11/543,986

(22) Filed: Oct. 6, 2006

(65) Prior Publication Data

US 2007/0087365 A1    Apr. 19, 2007

Related U.S. Application Data

(60) Provisional application No. 60/724,265, filed on Oct. 7, 2005.

(51) Int. Cl.
*C12Q 1/68* (2006.01)
(52) U.S. Cl. .......................................... 435/6
(58) Field of Classification Search ................ 435/6
See application file for complete search history.

(56) References Cited

OTHER PUBLICATIONS

Tockman et al (Cancer Res., 1992, 52:2711s-2718s).*

* cited by examiner

*Primary Examiner*—Sean E Aeder
(74) *Attorney, Agent, or Firm*—Banner & Witcoff, Ltd.

(57) ABSTRACT

Twenty-three markers are provided which are epigenetically silenced in ovarian cancers. The markers can be used diagnostically, prognostically, therapeutically, and for selecting treatments that are well tailored for an individual patient. Restoration of expression of silenced genes can be useful therapeutically, for example, if the silenced gene is a tumor-suppressor gene. Restoration can be accomplished by supplying non-methylated copies of the silenced genes or polynucleotides encoding their encoded products. Alternatively, restoration can be accomplished using chemical demethylating agents or methylation inhibitors. Kits for testing for epigenetic silencing can be used in the context of diagnostics, prognostics, or for selecting "personalized medicine" treatments.

17 Claims, No Drawings

SEQUENCE LISTING

<160> NUMBER OF SEQ ID NOS: 172

<210> SEQ ID NO 1
<211> LENGTH: 2984
<212> TYPE: DNA
<213> ORGANISM: Homo sapiens

<400> SEQUENCE: 1

```
ggaaattcaa acgtgtttgc ggaaaggagt ttgggttcca tcttttcatt tccccagcgc      60
agctttctgt agaaatggaa tccgaggatt taagtggcag agaattgaca attgattcca     120
taatgaacaa agtgagagac attaaaaata agtttaaaaa tgaagacctt actgatgaac     180
taagcttgaa taaaatttct gctgatacta cagataactc gggaactgtt aaccaaatta     240
tgatgatggc aaacaaccca gaggactggt tgagtttgtt gctcaaacta gagaaaaaca     300
gtgttccgct aagtgatgct cttttaaata aattgattgg tcgttacagt caagcaattg     360
aagcgcttcc cccagataaa tatggccaaa atgagagttt tgctagaatt caagtgagat     420
ttgctgaatt aaaagctatt caagagccag atgatgcacg tgactacttt caaatggcca     480
gagcaaactg caagaaattt gcttttgttc atatatcttt tgcacaattt gaactgtcac     540
aaggtaatgt caaaaaaagt aaacaacttc ttcaaaaagc tgtagaacgt ggagcagtac     600
cactagaaat gctggaaatt gccctgcgga atttaaacct ccaaaaaaag cagctgcttt     660
cagaggagga aaagaagaat ttatcagcat ctacggtatt aactgcccaa gaatcatttt     720
ccggttcact tgggcattta cagaatagga acaacagttg tgattccaga ggacagacta     780
ctaaagccag ttttttatat ggagagaaca tgccaccaca agatgcagaa ataggttacc     840
ggaattcatt gagacaaact aacaaaacta aacagtcatg cccatttgga agagtcccag     900
ttaaccttct aaatagccca gattgtgatg tgaagacaga tgattcagtt gtaccttgtt     960
ttatgaaaag acaaacctct agatcagaat gccgagattt ggttgtgcct ggatctaaac    1020
caagtggaaa tgattcctgt gaattaagaa atttaaagtc tgttcaaaat agtcatttca    1080
aggaacctct ggtgtcagat gaaaagagtt ctgaacttat tattactgat tcaataaccc    1140
tgaagaataa aacggaatca agtcttctag ctaaattaga agaaactaaa gagtatcaag    1200
aaccagaggt tccagagagt aaccagaaac agtggcaatc aagagaaaag tcagagtgta    1260
ttaaccagaa tcctgctgca tcttcaaatc actggcagat tccggagtta gcccgaaaag    1320
ttaatacaga gcagaaacat accacttttg agcaacctgt cttttcagtt tcaaaacagt    1380
caccaccaat atcaacatct aaatggtttg acccaaaatc tatttgtaag acaccaagca    1440
gcaatacctt ggatgattac atgagctgtt ttagaactcc agttgtaaag aatgactttc    1500
cacctgcttg tcagttgtca acaccttatg ccaacctgc ctgtttccag cagcaacagc    1560
atcaaatact tgccactcca cttcaaaatt tacaggtttt agcatcttct tcagcaaatg    1620
aatgcatttc ggttaaagga agaatttatt ccattttaaa gcagatagga agtggaggtt    1680
caagcaaggt atttcaggtg ttaaatgaaa agaaacagat atatgctata aaatatgtga    1740
acttagaaga agcagataac caaactcttg atagttaccg gaacgaaata gcttatttga    1800
ataaactaca caacacagt gataagatca tccgacttta tgattatgaa atcacggacc    1860
agtacatcta catggtaatg gagtgtggaa atattgatct taatagttgg cttaaaagaa    1920
aaaaatccat tgatccatgg gaacgcaaga gttactggaa aaatatgtta gaggcagttc    1980
acacaatcca tcaacatggc attgttcaca gtgatcttaa accagctaac tttctgatag    2040
ttgatgggaat gctaaagcta attgattttg ggattgcaaa ccaaatgcaa ccagatacaa    2100
caagtgttgt taaagattct caggttggca cagttaatta tatgccacca gaagcaatca    2160
aagatatgtc ttcctccaga gagaatggga atctaagtc aaagataagc cccaaaagtg    2220
atgtttggtc cttaggatgt atttttgtact atatgactta cggaaaaaca ccatttcagc    2280
```

-continued

```
agataattaa tcagatttct aaattacatg ccataattga tcctaatcat gaaattgaat    2340
ttcccgatat tccagagaaa gatcttcaag atgtgttaaa gtgttgttta aaaagggacc    2400
caaaacagag gatatccatt cctgagctcc tggctcatcc ctatgttcaa attcaaactc    2460
atccagttaa ccaaatggcc aagggaacca ctgaagaaat gaaatatgtt ctgggccaac    2520
ttgttggtct gaattctcct aactccattt tgaaagctgc taaaacttta tatgaacact    2580
atagtggtgg tgaaagtcat aattcttcat cctccaagac ttttgaaaaa aaaaggggaa    2640
aaaaatgatt tgcagttatt cgtaatgtca ataccacct ataaaatata ttggactgtt     2700
atactcttga atccctgtgg aaatctacat ttgaagacaa catcactctg aagtgttatc    2760
agcaaaaaaa attcagtaga ttatctttaa aagaaaactg taaaaatagc aaccacttat    2820
ggtactgtat atattgtaga cttgtttttct ctgttttatg ctcttgtgta atctacttga   2880 catcattta ctcttggaat agtgggtgga tagcaagtat attctaaaaa actttgtaaa     2940
taaagttttg tggctaaaat gacactaaaa aaaaaaaaa aaaa                      2984
```

<210> SEQ ID NO 2
<211> LENGTH: 857
<212> TYPE: PRT
<213> ORGANISM: Homo sapiens

<400> SEQUENCE: 2

```
Met Glu Ser Glu Asp Leu Ser Gly Arg Glu Leu Thr Ile Asp Ser Ile
 1               5                  10                  15

Met Asn Lys Val Arg Asp Ile Lys Asn Lys Phe Lys Asn Glu Asp Leu
            20                  25                  30

Thr Asp Glu Leu Ser Leu Asn Lys Ile Ser Ala Asp Thr Thr Asp Asn
        35                  40                  45

Ser Gly Thr Val Asn Gln Ile Met Met Met Ala Asn Asn Pro Glu Asp
    50                  55                  60

Trp Leu Ser Leu Leu Leu Lys Leu Glu Lys Asn Ser Val Pro Leu Ser
65                  70                  75                  80

Asp Ala Leu Leu Asn Lys Leu Ile Gly Arg Tyr Ser Gln Ala Ile Glu
                85                  90                  95

Ala Leu Pro Pro Asp Lys Tyr Gly Gln Asn Glu Ser Phe Ala Arg Ile
            100                 105                 110

Gln Val Arg Phe Ala Glu Leu Lys Ala Ile Gln Glu Pro Asp Asp Ala
        115                 120                 125

Arg Asp Tyr Phe Gln Met Ala Arg Ala Asn Cys Lys Lys Phe Ala Phe
    130                 135                 140

Val His Ile Ser Phe Ala Gln Phe Glu Leu Ser Gln Gly Asn Val Lys
145                 150                 155                 160

Lys Ser Lys Gln Leu Leu Gln Lys Ala Val Glu Arg Gly Ala Val Pro
                165                 170                 175

Leu Glu Met Leu Glu Ile Ala Leu Arg Asn Leu Asn Leu Gln Lys Lys
            180                 185                 190

Gln Leu Leu Ser Glu Glu Lys Lys Asn Leu Ser Ala Ser Thr Val
        195                 200                 205

Leu Thr Ala Gln Glu Ser Phe Ser Gly Ser Leu Gly His Leu Gln Asn
    210                 215                 220

Arg Asn Asn Ser Cys Asp Ser Arg Gly Gln Thr Thr Lys Ala Arg Phe
225                 230                 235                 240

Leu Tyr Gly Glu Asn Met Pro Pro Gln Asp Ala Glu Ile Gly Tyr Arg
                245                 250                 255
```

-continued

Asn Ser Leu Arg Gln Thr Asn Lys Thr Lys Gln Ser Cys Pro Phe Gly
            260                 265                 270

Arg Val Pro Val Asn Leu Leu Asn Ser Pro Asp Cys Asp Val Lys Thr
        275                 280                 285

Asp Asp Ser Val Val Pro Cys Phe Met Lys Arg Gln Thr Ser Arg Ser
    290                 295                 300

Glu Cys Arg Asp Leu Val Val Pro Gly Ser Lys Pro Ser Gly Asn Asp
305                 310                 315                 320

Ser Cys Glu Leu Arg Asn Leu Lys Ser Val Gln Asn Ser His Phe Lys
                325                 330                 335

Glu Pro Leu Val Ser Asp Glu Lys Ser Ser Glu Leu Ile Ile Thr Asp
            340                 345                 350

Ser Ile Thr Leu Lys Asn Lys Thr Glu Ser Ser Leu Leu Ala Lys Leu
        355                 360                 365

Glu Glu Thr Lys Glu Tyr Gln Glu Pro Glu Val Pro Glu Ser Asn Gln
    370                 375                 380

Lys Gln Trp Gln Ser Lys Arg Lys Ser Glu Cys Ile Asn Gln Asn Pro
385                 390                 395                 400

Ala Ala Ser Ser Asn His Trp Gln Ile Pro Glu Leu Ala Arg Lys Val
                405                 410                 415

Asn Thr Glu Gln Lys His Thr Thr Phe Glu Gln Pro Val Phe Ser Val
            420                 425                 430

Ser Lys Gln Ser Pro Pro Ile Ser Thr Ser Lys Trp Phe Asp Pro Lys
        435                 440                 445

Ser Ile Cys Lys Thr Pro Ser Ser Asn Thr Leu Asp Asp Tyr Met Ser
    450                 455                 460

Cys Phe Arg Thr Pro Val Val Lys Asn Asp Phe Pro Pro Ala Cys Gln
465                 470                 475                 480

Leu Ser Thr Pro Tyr Gly Gln Pro Ala Cys Phe Gln Gln Gln His
                485                 490                 495

Gln Ile Leu Ala Thr Pro Leu Gln Asn Leu Gln Val Leu Ala Ser Ser
            500                 505                 510

Ser Ala Asn Glu Cys Ile Ser Val Lys Gly Arg Ile Tyr Ser Ile Leu
        515                 520                 525

Lys Gln Ile Gly Ser Gly Gly Ser Ser Lys Val Phe Gln Val Leu Asn
    530                 535                 540

Glu Lys Lys Gln Ile Tyr Ala Ile Lys Tyr Val Asn Leu Glu Glu Ala
545                 550                 555                 560

Asp Asn Gln Thr Leu Asp Ser Tyr Arg Asn Glu Ile Ala Tyr Leu Asn
                565                 570                 575

Lys Leu Gln Gln His Ser Asp Lys Ile Ile Arg Leu Tyr Asp Tyr Glu
            580                 585                 590

Ile Thr Asp Gln Tyr Ile Tyr Met Val Met Glu Cys Gly Asn Ile Asp
        595                 600                 605

Leu Asn Ser Trp Leu Lys Lys Lys Ser Ile Asp Pro Trp Glu Arg
    610                 615                 620

Lys Ser Tyr Trp Lys Asn Met Leu Glu Ala Val His Thr Ile His Gln
625                 630                 635                 640

His Gly Ile Val His Ser Asp Leu Lys Pro Ala Asn Phe Leu Ile Val
                645                 650                 655

Asp Gly Met Leu Lys Leu Ile Asp Phe Gly Ile Ala Asn Gln Met Gln
            660                 665                 670

```
Pro Asp Thr Thr Ser Val Val Lys Asp Ser Gln Val Gly Thr Val Asn
            675                 680                 685
Tyr Met Pro Pro Glu Ala Ile Lys Asp Met Ser Ser Ser Arg Glu Asn
        690                 695                 700
Gly Lys Ser Lys Ser Lys Ile Ser Pro Lys Ser Asp Val Trp Ser Leu
705                 710                 715                 720
Gly Cys Ile Leu Tyr Tyr Met Thr Tyr Gly Lys Thr Pro Phe Gln Gln
                725                 730                 735
Ile Ile Asn Gln Ile Ser Lys Leu His Ala Ile Ile Asp Pro Asn His
            740                 745                 750
Glu Ile Glu Phe Pro Asp Ile Pro Glu Lys Asp Leu Gln Asp Val Leu
        755                 760                 765
Lys Cys Cys Leu Lys Arg Asp Pro Lys Gln Arg Ile Ser Ile Pro Glu
770                 775                 780
Leu Leu Ala His Pro Tyr Val Gln Ile Gln Thr His Pro Val Asn Gln
785                 790                 795                 800
Met Ala Lys Gly Thr Thr Glu Glu Met Lys Tyr Val Leu Gly Gln Leu
                805                 810                 815
Val Gly Leu Asn Ser Pro Asn Ser Ile Leu Lys Ala Ala Lys Thr Leu
            820                 825                 830
Tyr Glu His Tyr Ser Gly Gly Glu Ser His Asn Ser Ser Ser Ser Lys
        835                 840                 845
Thr Phe Glu Lys Lys Arg Gly Lys Lys
    850                 855

<210> SEQ ID NO 3
<211> LENGTH: 1055
<212> TYPE: DNA
<213> ORGANISM: Homo sapiens

<400> SEQUENCE: 3
ggcggagccg cctgggctgc agtcccaccc gggagccggc agggagcgga gctgcggagc      60
cgcctggtct cccgcgtcca tcggtccatt cctgcgtcgt tctgtccttc cgaacgcaca     120
cttcaggagc agccgcgagg gtggcatggc agcgagcaca gacatggctg gctggagga     180
gagcttccgc aagtttgcca tccatggtga ccccaaggcc agtgggcaag agatgaatgg     240
caagaactgg gccaagctgt gcaaggactg caaggtggct gacggaaagt ccgtgacagg     300
gaccgatgtg gacatcgtct ctccaaagt caaggggaag tctgctcggg tcatcaacta     360
tgaggagttc aagaaggccc tggaagagct ggcgaccaag agattcaagg ggaagagcaa     420
ggaggaggcc ttcgatgcca tctgccagct ggtggcaggc aaaagagccag ccaatgtggg     480
cgtcactaaa gcaaaaacag ggggtgctgt agaccggctg acggacacca gcagatacac     540
gggctcccac aaggagcgct tcgatgagag cggcaagggc aagggcattg cgggacggca     600
ggacatcctg gacgacagtg gctacgtgag cgcctacaag aatgcaggca cctacgatgc     660
caaggtgaag aagtgaggct tgggaagacc gccctgccaa gtgcggctgc ccctgccaga     720
ggctcaggcc tgggtctaag gggcacgtgg agcaagagat cctggtcccc tcctgctgg      780
acctgccacc cagagcttcc tgcctagtcc cactgggctg gcccaccagg cctctgaccc     840
aggctgctct gcggcccctt cctcctcctc ttcctgctcc aacttctgtc cacctgggga     900
cagtctgtgc ctgtagcctc atgaccccaa cccagcccca ggcatggcta accctgact     960
gcttgcctca tatttaagct gctgtctctgg ccaagtgcct aattttaacc cagacctcaa    1020
taaagacacc ttttgtacca aaaaaaaaaa aaaaa                                1055
```

<210> SEQ ID NO 4
<211> LENGTH: 176
<212> TYPE: PRT
<213> ORGANISM: Homo sapiens

<400> SEQUENCE: 4

Met Ala Ala Ser Thr Asp Met Ala Gly Leu Glu Glu Ser Phe Arg Lys
 1               5                  10                  15

Phe Ala Ile His Gly Asp Pro Lys Ala Ser Gly Gln Glu Met Asn Gly
                20                  25                  30

Lys Asn Trp Ala Lys Leu Cys Lys Asp Cys Lys Val Ala Asp Gly Lys
            35                  40                  45

Ser Val Thr Gly Thr Asp Val Asp Ile Val Phe Ser Lys Val Lys Gly
        50                  55                  60

Lys Ser Ala Arg Val Ile Asn Tyr Glu Glu Phe Lys Lys Ala Leu Glu
65                  70                  75                  80

Glu Leu Ala Thr Lys Arg Phe Lys Gly Lys Ser Lys Glu Glu Ala Phe
                85                  90                  95

Asp Ala Ile Cys Gln Leu Val Ala Gly Lys Glu Pro Ala Asn Val Gly
                100                 105                 110

Val Thr Lys Ala Lys Thr Gly Gly Ala Val Asp Arg Leu Thr Asp Thr
            115                 120                 125

Ser Arg Tyr Thr Gly Ser His Lys Glu Arg Phe Asp Glu Ser Gly Lys
        130                 135                 140

Gly Lys Gly Ile Ala Gly Arg Gln Asp Ile Leu Asp Asp Ser Gly Tyr
145                 150                 155                 160

Val Ser Ala Tyr Lys Asn Ala Gly Thr Tyr Asp Ala Lys Val Lys Lys
                165                 170                 175

<210> SEQ ID NO 5
<211> LENGTH: 1146
<212> TYPE: DNA
<213> ORGANISM: Homo sapiens

<400> SEQUENCE: 5
ggcggagccg cctgggctgc agtcccaccc gggagccggc agggagcgga gctgcggagc    60
cgcctggtct cccgcgtcca tcggtccatt cctgcgtcgt tctgtccttc cgaacgcaca   120
cttcaggagc agccgcgagg agtgagcact gcacgcagga tccgcccagt gcttgggcca   180
agcaccctgt ggcatccaag ctcccctgga cgttacccctt ggtgaaccaa ggtggcatgg   240
cagcgagcac agacatggct gggctggagg agagcttccg caagtttgcc atccatggtg   300
accccaaggc cagtgggcaa gagatgaatg gcaagaactg gccaagctg tgcaaggact   360 gcaaggtggc tgacggaaag tccgtgacag ggaccgatgt ggacatcgtc ttctccaaag   420 tcaagggaa gtctgctcgg gtcatcaact atgaggagtt caagaaggcc ctggaagagc   480
tggcgaccaa gagattcaag gggaagagca aggaggaggc cttcgatgcc atctgccagc   540
tggtggcagg caaagagcca gccaatgtgg gcgtcactaa agcaaaaaca ggggtgctg   600 tagaccggct gacggacacc agcagataca cgggctccca caaggagcgc ttcgatgaga   660
gcggcaaggg caagggcatt gcgggacggc aggacatcct ggacgacagt ggctacgtga   720
gcgcctacaa gaatgcaggc acctacgatg ccaaggtgaa gaagtgaggc ttgggaagac   780
cgccctgcca gtgcggctg cccctgccag aggctcaggc ctgggtctaa ggggcacgtg   840
gagcaagaga tcctggtccc ctccctgctg gacctgccac ccagagcttc ctgcctagtc   900

-continued

```
ccactgggct ggcccaccag gcctctgacc caggctgctc tgcggcccct tcctcctcct      960
cttcctgctc caacttctgt ccacctgggg acagtctgtg cctgtagcct catgacccca     1020
acccagcccc aggcatggct aacccctgac tgcttgcctc atatttaagc tgctgctctg     1080
gccaagtgcc taattttaac ccagacctca ataaagacac cttttgtacc aaaaaaaaaa     1140
aaaaaa                                                                1146
```

<210> SEQ ID NO 6
<211> LENGTH: 176
<212> TYPE: PRT
<213> ORGANISM: Homo sapiens

<400> SEQUENCE: 6

```
Met Ala Ala Ser Thr Asp Met Ala Gly Leu Glu Glu Ser Phe Arg Lys
 1               5                  10                  15

Phe Ala Ile His Gly Asp Pro Lys Ala Ser Gly Gln Glu Met Asn Gly
            20                  25                  30

Lys Asn Trp Ala Lys Leu Cys Lys Asp Cys Lys Val Ala Asp Gly Lys
        35                  40                  45

Ser Val Thr Gly Thr Asp Val Asp Ile Val Phe Ser Lys Val Lys Gly
    50                  55                  60

Lys Ser Ala Arg Val Ile Asn Tyr Glu Glu Phe Lys Lys Ala Leu Glu
65                  70                  75                  80

Glu Leu Ala Thr Lys Arg Phe Lys Gly Lys Ser Lys Glu Glu Ala Phe
                85                  90                  95

Asp Ala Ile Cys Gln Leu Val Ala Gly Lys Glu Pro Ala Asn Val Gly
            100                 105                 110

Val Thr Lys Ala Lys Thr Gly Gly Ala Val Asp Arg Leu Thr Asp Thr
        115                 120                 125

Ser Arg Tyr Thr Gly Ser His Lys Glu Arg Phe Asp Glu Ser Gly Lys
    130                 135                 140

Gly Lys Gly Ile Ala Gly Arg Gln Asp Ile Leu Asp Asp Ser Gly Tyr
145                 150                 155                 160

Val Ser Ala Tyr Lys Asn Ala Gly Thr Tyr Asp Ala Lys Val Lys Lys
                165                 170                 175
```

<210> SEQ ID NO 7
<211> LENGTH: 3404
<212> TYPE: DNA
<213> ORGANISM: Homo sapiens

<400> SEQUENCE: 7

```
gcagttcaga ccccccaca cccatcaaag agccgctcct cccccccgca ggcgccttcg       60
ccgcctccct cccttccttt cctttccgct cctcttccga cctgtccacc cgggaggaag     120
ggagctggaa aggggcgga aacctctccc ctccaaaaag cacaacaaaa ctgttcagtg      180
cggaggagcc gggttcgccc ctgccggaca gcggggggct tgttccccg cagttgtttc      240
ctgcccattt gacctgtcag ctgctgggga aacgctgctg ttgaccttg gttgaactgc      300
taaggcgatt ttgctgattt ttctttcttt ttccgcgagg gctgtctttt gctcctccaa     360
atgagcccag tcccctccc ttctccccaa agcgctccaa gagaaagtgc aggaagggg      420
cttgtcccgg aaggcctggc ggctgagcgg ggccaggtcc tggttaggcc accagggtgg    480
gcgtccgcgc cattgtttga gcttgtcggc gctggtggga gagatgaggg caattcctct   540
gggacgcaag tcccctcgaa tggccggggc tggccgggat gttccccgca ggcgctgcc    600
```

```
ctcgagtccc  cccgatggag  agcgcgggcg  cgccttcctt  cgctggcgtc  caaacccggg     660
accagctaga  acacagcagg  gctgggactg  ggttccagcc  ccacgtggag  tctggatttg     720
ttttgttgtg  ttttgctttc  cttcctggaa  gaaatcccga  ggggaccgcc  ctagagcggc     780
agctccagga  cctcggccct  tgggcttccg  ggggtgcagc  cacttaggcc  ccgctcccgg     840
ggagagaggg  attattttt   aagatttatc  cccagggcgc  gcggcatttc  cctgtccctc     900
gtgaatcccg  ttgagagtcc  tccctcccca  acctcctcca  tttccccagc  cagaccgatt     960
cgagagccct  ggagattctg  gcgaggcta   gtgactgggt  agtacaggcc  tctagcccca    1020
ccattgctct  ctctgtcttc  agttccccag  gagggcaatg  gcatcaaaca  gcacagctct    1080
gggggatgtc  aatattgcat  accttttcta  cctaaaggga  aaatgactcg  cttttctgct    1140
tgcaaatatg  gtagtttctg  cttacaaatg  taatacaatg  cccatgacag  ccaaggactg    1200
gaagcataag  ttgctaggtc  ttacaggtga  ttttttacaa  tgaagcaaac  tcactatgtt    1260
agacaccatt  tacattggat  gtctccaact  aacaaaagta  actaaagaca  gatgtaggtg    1320
taaattgaga  gtgaaatttg  acccttaga   ccgtcacaac  ttccttgggc  ttatcctggg    1380
tgcttatagg  agaggtgggc  tccacccaca  aaaatggact  gctcagaaaa  atgagggaga    1440
gagaaagggt  ggccactttc  ccgagccaag  aaattccttg  aaaaaaaatc  agaacatctg    1500
aaaccagaga  gccgatttcc  ttaccgggag  gcagttcctg  gctaacgaag  aggaagcacg    1560
atgggaagaa  aagttcactc  caacggaagc  cagtttgctg  aacatagcag  atcgcccagg    1620
aggactggga  gagactgcaa  accagttcga  gccccccagca  tggcgttagg  tgtcagccag    1680
ctggcaggaa  ggtccaggtg  tctgtgttca  gagtctcaag  gcggctatga  gaggttttcc    1740
tccgagtacc  cagaattctg  ttctaaaacc  aaggccctgg  cagccatccc  accccggtt    1800 cccccagtg   ccacagagcc  cttggacctg  ggctgcagct  cctgtgggac  cccactacac    1860 gaccagggg   gtcctgtgga  gatccttccc  ttcctctacc  tcggcagtgc  ctaccatgct    1920
gcccggagag  acatgctgga  cgccctgggc  atcacggctc  tgttgaatgt  ctcctcggac    1980
tgcccaaacc  actttgaagg  acactatcag  tacaagtgca  tcccagtgga  agataaccac    2040
aaggccgaca  tcagctcctg  gttcatggaa  gccatagagt  acatcgatgc  cgtgaaggac    2100
tgccgtgggc  gcgtgctggt  gcactgccag  gcgggcatct  cgcggtcggc  caccatctgc    2160
ctggcctacc  tgatgatgaa  gaaacggtg   aggctggagg  aggccttcga  gttcgttaag    2220
cagcgccgca  gcatcatctc  gcccaacttc  agcttcatgg  ggcagctgct  gcagttcgag    2280
tcccaggtgc  tggccacgtc  ctgtgctgcg  gaggctgcta  gccctcggg   accctgcgg    2340 gagcggggca  agaccccgc   cacccccacc  tcgcagttcg  tcttcagctt  tccggtctcc    2400
gtgggcgtgc  actcggcccc  cagcagcctg  ccctacctgc  acagccccat  caccacctct    2460
cccagctgtt  agagccgccc  tggggcccc   agaaccagag  ctggctccca  gcaagggtag    2520
gacgggccgc  atgcgggcag  aaagttggga  ctgagcagct  gggagcaggc  gaccgagctc    2580
cttccccatc  atttctcctt  ggccaacgac  gaggccagcc  agaatggcaa  taaggactcc    2640
gaatacataa  taaaagcaaa  cagaacactc  caacttagag  caataacggc  tgccgcagca    2700
gccagggaag  accttggttt  ggtttatgtg  tcagtttcac  ttttccgata  gaaatttctt    2760
acctcatttt  tttaagcagt  aaggcttgaa  gtgatgaaac  ccacagatcc  tagcaaatgt    2820
gcccaaccag  cttactaaa   gggggaggaa  gggagggcaa  agggatgaga  agacaagttt    2880
cccagaagtg  cctggttctg  tgtacttgtc  cctttgttgt  cgttgttgta  gttaaaggaa    2940
```

-continued

```
tttcattttt taaaagaaat cttcgaaggt gtggttttca tttctcagtc accaacagat   3000
gaataattat gcttaataat aaagtattta ttaagacttt cttcagagta tgaaagtaca   3060
aaaagtctag ttacagtgga tttagaatat atttatgttg atgtcaaaca gctgagcacc   3120
gtagcatgca gatgtcaagg cagttaggaa gtaaatggtg tcttgtagat atgtgcaagg   3180
tagcatgatg agcaacttga gtttgttgcc actgagaagc aggcgggttg ggtgggagga   3240
ggaagaaagg gaagaattag gtttgaattg cttttaaaa aaaaagaaa agaaaaagac     3300 agcatctcac tatgttgcca aggctcatct tgagaagcag gcgggttggg tgggaggagg   3360
aagaaaggga agaattaggt ttgaattgct tttaaaaa aaaa                      3404
```

<210> SEQ ID NO 8
<211> LENGTH: 303
<212> TYPE: PRT
<213> ORGANISM: Homo sapiens

<400> SEQUENCE: 8

```
Met Gly Arg Lys Val His Ser Asn Gly Ser Gln Phe Ala Glu His Ser
 1               5                  10                  15

Arg Ser Pro Arg Arg Thr Gly Arg Asp Cys Lys Pro Val Arg Ala Pro
            20                  25                  30

Ser Met Ala Leu Gly Val Ser Gln Leu Ala Gly Arg Ser Arg Cys Leu
        35                  40                  45

Cys Ser Glu Ser Gln Gly Gly Tyr Glu Arg Phe Ser Ser Glu Tyr Pro
    50                  55                  60

Glu Phe Cys Ser Lys Thr Lys Ala Leu Ala Ala Ile Pro Pro Pro Val
65                  70                  75                  80

Pro Pro Ser Ala Thr Glu Pro Leu Asp Leu Gly Cys Ser Ser Cys Gly
                85                  90                  95

Thr Pro Leu His Asp Gln Gly Gly Pro Val Glu Ile Leu Pro Phe Leu
            100                 105                 110

Tyr Leu Gly Ser Ala Tyr His Ala Ala Arg Arg Asp Met Leu Asp Ala
        115                 120                 125

Leu Gly Ile Thr Ala Leu Leu Asn Val Ser Ser Asp Cys Pro Asn His
    130                 135                 140

Phe Glu Gly His Tyr Gln Tyr Lys Cys Ile Pro Val Glu Asp Asn His
145                 150                 155                 160

Lys Ala Asp Ile Ser Ser Trp Phe Met Glu Ala Ile Glu Tyr Ile Asp
                165                 170                 175

Ala Val Lys Asp Cys Arg Gly Arg Val Leu Val His Cys Gln Ala Gly
            180                 185                 190

Ile Ser Arg Ser Ala Thr Ile Cys Leu Ala Tyr Leu Met Met Lys Lys
        195                 200                 205

Arg Val Arg Leu Glu Glu Ala Phe Glu Phe Val Lys Gln Arg Arg Ser
    210                 215                 220

Ile Ile Ser Pro Asn Phe Ser Phe Met Gly Gln Leu Leu Gln Phe Glu
225                 230                 235                 240

Ser Gln Val Leu Ala Thr Ser Cys Ala Ala Glu Ala Ala Ser Pro Ser
                245                 250                 255

Gly Pro Leu Arg Glu Arg Gly Lys Thr Pro Ala Thr Pro Thr Ser Gln
            260                 265                 270

Phe Val Phe Ser Phe Pro Val Ser Val Gly Val His Ser Ala Pro Ser
        275                 280                 285

Ser Leu Pro Tyr Leu His Ser Pro Ile Thr Thr Ser Pro Ser Cys
```

<210> SEQ ID NO 9
<211> LENGTH: 2498
<212> TYPE: DNA
<213> ORGANISM: Homo sapiens

<400> SEQUENCE: 9

| | | | | | |
|---|---|---|---|---|---|
| gctgagcgcc | ggaggagcgt | aggcagggca | gcgctggcgc | cagtggcgac | aggagccgcg | 60 |
| cgaccggcaa | aaatacacgg | gaggccgtcg | ccgaaaagag | tccgcggtcc | tctctcgtaa | 120 |
| acacactctc | ctccaccggc | gcctcccact | ccgctctgcg | cgccgcccgg | ctgggcgccc | 180 |
| gaggccgctc | cgactgctat | gtgaccgcga | ggctgcggga | ggaaggggac | agggaagaag | 240 |
| aggctctccc | gcgggagccc | ttgaggacca | agtttgcggc | cacttctgca | ggcgtccctt | 300 |
| cttagctctc | gcccgcccct | ttctgcagcc | taggcggccc | gggttctctt | ctcttcctcg | 360 |
| cgcgcccagc | cgcctcggtt | cccggcgacc | atggtgacga | tggaggagct | gcgggagatg | 420 |
| gactgcagtg | tgctcaaaag | gctgatgaac | cggacgagag | atggcggcgg | cgcgggcggc | 480 |
| agcggcagcc | acggcaccct | ggggctgccg | agcggcggca | agtgcctgct | gctggactgc | 540 |
| agaccgttcc | tggcgcacag | cgcgggctac | atcctaggtt | cggtcaacgt | gcgctgtaac | 600 |
| accatcgtgc | ggcggcgggc | taagggctcc | gtgagcctgg | agcagatcct | gcccgccgag | 660 |
| gaggaggtac | gcgcccgctt | gcgctccggc | ctctactcgg | cggtcatcgt | ctacgacgag | 720 |
| cgcagcccgc | gcgccgagag | cctccgcgag | gacagcaccg | tgtcgctggt | ggtgcaggcg | 780 |
| ctgcgccgca | acgccgagcg | caccgacatc | tgcctgctca | aaggcggcta | tgagaggttt | 840 |
| tcctccgagt | acccagaatt | ctgttctaaa | accaaggccc | tggcagccat | cccacccccg | 900 |
| gttcccccca | gtgccacaga | gcccttggac | ctgggctgca | gctcctgtgg | accccacta | 960 |
| cacgaccagg | gggtcctgt | ggagatcctt | cccttcctct | acctcggcag | tgcctaccat | 1020 |
| gctgccggga | gagacatgct | ggacgccctg | ggcatcacgg | ctctgttgaa | tgtctcctcg | 1080 |
| gactgcccaa | accactttga | aggacactat | cagtacaagt | gcatcccagt | ggaagataac | 1140 |
| cacaaggccg | acatcagctc | ctggttcatg | gaagccatag | agtacatcga | tgccgtgaag | 1200 |
| gactgccgtg | ggcgcgtgct | ggtgcactgc | caggcgggca | tctcgcggtc | ggccaccatc | 1260 |
| tgcctggcct | acctgatgat | gaagaaacgg | gtgaggctgg | aggaggcctt | cgagttcgtt | 1320 |
| aagcagcgcc | gcagcatcat | ctcgcccaac | ttcagcttca | tggggcagct | gctgcagttc | 1380 |
| gagtcccagg | tgctggccac | gtcctgtgct | gcggaggctg | ctagcccctc | gggacccctg | 1440 |
| cgggagcggg | gcaagacccc | cgccacccc | acctcgcagt | tcgtcttcag | ctttccggtc | 1500 |
| tccgtgggcg | tgcactcggc | ccccagcagc | ctgcccacc | tgcacagccc | catcaccacc | 1560 |
| tctcccagct | gttagagccg | ccctgggggc | cccagaacca | gagctggctc | ccagcaaggg | 1620 |
| taggacgggc | cgcatgcggg | cagaaagttg | ggactgagca | gctgggagca | ggcgaccgag | 1680 |
| ctccttcccc | atcatttctc | cttggccaac | gacgaggcca | gcagaatgg | caataaggac | 1740 |
| tccgaataca | taataaaagc | aaacagaaca | ctccaactta | gagcaataac | ggctgccgca | 1800 |
| gcagccaggg | aagaccttgg | tttggtttat | gtgtcagttt | cacttttccg | atagaaattt | 1860 |
| cttacctcat | ttttttaagc | agtaaggctt | gaagtgatga | aacccacaga | tcctagcaaa | 1920 |
| tgtgcccaac | cagctttact | aaaggggag | gaagggaggg | caaagggatg | agaagacaag | 1980 |
| tttcccagaa | gtgcctggtt | ctgtgtactt | gtcccttgt | tgtcgttgtt | gtagttaaag | 2040 |
| gaatttcatt | ttttaaaaga | aatcttcgaa | ggtgtggttt | tcatttctca | gtcaccaaca | 2100 |

-continued

```
gatgaataat tatgcttaat aataaagtat ttattaagac tttcttcaga gtatgaaagt   2160
acaaaaagtc tagttacagt ggatttagaa tatatttatg ttgatgtcaa acagctgagc   2220
accgtagcat gcagatgtca aggcagttag gaagtaaatg gtgtcttgta gatatgtgca   2280
aggtagcatg atgagcaact tgagtttgtt gccactgaga agcaggcggg ttgggtggga   2340
ggaggaagaa agggaagaat taggtttgaa ttgcttttta aaaaaaaaag aaaagaaaaa   2400
gacagcatct cactatgttg ccaaggctca tcttgagaag caggcgggtt gggtgggagg   2460
aggaagaaag ggaagaatta ggtttgaatt gcttttt                            2498
```

<210> SEQ ID NO 10
<211> LENGTH: 394
<212> TYPE: PRT
<213> ORGANISM: Homo sapiens

<400> SEQUENCE: 10

```
Met Val Thr Met Glu Glu Leu Arg Glu Met Asp Cys Ser Val Leu Lys
  1               5                  10                  15

Arg Leu Met Asn Arg Asp Glu Asn Gly Gly Ala Gly Gly Ser Gly
                 20                  25                  30

Ser His Gly Thr Leu Gly Leu Pro Ser Gly Gly Lys Cys Leu Leu Leu
             35                  40                  45

Asp Cys Arg Pro Phe Leu Ala His Ser Ala Gly Tyr Ile Leu Gly Ser
         50                  55                  60

Val Asn Val Arg Cys Asn Thr Ile Val Arg Arg Ala Lys Gly Ser
 65                  70                  75                  80

Val Ser Leu Glu Gln Ile Leu Pro Ala Glu Glu Val Arg Ala Arg
                 85                  90                  95

Leu Arg Ser Gly Leu Tyr Ser Ala Val Ile Val Tyr Asp Glu Arg Ser
                100                 105                 110

Pro Arg Ala Glu Ser Leu Arg Glu Asp Ser Thr Val Ser Leu Val Val
            115                 120                 125

Gln Ala Leu Arg Arg Asn Ala Glu Arg Thr Asp Ile Cys Leu Leu Lys
        130                 135                 140

Gly Gly Tyr Glu Arg Phe Ser Ser Glu Tyr Pro Glu Phe Cys Ser Lys
145                 150                 155                 160

Thr Lys Ala Leu Ala Ala Ile Pro Pro Val Pro Pro Ser Ala Thr
                165                 170                 175

Glu Pro Leu Asp Leu Gly Cys Ser Cys Gly Thr Pro Leu His Asp
            180                 185                 190

Gln Gly Gly Pro Val Glu Ile Leu Pro Phe Leu Tyr Leu Gly Ser Ala
        195                 200                 205

Tyr His Ala Ala Arg Arg Asp Met Leu Asp Ala Leu Gly Ile Thr Ala
    210                 215                 220

Leu Leu Asn Val Ser Ser Asp Cys Pro Asn His Phe Glu Gly His Tyr
225                 230                 235                 240

Gln Tyr Lys Cys Ile Pro Val Glu Asp Asn His Lys Ala Asp Ile Ser
                245                 250                 255

Ser Trp Phe Met Glu Ala Ile Glu Tyr Ile Asp Ala Val Lys Asp Cys
            260                 265                 270

Arg Gly Arg Val Leu Val His Cys Gln Ala Gly Ile Ser Arg Ser Ala
        275                 280                 285

Thr Ile Cys Leu Ala Tyr Leu Met Met Lys Lys Arg Val Arg Leu Glu
    290                 295                 300
```

Glu Ala Phe Glu Phe Val Lys Gln Arg Arg Ser Ile Ile Ser Pro Asn
305                 310                 315                 320

Phe Ser Phe Met Gly Gln Leu Leu Gln Phe Glu Ser Gln Val Leu Ala
            325                 330                 335

Thr Ser Cys Ala Ala Glu Ala Ala Ser Pro Ser Gly Pro Leu Arg Glu
        340                 345                 350

Arg Gly Lys Thr Pro Ala Thr Pro Thr Ser Gln Phe Val Phe Ser Phe
        355                 360                 365

Pro Val Ser Val Gly Val His Ser Ala Pro Ser Ser Leu Pro Tyr Leu
    370                 375                 380

His Ser Pro Ile Thr Thr Ser Pro Ser Cys
385                 390

<210> SEQ ID NO 11
<211> LENGTH: 3809
<212> TYPE: DNA
<213> ORGANISM: Homo sapiens

<400> SEQUENCE: 11

```
gccgctgtta tgcgtattcc cgtagaccca agcaccagcc gccgcttcac acctccctcc      60
ccggccttcc cctgcggcgg cggcggcggc aagatgggcg agaacagcgg cgcgctgagc     120
gcgcaggcgg ccgtggggcc cggagggcgc gcccggcccg aggtgcgctc gatggtggac     180
gtgctggcgg accacgcagg cgagctcgtg cgcaccgaca gccccaactt cctctgctcc     240
gtgctgccct cgcactggcg ctgcaacaag acgctgcccg tcgccttcaa ggtggtggca     300
ttggggacg tgccggatgg tacggtggtg actgtgatgg caggcaatga cgagaactac      360
tccgctgagc tgcgcaatgc ctcggccgtc atgaagaacc aggtggccag gttcaacgac     420
cttcgcttcg tgggccgcag tgggcgaggg aagagtttca ccctgaccat cactgtgttc     480
accaacccca cccaagtggc gacctaccac cgagccatca aggtgaccgt ggacggaccc     540
cgggagccca cggcaccg gcagaagctg aggaccagga ccaagccgtt cctgaccgc      600
tttggggacc tggaacggct cgcatgcgcg gtgaccga gcacacccag ccccgaggc       660
tcactcagca ccacaagcca cttcagcagc agccccaga ccccaatcca aggcacctcg      720
gaactgaacc cattctccga ccccgccag tttgaccgct ccttccccac gctgccaacc      780
ctcacggaga gccgcttccc agaccccagg atgcattatc ccggggccat gtcagctgcc      840
ttccctaca cgccacgcc ctcgggcacg agcatcagca gctcagcgt ggcgggcatg        900
ccggccacca gccgcttcca ccatacctac ctccgccac cctacccggg ggccccgcag      960
aaccagagcg ggcccttcca ggccaacccg tccccctacc acctctacta cgggacatcc     1020
tctggctcct accagttctc catggtggcc ggcagcagca gtggggcga ccgctcacct     1080
acccgcatgc tggcctcttg caccagcagc gctgcctctg tcgccgccgg caacctcatg     1140
aaccccagcc tgggcggcca gagtgatggc gtggaggcca acgcagcca cagcaactca     1200
cccacgccc tgagcacgcc aggccgcatg gatgaggccc tgtggcggcc ctactgaccg     1260
ccctggtgga ctcctcccgc tggaggcggg acccctaaca accttcaaga ccagtgatgg     1320
gccggctccg aggctccggg cgggaatggg acctgcgctc cagggtggtc tcggtcccag     1380
ggtggtccca gctggtggga gcctctggct gcatctgtgc agccacatcc ttgtacagag     1440
gcataggtta ccaccccac cccggccgg gatactgccc ccggcccaga tcctggccgt      1500
ctcatcccat acttctgtgg ggaatcagcc tcctgccacc ccccggaag gacctcactg     1560
```

```
tctccagcta tgcccagtgc tgcatgggac ccatgtctcc tgggacagag gccatctctc   1620
ttccagagag aggcagcatt ggcccacagg ataagcctca ggccctggga aacctcccga   1680
cccctgcacc ttcgttggag cccctgcatc ccctgggtcc agcccctct gcatttacac    1740 agatttgagt cagaactgga aagtgtcccc caccccacc accctcgagc ggggttcccc    1800
tcattgtaca gatggggcag gacccagcac gctgctggca gagatggttt gagaacacat   1860
ccaagccagt cccccagcc cagcttcccc tccgttccta actgttggct ttcccccagc    1920
cgcacggtcc caggcccaga gaagatgagt ctatggcatc aggttcttaa accaggaaag   1980
cacctacaga ccggctcctc catgcacttt accagctcaa cgcatccact ctctgttctc   2040
ttggcagggc gggggagggg ggataggagg tccccttcc cctaggtggt ctcataattc     2100
catttgtgga gagaacagga gggccagata ataggtcct agcagaaggc attgaggtga     2160
gggatcattt tgggtcagac atcaatgtcc ctgtccccc tgggtccagc caagctgtgc     2220
cccatccccc aagcctcctg ggaggatcca gccaaatctt gcgactcctg cacacacct     2280 gtctgtaacc tgttttgtgc tctgaaagca atagtcctg agcaaaaaaa aaaaaaaaa     2340 acaaaaaaac aaaaaaaaaa caaaacagtt tttaaaactg attttagaaa agaagctta    2400 atctaacgtt ttcaaacaca aggtctctta caggtatagt tccgtgatta tgatagctct   2460
gtgattataa gcaacatccc cgcccctct cccccccgcg accccccagc tgcctcctga    2520
gggtgtgggg ttattagggt ctcaatactt tctcaagggg ctacactccc catcaggcag   2580
catcccacca gcctgcacca caggctcccc tgggaggacg agggaaacgc tgatgagacg   2640
ctgggcatct ctcctctgtg gctctaggac atctgtccag gaggctgggc ggaggtgggc   2700
aggatgtgag aggtggggag tactggctgt gcgtggcagg acagaagcac tgtaaagggc   2760
tctccagcgc agctcagctg cactgcgttc cgaggtgaag tcttgcccct gaattttgca   2820
aaatgggaaa gtgggcgctt gccaagggcc aggctgcatg gattctcaca tcagagttct   2880
ctggccctag aaaggcttag aaaaggcgta agggaactca taaaggctag cagcatgcgg   2940
tattttaact ttctgcctcg gcctctgtgg atgcagaaat ctgccctaca aaatgctctt   3000
cattggttgt ctctgtgaga gcactgtccc caccccaacct gtcacaacgg ccagaaccat   3060
acaccagaga cacactggca ggttaggcag tccttctggt gatcctattc cattccctcc    3120
tgctgcggtt tctcttggcc tgtcctcact ggaaaaacag tctccatctc ctcaaaatag    3180
ttgctgactc cctgcaccca aggggcctct ccatgccttc ttaggaagca gctatgaatc    3240
cattgtcctt gtagtttctt ccctcctgtt ctctggttat agctggtccc aggtcagcgt    3300
gggaggcacc tttgggttcc cagtgcccag cactttgtag tctcatccca gattactaac    3360
ccttcctgat cctggagagg cagggatagt aaataaattg ctcttcctac cccatccccc    3420
atcccctgac aaaagtgac ggcagccgta ctgagtctgt aaggcccaaa gtgggtacag     3480
acagcctggg ctggtaaaag taggtcctta tttacaaggc tgcgttaaag ttgtactagg    3540
caaacacact gatgtaggaa gcacgaggaa aggaagacgt tttgatatag tgttactgtg    3600
agcctgtcag tagtgggtac caatctttg tgacatattg tcatgctgag gtgtgacacc    3660
tgctgcactc atctgatgta aaaccatccc agagctggcg agaggatgga gctgggtgga    3720
aactgctttg cactatcgtt tgcttggtgt ttgtttttaa cgcacaactt gcttgtacag    3780
taaactgtct tctgtactat ttaactgta                                     3809
```

<210> SEQ ID NO 12
<211> LENGTH: 415

<212> TYPE: PRT
<213> ORGANISM: Homo sapiens

<400> SEQUENCE: 12

```
Met Arg Ile Pro Val Asp Pro Ser Thr Ser Arg Arg Phe Thr Pro Pro
 1               5                  10                  15

Ser Pro Ala Phe Pro Cys Gly Gly Gly Gly Lys Met Gly Glu Asn
                20                  25                  30

Ser Gly Ala Leu Ser Ala Gln Ala Ala Val Gly Pro Gly Gly Arg Ala
            35                  40                  45

Arg Pro Glu Val Arg Ser Met Val Asp Val Leu Ala Asp His Ala Gly
 50                  55                  60

Glu Leu Val Arg Thr Asp Ser Pro Asn Phe Leu Cys Ser Val Leu Pro
 65                  70                  75                  80

Ser His Trp Arg Cys Asn Lys Thr Leu Pro Val Ala Phe Lys Val Val
                85                  90                  95

Ala Leu Gly Asp Val Pro Asp Gly Thr Val Val Thr Val Met Ala Gly
                100                 105                 110

Asn Asp Glu Asn Tyr Ser Ala Glu Leu Arg Asn Ala Ser Ala Val Met
            115                 120                 125

Lys Asn Gln Val Ala Arg Phe Asn Asp Leu Arg Phe Val Gly Arg Ser
130                 135                 140

Gly Arg Gly Lys Ser Phe Thr Leu Thr Ile Thr Val Phe Thr Asn Pro
145                 150                 155                 160

Thr Gln Val Ala Thr Tyr His Arg Ala Ile Lys Val Thr Val Asp Gly
                165                 170                 175

Pro Arg Glu Pro Arg Arg His Arg Gln Lys Leu Glu Asp Gln Thr Lys
            180                 185                 190

Pro Phe Pro Asp Arg Phe Gly Asp Leu Glu Arg Leu Arg Met Arg Val
            195                 200                 205

Thr Pro Ser Thr Pro Ser Pro Arg Gly Ser Leu Ser Thr Thr Ser His
210                 215                 220

Phe Ser Ser Gln Pro Gln Thr Pro Ile Gln Gly Thr Ser Glu Leu Asn
225                 230                 235                 240

Pro Phe Ser Asp Pro Arg Gln Phe Asp Arg Ser Phe Pro Thr Leu Pro
                245                 250                 255

Thr Leu Thr Glu Ser Arg Phe Pro Asp Pro Arg Met His Tyr Pro Gly
                260                 265                 270

Ala Met Ser Ala Ala Phe Pro Tyr Ser Ala Thr Pro Ser Gly Thr Ser
            275                 280                 285

Ile Ser Ser Leu Ser Val Ala Gly Met Pro Ala Thr Ser Arg Phe His
290                 295                 300

His Thr Tyr Leu Pro Pro Pro Tyr Pro Gly Ala Pro Gln Asn Gln Ser
305                 310                 315                 320

Gly Pro Phe Gln Ala Asn Pro Ser Pro Tyr His Leu Tyr Tyr Gly Thr
                325                 330                 335

Ser Ser Gly Ser Tyr Gln Phe Ser Met Val Ala Gly Ser Ser Ser Gly
            340                 345                 350

Gly Asp Arg Ser Pro Thr Arg Met Leu Ala Ser Cys Thr Ser Ser Ala
355                 360                 365

Ala Ser Val Ala Ala Gly Asn Leu Met Asn Pro Ser Leu Gly Gly Gln
370                 375                 380

Ser Asp Gly Val Glu Ala Asp Gly Ser His Ser Asn Ser Pro Thr Ala
385                 390                 395                 400
```

```
Leu Ser Thr Pro Gly Arg Met Asp Glu Ala Val Trp Arg Pro Tyr
            405                 410                 415

<210> SEQ ID NO 13
<211> LENGTH: 2372
<212> TYPE: DNA
<213> ORGANISM: Homo sapiens

<400> SEQUENCE: 13
cgaagctagg gcggggcccg cgggctgagg cagcggctgt ggcggcgacg ctgggcgtga      60
ggtggcggcg gccgcgccct ggttgggtcc ccactgctct cggggggcgcc atggacgagg    120 ccgtgggcga cctgaagcag gcgcttccct gtgtggccga gtcgccaacg gtccacgtgg    180
aggtgcatca gcgcggcagc agcactgcaa agaaagaaga cataaacctg agtgttagaa    240
agctactcaa cagacataat attgtgtttg gtgattacac atggactgag tttgatgaac    300
cttttttgac cagaaatgtg cagtctgtgt ctattattga cacagaatta aaggttaaag    360
actcacagcc catcgatttg agtgcatgca ctgttgcact tcacattttc agctgaatg     420 aagatggccc cagcagtgaa atctggagg aagagacaga aaacataatt gcagcaaatc      480
actgggttct acctgcagct gaattccatg gctttgggga cagcttggta tacgatgtgg    540
aagtcaaatc ccatctcctc gattatgtga tgacaacttt actgttttca gacaagaacg    600
tcaacagcaa cctcatcacc tggaaccggg tggtgctgct ccacggtcct cctggcactg    660
gaaaaacatc cctgtgtaaa gcgttagccc agaaattgac aattagactt tcaagcaggt    720
accgatatgg ccaattaatt gaaataaaca gccacagcct cttttctaag tggttttcgg    780
aaagtggcaa gctggtaacc aagatgtttc agaagattca ggatttgatt gatgataaag    840
acgccctggt gttcgtgctg attgatgagg tggagagtct cacagccgcc cgaaatgcct    900
gcagggcggg caccgagcca tcagatgcca tccgcgtggt caatgctgtc ttgacccaaa    960
ttgatcagat taaaaggcat tccaatgttg tgattctgac cacttctaac atcaccgaga   1020
agatcgacgt ggccttcgtg acagggctg acatcaagca gtacattggg ccaccctctg   1080
cagcagccat cttcaaaatc tacctctctt gtttggaaga actgatgaag tgtcagatca   1140 tatccctcg ccagcagctg ctgacccctcc gagagctaga gatgattggc ttcattgaaa   1200
acaacgtgtc aaaattgagc cttcttttga atgacatttc aaggaagagc gagggcctca   1260
gcggccgggt cctgagaaaa ctccccttc tggctcatgc gctgtatgtc caggccccca   1320
ccgtcaccat agaggggttc ctccaggccc tgtctctggc agtggacaag cagtttgaag   1380
agagaaagaa gcttgcagct acatctgat cctgggcttc cccatctggt gcttttccca    1440
tggagaacac acaaccagta agtgaggttg ccccacacag ccgtctccca gggaatccct   1500
tctgcaaacc aaacgttact tagactgcaa gctagaaagc caccaaggcc aggctttgtt   1560
aaaagaagtg tattctatt atgttgttt aaaatgcata ctgagagaca acatcttgt     1620 cattttcact gtttgtaaaa gataattcag attgtttgtc tccttgtgaa gaaccatcga   1680
aacctgtttg ttcccagccc accccagtg atgggatgc ataatgccag caagttttgt    1740
ttaacagcaa aaaaggaaga ttaatgcagg tgttatagaa gccagaagag aaactgtgtc   1800
accctaaaga agcatataat catagcatta aaaatgcaca cattactcca ggtggaaggt   1860
ggcaattgct ttctgatatc agctcgtttg atttagtgca aaaatgtttt caagactatt   1920
taatggatgt aaaaaagcct atttctacat tataccaact gagaaaaaaa tggtcggtaa   1980
agtgttcttt cataataaat aatcagacat ggtcccattt gcaggaaaag tgcagactct   2040
```

```
gagtgttcca gggaaacaca tgctggacat cccttgtaac ccggtatggg cgccctgca    2100 ttgctgggat gtttctgccc acggttttgt ttgtgcaata acgttatcac atttctaatg    2160
aggattcaca ttaatataat ataaaataaa taggtcagtt actggtctct ttctccgaat    2220
gttatgtttt gcttttatct cacagtaaaa taaatataat taatggtttg catgtgaaat    2280
tcacttttga aagaacatgt taccttacct tttgttttag aagttttcaa gtattaaaat    2340 atttttaga aaaaaaaaaa aaaaaaaaaa aa                                   2372
```

<210> SEQ ID NO 14
<211> LENGTH: 432
<212> TYPE: PRT
<213> ORGANISM: Homo sapiens

<400> SEQUENCE: 14

```
Met Asp Glu Ala Val Gly Asp Leu Lys Gln Ala Leu Pro Cys Val Ala
  1               5                  10                  15

Glu Ser Pro Thr Val His Val Glu Val His Gln Arg Gly Ser Ser Thr
                 20                  25                  30

Ala Lys Lys Glu Asp Ile Asn Leu Ser Val Arg Lys Leu Leu Asn Arg
             35                  40                  45

His Asn Ile Val Phe Gly Asp Tyr Thr Trp Thr Glu Phe Asp Glu Pro
         50                  55                  60

Phe Leu Thr Arg Asn Val Gln Ser Val Ser Ile Ile Asp Thr Glu Leu
 65                  70                  75                  80

Lys Val Lys Asp Ser Gln Pro Ile Asp Leu Ser Ala Cys Thr Val Ala
                 85                  90                  95

Leu His Ile Phe Gln Leu Asn Glu Asp Gly Pro Ser Ser Glu Asn Leu
            100                 105                 110

Glu Glu Glu Thr Glu Asn Ile Ile Ala Ala Asn His Trp Val Leu Pro
        115                 120                 125

Ala Ala Glu Phe His Gly Leu Trp Asp Ser Leu Val Tyr Asp Val Glu
130                 135                 140

Val Lys Ser His Leu Leu Asp Tyr Val Met Thr Thr Leu Leu Phe Ser
145                 150                 155                 160

Asp Lys Asn Val Asn Ser Asn Leu Ile Thr Trp Asn Arg Val Val Leu
                165                 170                 175

Leu His Gly Pro Pro Gly Thr Gly Lys Thr Ser Leu Cys Lys Ala Leu
            180                 185                 190

Ala Gln Lys Leu Thr Ile Arg Leu Ser Ser Arg Tyr Arg Tyr Gly Gln
        195                 200                 205

Leu Ile Glu Ile Asn Ser His Ser Leu Phe Ser Lys Trp Phe Ser Glu
    210                 215                 220

Ser Gly Lys Leu Val Thr Lys Met Phe Gln Lys Ile Gln Asp Leu Ile
225                 230                 235                 240

Asp Asp Lys Asp Ala Leu Val Phe Val Leu Ile Asp Glu Val Glu Ser
                245                 250                 255

Leu Thr Ala Ala Arg Asn Ala Cys Arg Ala Gly Thr Glu Pro Ser Asp
            260                 265                 270

Ala Ile Arg Val Val Asn Ala Val Leu Thr Gln Ile Asp Gln Ile Lys
        275                 280                 285

Arg His Ser Asn Val Val Ile Leu Thr Thr Ser Asn Ile Thr Glu Lys
    290                 295                 300

Ile Asp Val Ala Phe Val Asp Arg Ala Asp Ile Lys Gln Tyr Ile Gly
```

```
                305                 310                 315                 320

Pro Pro Ser Ala Ala Ile Phe Lys Ile Tyr Leu Ser Cys Leu Glu
            325                 330                 335

Glu Leu Met Lys Cys Gln Ile Ile Tyr Pro Arg Gln Gln Leu Leu Thr
            340                 345                 350

Leu Arg Glu Leu Glu Met Ile Gly Phe Ile Glu Asn Asn Val Ser Lys
        355                 360                 365

Leu Ser Leu Leu Leu Asn Asp Ile Ser Arg Lys Ser Glu Gly Leu Ser
        370                 375                 380

Gly Arg Val Leu Arg Lys Leu Pro Phe Leu Ala His Ala Leu Tyr Val
385                 390                 395                 400

Gln Ala Pro Thr Val Thr Ile Glu Gly Phe Leu Gln Ala Leu Ser Leu
            405                 410                 415

Ala Val Asp Lys Gln Phe Glu Glu Arg Lys Lys Leu Ala Ala Tyr Ile
            420                 425                 430

<210> SEQ ID NO 15
<211> LENGTH: 1421
<212> TYPE: DNA
<213> ORGANISM: Homo sapiens

<400> SEQUENCE: 15
acttactgcg ggacggcctt ggagagtact cgggttcgtg aacttcccgg aggcgcaatg      60
agctgcatta acctgcccac tgtgctgccc ggctccccca gcaagacccg ggggcagatc     120
caggtgattc tcgggccgat gttctcagga aaaagcacag agttgatgag acgcgtccgt     180
cgcttccaga ttgctcagta caagtgcctg gtgatcaagt atgccaaaga cactcgctac     240
agcagcagct tctgcacaca tgaccggaac accatggagg cgctgcccgc ctgcctgctc     300
cgagacgtgg cccaggaggc cctgggcgtg gctgtcatag catcgacga ggggcagttt     360 ttccctgaca tcatggagtt ctgcgaggcc atggccaacg ccgggaagac cgtaattgtg     420
gctgcactgg atgggacctt ccagaggaag ccatttgggg ccatcctgaa cctggtgccg     480
ctggccgaga gcgtggtgaa gctgacggcg gtgtgcatgg agtgcttccg ggaagccgcc     540
tataccaaga ggctcggcac agagaaggag gtcgaggtga ttgggggagc agacaagtac     600
cactccgtgt gtcggctctg ctacttcaag aaggcctcag gccagcctgc cgggccggac     660
aacaaagaga actgcccagt gccaggaaag ccaggggaag ccgtggctgc aggaagctc      720 tttgccccac agcagattct gcaatgcagc cctgccaact gagggacctg caagggccgc     780
ccgctccctt cctgccactg ccgcctactg gacgctgccc tgcatgctgc ccagccactc     840
caggaggaag tcgggaggcg tggagggtga ccacaccttg gccttctggg aactctcctt     900
tgtgtggctg ccccacctgc cgcatgctcc ctcctctcct acccactggt ctgcttaaag     960
cttccctctc agctgctggg acgatcgccc aggctggagc tggccccgct ggtggcctg    1020 ggatctggca cactccctct ccttggggtg agggacagag ccccacgctg ttgacatcag    1080
cctgcttctt ccctctgcg gctttcactg ctgagtttct gttctccctg ggaagcctgt    1140
gccagcacct ttgagccttg cccacactg aggcttaggc ctctctgcct gggatgggct    1200
cccaccctcc cctgaggatg gcctggattc acgccctctt gtttccttt gggctcaaag    1260 cccttcctac ctctggtgat ggtttccaca ggaacaacag catctttcac caagatgggt    1320
ggcaccaacc ttgctgggac ttggatccca ggggcttatc tcttcaagtg tggagagggc    1380
agggtccacg cctctgctgt agcttatgaa attaactaat t                        1421
```

<210> SEQ ID NO 16
<211> LENGTH: 234
<212> TYPE: PRT
<213> ORGANISM: Homo sapiens

<400> SEQUENCE: 16

Met Ser Cys Ile Asn Leu Pro Thr Val Leu Pro Gly Ser Pro Ser Lys
1               5                   10                  15

Thr Arg Gly Gln Ile Gln Val Ile Leu Gly Pro Met Phe Ser Gly Lys
            20                  25                  30

Ser Thr Glu Leu Met Arg Arg Val Arg Arg Phe Gln Ile Ala Gln Tyr
        35                  40                  45

Lys Cys Leu Val Ile Lys Tyr Ala Lys Asp Thr Arg Tyr Ser Ser Ser
    50                  55                  60

Phe Cys Thr His Asp Arg Asn Thr Met Glu Ala Leu Pro Ala Cys Leu
65                  70                  75                  80

Leu Arg Asp Val Ala Gln Glu Ala Leu Gly Val Ala Val Ile Gly Ile
                85                  90                  95

Asp Glu Gly Gln Phe Phe Pro Asp Ile Met Glu Phe Cys Glu Ala Met
            100                 105                 110

Ala Asn Ala Gly Lys Thr Val Ile Val Ala Ala Leu Asp Gly Thr Phe
        115                 120                 125

Gln Arg Lys Pro Phe Gly Ala Ile Leu Asn Leu Val Pro Leu Ala Glu
    130                 135                 140

Ser Val Val Lys Leu Thr Ala Val Cys Met Glu Cys Phe Arg Glu Ala
145                 150                 155                 160

Ala Tyr Thr Lys Arg Leu Gly Thr Glu Lys Glu Val Glu Val Ile Gly
                165                 170                 175

Gly Ala Asp Lys Tyr His Ser Val Cys Arg Leu Cys Tyr Phe Lys Lys
            180                 185                 190

Ala Ser Gly Gln Pro Ala Gly Pro Asp Asn Lys Glu Asn Cys Pro Val
        195                 200                 205

Pro Gly Lys Pro Gly Glu Ala Val Ala Ala Arg Lys Leu Phe Ala Pro
    210                 215                 220

Gln Gln Ile Leu Gln Cys Ser Pro Ala Asn
225                 230

<210> SEQ ID NO 17
<211> LENGTH: 1662
<212> TYPE: DNA
<213> ORGANISM: Homo sapiens

<400> SEQUENCE: 17
gcggccgcga ccgccgggga cgagcttgga ggaaaaggaa ccgggagccg cccacccggg     60
ggcgctctcc ggaccccag ggtcctagcg cgcggccctt accgagcctg ggcgcccgga    120
tttcggsagc ggatcgcctt ccgggttgg cggcccgcct gattgggaac agccggccgg    180
ttgccggggg aacgcgggag tcgggcccga cctgagccac gcgggcttgg tgcccacctg    240
tgcgcgccgc ctgcgaagaa ggaacggtct agggagaagg cgccgccggc cgcccccgtc    300
cccaccgcgg ccgtcgctgg agagttcgag ccgcctagcg cccctggagc tcccaacca    360 tgaagctcaa cttctccctg cgactgcgga tcttcaacct caactgctgg ggcattccgt    420
acttgagcaa gcaccgggcc gaccgcatga ggcgcctggg agactttctg aaccaggaga    480
gcttcgacct ggctttgctg gaggaggtgt ggagtgagca ggacttccag tacctgagac    540

-continued

```
agaagctgtc acctacctac ccagctgcac accacttccg gagcggaatc attggcagtg    600
gcctctgtgt cttctccaaa catccaatcc aggagcttac ccagcacatc tacactctca    660
atggctaccc ctacatgatc catcatggtg actggttcag tgggaaggct gtggggctgc    720
tggtgctcca tctaagtggc atggtgctca acgcctatgt gacccatctc catgccgaat    780
acaatcgaca gaaggacatc tacctagcac atcgtgtggc ccaagcttgg gaattggccc    840
agttcatcca ccacacatcc aagaaggcag acgtggttct gttgtgtgga gacctcaaca    900
tgcacccaga agacctgggc tgctgcctgc tgaaggagtg gacagggctt catgatgcct    960
atcttgaaac tcgggacttc aagggctctg aggaaggcaa cacaatggta cccaagaact   1020
gctacgtcag ccagcaggag ctgaagccat tccctttgg tgtccgcatt gactacgtgc    1080
tttacaaggc agtttctggg ttttacatct cctgtaagag ttttgaaacc actacaggct   1140
tgaccctca cagtggcacc cccctctctg atcatgaagc cctgatggct actctgtttg    1200
tgaggcacag cccccacag cagaacccca gctctaccca cggaccagca gagaggtcgc     1260
cgttgatgtg tgtgctaaag gaggcctgga cggagctggg tctgggcatg gctcaggctc   1320
gctggtgggc caccttcgct agctatgtga ttggcctggg gctgcttctc ctggcactgc   1380
tgtgtgtcct ggcggctgga ggaggggccg gggaagctgc catactgctc tggaccccca   1440
gtgtagggct ggtgctgtgg gcaggtgcat tctacctctt ccacgtacag gaggtcaatg   1500
gcttatatag ggcccaggct gagctccagc atgtgctagg aagggcaagg gaggcccagg   1560
atctgggccc agagcctcag ccagccctac tcctggggca gcaggagggg gacagaacta   1620
agaacaata aagcttggcc ctttaaaaaa aaaaaaaaaa aa                       1662
```

<210> SEQ ID NO 18
<211> LENGTH: 423
<212> TYPE: PRT
<213> ORGANISM: Homo sapiens

<400> SEQUENCE: 18

```
Met Lys Leu Asn Phe Ser Leu Arg Leu Arg Ile Phe Asn Leu Asn Cys
1               5                   10                  15

Trp Gly Ile Pro Tyr Leu Ser Lys His Arg Ala Asp Arg Met Arg Arg
            20                  25                  30

Leu Gly Asp Phe Leu Asn Gln Glu Ser Phe Asp Leu Ala Leu Leu Glu
        35                  40                  45

Glu Val Trp Ser Glu Gln Asp Phe Gln Tyr Leu Arg Gln Lys Leu Ser
    50                  55                  60

Pro Thr Tyr Pro Ala Ala His His Phe Arg Ser Gly Ile Ile Gly Ser
65                  70                  75                  80

Gly Leu Cys Val Phe Ser Lys His Pro Ile Gln Glu Leu Thr Gln His
                85                  90                  95

Ile Tyr Thr Leu Asn Gly Tyr Pro Tyr Met Ile His His Gly Asp Trp
            100                 105                 110

Phe Ser Gly Lys Ala Val Gly Leu Leu Val Leu His Leu Ser Gly Met
        115                 120                 125

Val Leu Asn Ala Tyr Val Thr His Leu His Ala Glu Tyr Asn Arg Gln
    130                 135                 140

Lys Asp Ile Tyr Leu Ala His Arg Val Ala Gln Ala Trp Glu Leu Ala
145                 150                 155                 160

Gln Phe Ile His His Thr Ser Lys Lys Ala Asp Val Val Leu Leu Cys
                165                 170                 175
```

-continued

```
Gly Asp Leu Asn Met His Pro Glu Asp Leu Gly Cys Cys Leu Leu Lys
            180                 185                 190
Glu Trp Thr Gly Leu His Asp Ala Tyr Leu Glu Thr Arg Asp Phe Lys
        195                 200                 205
Gly Ser Glu Glu Gly Asn Thr Met Val Pro Lys Asn Cys Tyr Val Ser
    210                 215                 220
Gln Gln Glu Leu Lys Pro Phe Pro Phe Gly Val Arg Ile Asp Tyr Val
225                 230                 235                 240
Leu Tyr Lys Ala Val Ser Gly Phe Tyr Ile Ser Cys Lys Ser Phe Glu
                245                 250                 255
Thr Thr Thr Gly Phe Asp Pro His Ser Gly Thr Pro Leu Ser Asp His
            260                 265                 270
Glu Ala Leu Met Ala Thr Leu Phe Val Arg His Ser Pro Pro Gln Gln
        275                 280                 285
Asn Pro Ser Ser Thr His Gly Pro Ala Glu Arg Ser Pro Leu Met Cys
    290                 295                 300
Val Leu Lys Glu Ala Trp Thr Glu Leu Gly Leu Gly Met Ala Gln Ala
305                 310                 315                 320
Arg Trp Trp Ala Thr Phe Ala Ser Tyr Val Ile Gly Leu Gly Leu Leu
                325                 330                 335
Leu Leu Ala Leu Leu Cys Val Leu Ala Ala Gly Gly Ala Gly Glu
            340                 345                 350
Ala Ala Ile Leu Leu Trp Thr Pro Ser Val Gly Leu Val Leu Trp Ala
        355                 360                 365
Gly Ala Phe Tyr Leu Phe His Val Gln Glu Val Asn Gly Leu Tyr Arg
    370                 375                 380
Ala Gln Ala Glu Leu Gln His Val Leu Gly Arg Ala Arg Glu Ala Gln
385                 390                 395                 400
Asp Leu Gly Pro Glu Pro Gln Pro Ala Leu Leu Leu Gly Gln Gln Glu
                405                 410                 415
Gly Asp Arg Thr Lys Glu Gln
            420
```

<210> SEQ ID NO 19
<211> LENGTH: 2731
<212> TYPE: DNA
<213> ORGANISM: Homo sapiens

<400> SEQUENCE: 19

```
gcgcttggcg ggagatagaa aagtgcttca acccgcgccg gcggcgactg cagttcctgc    60
gagcgaggag cgcgggacct gctgacacgc tgacgccttc gagcgcggcc cggggcccgg   120
agcggccgga gcagcccggg tcctgacccc ggcccggctc ccgctccggg ctctgccggc   180
gggcgggcga gcgcggcgcg gtccgggccg gggggatgtc tcggcggacg cgctgcgagg   240
atctggatga gctgcactac caggacacag attcagatgt gccggagcag agggatagca   300
agtgcaaggt caaatggacc catgaggagg acgagcagct gagggccctg gtgaggcagt   360
ttggacagca ggactggaag ttcctggcca gccacttccc taaccgcact gaccagcaat   420
gccagtacag gtggctgaga gttttgaatc agaccttgt caaggggcca tggaccaaag   480
aggaagacca aaaagtcatc gagctggtta agaagtatgg cacaaagcag tggacactga   540
ttgccaagca cctgaagggc ggctgggga agcagtgccg tgaacgctgg cacaaccacc   600
tcaaccctga ggtgaagaag tcttgctgga ccgaggagga ggaccgcatc atctgcgagg   660
cccacaaggt gctgggcaac cgctgggccg agatcgccaa gatgttgcca ggaggacag   720
```

```
acaatgctgt gaagaatcac tggaactcta ccatcaaaag gaaggtggac acaggaggct     780
tcttgagcga gtccaaagac tgcaagcccc cagtgtactt gctgctggag ctcgaggaca     840
aggacggcct ccagagtgcc cagcccacgg aaggccaggg aagtcttctg accaactggc     900
cctccgtccc tcctaccata aggaggagg aaaacagtga ggaggaactt gcagcagcca      960
ccacatcgaa ggaacaggag cccatcggta cagatctgga cgcagtgcga acaccagagc    1020
ccttggagga attcccgaag cgtgaggacc aggaaggctc cccaccagaa acgagcctgc    1080
cttacaagtg ggtggtggag gcagctaacc tcctcatccc cgctgtgggt tctagcctct    1140
ctgaagccct ggacttgatc gagtcggacc ctgatgcttg gtgtgacctg agtaaatttg    1200
acctccctga ggaaccatct gcagaggaca gtatcaacaa cagcctagtg cagctgcaag    1260
cgtcacatca gcagcaagtc ctgccacccc gccagccttc cgccctggtg cccagtgtga    1320
ccgagtaccg cctggatggc cacaccatct cagacctgag ccggagcagc cggggcgagc    1380
tgatccccat ctcccccagc actgaagtcg ggggctctgg cattggcaca ccgccctctg    1440
tgctcaagcg gcagaggaag aggcgtgtgg ctctgtcccc tgtcactgag aatagcacca    1500
gtctgtcctt cctggattcc tgtaacagcc tcacgcccaa gagcacacct gttaagaccc    1560
tgccttctc gccctcccag tttctgaact tctggaacaa acaggacaca ttggagctgg    1620
agagccctc gctgacatcc accccagtgt gcagccagaa ggtggtggtc accacaccac    1680
tgcaccggga caagacaccc ctgcaccaga acatgctgc gtttgtaacc ccagatcaga    1740
agtactccat ggacaacact ccccacacgc caaccccgtt caagaacgcc ctggagaagt    1800
acggacccct gaagcccctg ccacagaccc cgcacctgga ggaggacttg aaggaggtgc    1860
tgcgttctga ggctggcatc gaactcatca tcgaggacga catcaggccc gagaagcaga    1920
agaggaagcc tgggctgcgg cggagcccca tcaagaaagt ccggaagtct ctggctcttg    1980
acattgtgga tgaggatgtg aagctgatga tgtccacact gcccaagtct ctatccttgc    2040
cgacaactgc cccttcaaac tcttccagcc tcaccctgtc aggtatcaaa gaagacaaca    2100
gcttgctcaa ccagggcttc ttgcaggcca gccccgagaa ggcagcagtg cccagaagc     2160
cccgaagcca cttcacgaca cctgccccta gtccagtgc ctggaagacg gtggcctgcg    2220
gggggaccag ggaccagctt ttcatgcagg agaaagcccg gcagtcctg ggccgcctga    2280
agcccagcca cacatctcgg accctcatct gtcctgagg tgttgagggt gtcacgagcc    2340
cattctcatg tttacagggg ttgtggggc agagggggtc tgtgaatctg agagtcattc     2400
aggtgacctc ctgcagggag ccttctgcca ccagcccctc cccagactct caggtggagg    2460
caacagggcc atgtgctgcc ctgttgccga gcccagctgt gggcggctcc tggtgctaac    2520
aacaaagttc cacttccagg tctgcctggt tccctcccca aggccacagg gagctccgtc    2580
agcttctccc aagcccacgt caggcctggc ctcatctcag accctgctta ggatggggga    2640
tgtggccagg ggtgctcctg tgctcaccct ctcttggtgc attttttgg aagaataaaa    2700
ttgcctctct cttaaaaaaa aaaaaaaaa a                                    2731
```

<210> SEQ ID NO 20
<211> LENGTH: 700
<212> TYPE: PRT
<213> ORGANISM: Homo sapiens

<400> SEQUENCE: 20

```
Met Ser Arg Arg Thr Arg Cys Glu Asp Leu Asp Glu Leu His Tyr Gln
 1               5                  10                  15
```

```
Asp Thr Asp Ser Asp Val Pro Glu Gln Arg Asp Ser Lys Cys Lys Val
             20                  25                  30

Lys Trp Thr His Glu Glu Asp Glu Gln Leu Arg Ala Leu Val Arg Gln
         35                  40                  45

Phe Gly Gln Gln Asp Trp Lys Phe Leu Ala Ser His Phe Pro Asn Arg
     50                  55                  60

Thr Asp Gln Gln Cys Gln Tyr Arg Trp Leu Arg Val Leu Asn Pro Asp
65                  70                  75                  80

Leu Val Lys Gly Pro Trp Thr Lys Glu Asp Gln Lys Val Ile Glu
                 85                  90                  95

Leu Val Lys Lys Tyr Gly Thr Lys Gln Trp Thr Leu Ile Ala Lys His
             100                 105                 110

Leu Lys Gly Arg Leu Gly Lys Gln Cys Arg Glu Arg Trp His Asn His
         115                 120                 125

Leu Asn Pro Glu Val Lys Lys Ser Cys Trp Thr Glu Glu Glu Asp Arg
    130                 135                 140

Ile Ile Cys Glu Ala His Lys Val Leu Gly Asn Arg Trp Ala Glu Ile
145                 150                 155                 160

Ala Lys Met Leu Pro Gly Arg Thr Asp Asn Ala Val Lys Asn His Trp
                165                 170                 175

Asn Ser Thr Ile Lys Arg Lys Val Asp Thr Gly Gly Phe Leu Ser Glu
            180                 185                 190

Ser Lys Asp Cys Lys Pro Pro Val Tyr Leu Leu Leu Glu Leu Glu Asp
        195                 200                 205

Lys Asp Gly Leu Gln Ser Ala Gln Pro Thr Glu Gly Gln Gly Ser Leu
    210                 215                 220

Leu Thr Asn Trp Pro Ser Val Pro Pro Thr Ile Lys Glu Glu Glu Asn
225                 230                 235                 240

Ser Glu Glu Glu Leu Ala Ala Thr Thr Ser Lys Glu Gln Glu Pro
                245                 250                 255

Ile Gly Thr Asp Leu Asp Ala Val Arg Thr Pro Glu Pro Leu Glu Glu
            260                 265                 270

Phe Pro Lys Arg Glu Asp Gln Glu Gly Ser Pro Pro Glu Thr Ser Leu
        275                 280                 285

Pro Tyr Lys Trp Val Val Glu Ala Ala Asn Leu Leu Ile Pro Ala Val
    290                 295                 300

Gly Ser Ser Leu Ser Glu Ala Leu Asp Leu Ile Glu Ser Asp Pro Asp
305                 310                 315                 320

Ala Trp Cys Asp Leu Ser Lys Phe Asp Leu Pro Glu Glu Pro Ser Ala
                325                 330                 335

Glu Asp Ser Ile Asn Asn Ser Leu Val Gln Leu Gln Ala Ser His Gln
            340                 345                 350

Gln Gln Val Leu Pro Pro Arg Gln Pro Ser Ala Leu Val Pro Ser Val
        355                 360                 365

Thr Glu Tyr Arg Leu Asp Gly His Thr Ile Ser Asp Leu Ser Arg Ser
    370                 375                 380

Ser Arg Gly Glu Leu Ile Pro Ile Ser Pro Ser Thr Glu Val Gly Gly
385                 390                 395                 400

Ser Gly Ile Gly Thr Pro Pro Ser Val Leu Lys Arg Gln Arg Lys Arg
                405                 410                 415

Arg Val Ala Leu Ser Pro Val Thr Glu Asn Ser Thr Ser Leu Ser Phe
            420                 425                 430
```

```
Leu Asp Ser Cys Asn Ser Leu Thr Pro Lys Ser Thr Pro Val Lys Thr
        435                 440                 445

Leu Pro Phe Ser Pro Ser Gln Phe Leu Asn Phe Trp Asn Lys Gln Asp
    450                 455                 460

Thr Leu Glu Leu Glu Ser Pro Ser Leu Thr Ser Thr Pro Val Cys Ser
465                 470                 475                 480

Gln Lys Val Val Thr Thr Pro Leu His Arg Asp Lys Thr Pro Leu
                485                 490                 495

His Gln Lys His Ala Ala Phe Val Thr Pro Asp Gln Lys Tyr Ser Met
            500                 505                 510

Asp Asn Thr Pro His Thr Pro Thr Pro Phe Lys Asn Ala Leu Glu Lys
        515                 520                 525

Tyr Gly Pro Leu Lys Pro Leu Pro Gln Thr Pro His Leu Glu Asp
    530                 535                 540

Leu Lys Glu Val Leu Arg Ser Glu Ala Gly Ile Glu Leu Ile Ile Glu
545                 550                 555                 560

Asp Asp Ile Arg Pro Glu Lys Gln Lys Arg Lys Pro Gly Leu Arg Arg
                565                 570                 575

Ser Pro Ile Lys Lys Val Arg Lys Ser Leu Ala Leu Asp Ile Val Asp
            580                 585                 590

Glu Asp Val Lys Leu Met Met Ser Thr Leu Pro Lys Ser Leu Ser Leu
        595                 600                 605

Pro Thr Thr Ala Pro Ser Asn Ser Ser Ser Leu Thr Leu Ser Gly Ile
    610                 615                 620

Lys Glu Asp Asn Ser Leu Leu Asn Gln Gly Phe Leu Gln Ala Lys Pro
625                 630                 635                 640

Glu Lys Ala Ala Val Ala Gln Lys Pro Arg Ser His Phe Thr Thr Pro
                645                 650                 655

Ala Pro Met Ser Ser Ala Trp Lys Thr Val Ala Cys Gly Gly Thr Arg
            660                 665                 670

Asp Gln Leu Phe Met Gln Glu Lys Ala Arg Gln Leu Leu Gly Arg Leu
        675                 680                 685

Lys Pro Ser His Thr Ser Arg Thr Leu Ile Leu Ser
    690                 695                 700

<210> SEQ ID NO 21
<211> LENGTH: 3145
<212> TYPE: DNA
<213> ORGANISM: Homo sapiens

<400> SEQUENCE: 21
ggcgggaaac agcttagtgg gtgtggggtc gcgcattttc ttcaaccagg aggtgaggag      60
gtttcgacat ggcggtgcag ccgaaggaga cgctgcagtt ggagagcgcg gccgaggtcg     120
gcttcgtgcg cttcttttca ggcatgccgg agaagccgac caccacagtg cgccttttcg     180 accgggcga cttctatacg cgcacggcg aggacgcgct gctggccgcc cgggaggtgt       240
tcaagaccca gggggtgatc aagtacatgg ggccggcagg agcaaagaat ctgcagagtg     300
ttgtgcttag taaaatgaat tttgaatctt ttgtaaaaga tcttcttctg gttcgtcagt     360
atagagttga agtttataag aatagagctg gaaataaggc atccaaggag aatgattggt     420
atttggcata taaggcttct cctggcaatc tctctcagtt tgaagacatt ctctttggta     480
acaatgatat gtcagcttcc attggtgttg tgggtgttaa aatgtccgca gttgatggcc     540
agagacaggt tggagtttgg tatgtggatt ccatacagag gaaactagga ctgtgtgaat     600
```

```
tccctgataa tgatcagttc tccaatcttg aggctctcct catccagatt ggaccaaagg     660
aatgtgtttt acccggagga gagactgctg gagacatggg gaaactgaga cagataattc    720
aaagaggagg aattctgatc acagaaagaa aaaaagctga cttttccaca aaagacattt    780
atcaggacct caaccggttg ttgaaaggca aaaagggaga gcagatgaat agtgctgtat    840
tgccagaaat ggagaatcag gttgcagttt catcactgtc tgcggtaatc aagttttag    900 aactcttatc agatgattcc aactttggac agtttgaact gactacttttt gacttcagcc    960 agtatatgaa attggatatt gcagcagtca gagcccttaa cctttttcag ggttctgttg   1020
aagataccac tggctctcag tctctggctg ccttgctgaa taagtgtaaa accccctcaag   1080 gacaaagact tgttaaccag tggattaagc agcctctcat ggataagaac agaatagagg   1140
agagattgaa tttagtggaa gcttttgtag aagatgcaga attgaggcag actttacaag   1200
aagatttact tcgtcgattc ccagatctta accgacttgc caagaagttt caaagacaag   1260
cagcaaactt acaagattgt taccgactct atcagggtat aaatcaacta cctaatgtta   1320
tacaggctct ggaaaaacat gaaggaaaac accagaaatt attgttggca gtttttgtga   1380
ctcctcttac tgatcttcgt tctgacttct ccaagtttca ggaaatgata gaaacaactt   1440
tagatatgga tcaggtggaa aaccatgaat tccttgtaaa accttcattt gatcctaatc   1500
tcagtgaatt aagagaaata atgaatgact ggaaaagaa gatgcagtca acattaataa   1560
gtgcagccag agatcttggc ttggaccctg gcaaacagat taaactggat tccagtgcac   1620
agtttggata ttactttcgt gtaacctgta aggaagaaaa agtccttcgt aacaataaaa   1680
actttagtac tgtagatatc cagaagaatg gtgttaaatt taccaacagc aaattgactt   1740
ctttaaatga gagtatacc aaaaataaaa cagaatatga gaagcccag gatgccattg   1800 ttaaagaaat tgtcaatatt tcttcaggct atgtagaacc aatgcagaca ctcaatgatg   1860
tgttagctca gctagatgct gttgtcagct ttgctcacgt gtcaaatgga gcacctgttc   1920
catatgtacg accagccatt ttggagaaag gacaaggaag aattatatta aaagcatcca   1980
ggcatgcttg tgttgaagtt caagatgaaa ttgcatttat tcctaatgac gtatacttttg   2040 aaaaagataa acagatgttc cacatcatta ctggccccaa tatgggaggt aaatcaacat   2100
atattcgaca aactggggtg atagtactca tggcccaaat tggtgttttt gtgccatgtg   2160
agtcagcaga agtgtccatt gtggactgca tcttagcccg agtaggggct ggtgacagtc   2220
aattgaaagg agtctccacg ttcatggctg aaatgttgga aactgcttct atcctcaggt   2280
ctgcaaccaa agattcatta ataatcatag atgaattggg aagaggaact tctacctacg   2340
atggatttgg gttagcatgg gctatatcag aatacattgc aacaaagatt ggtgcttttt   2400
gcatgtttgc aacccatttt catgaactta ctgccttggc caatcagata ccaactgtta   2460
ataatctaca tgtcacagca ctcaccactg aagagacctt aactatgctt tatcaggtga   2520
agaaaggtgt ctgtgatcaa gttttggga ttcatgttgc agagcttgct aatttcccta   2580
agcatgtaat agagtgtgct aaacagaaag ccctggaact tgaggagttt cagtatattg   2640
gagaatcgca aggatatgat atcatggaac cagcagcaaa gaagtgctat ctggaaagag   2700
agcaaggtga aaaattatt caggagttcc tgtccaaggt gaaacaaatg cccttttactg   2760 aaatgtcaga agaaacatc acaataaagt taaacagct aaaagctgaa gtaatagcaa   2820
agaataatag ctttgtaaat gaaatcattt cacgaataaa agttactacg tgaaaatcc   2880 cagtaatgga atgaaggtaa tattgataag ctattgtctg taatagtttt atattgtttt   2940
atattaaccc ttttttccata gtgttaactg tcagtgccca tgggctatca acttaataag   3000
```

```
atatttagta atattttact ttgaggacat tttcaaagat ttttattttg aaaaatgaga    3060
gctgtaactg aggactgttt gcaattgaca taggcaataa taagtgatgt gctgaatttt    3120
ataaataaaa tcatgtagtt tgtgg                                         3145
```

<210> SEQ ID NO 22
<211> LENGTH: 934
<212> TYPE: PRT
<213> ORGANISM: Homo sapiens

<400> SEQUENCE: 22

```
Met Ala Val Gln Pro Lys Glu Thr Leu Gln Leu Glu Ser Ala Ala Glu
  1               5                  10                  15

Val Gly Phe Val Arg Phe Phe Gln Gly Met Pro Glu Lys Pro Thr Thr
             20                  25                  30

Thr Val Arg Leu Phe Asp Arg Gly Asp Phe Tyr Thr Ala His Gly Glu
         35                  40                  45

Asp Ala Leu Leu Ala Ala Arg Glu Val Phe Lys Thr Gln Gly Val Ile
     50                  55                  60

Lys Tyr Met Gly Pro Ala Gly Ala Lys Asn Leu Gln Ser Val Val Leu
 65                  70                  75                  80

Ser Lys Met Asn Phe Glu Ser Phe Val Lys Asp Leu Leu Leu Val Arg
                 85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
        195                 200                 205

Asp Met Gly Lys Leu Arg Gln Ile Ile Gln Arg Gly Gly Ile Leu Ile
    210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
        275                 280                 285

Phe Glu Leu Thr Thr Phe Asp Phe Ser Gln Tyr Met Lys Leu Asp Ile
    290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
```

-continued

```
                 340                 345                 350
Lys Asn Arg Ile Glu Glu Arg Leu Asn Leu Val Glu Ala Phe Val Glu
                 355                 360                 365
Asp Ala Glu Leu Arg Gln Thr Leu Gln Glu Asp Leu Leu Arg Arg Phe
                 370                 375                 380
Pro Asp Leu Asn Arg Leu Ala Lys Lys Phe Gln Arg Gln Ala Ala Asn
385                 390                 395                 400
Leu Gln Asp Cys Tyr Arg Leu Tyr Gln Gly Ile Asn Gln Leu Pro Asn
                 405                 410                 415
Val Ile Gln Ala Leu Glu Lys His Glu Gly Lys His Gln Lys Leu Leu
                 420                 425                 430
Leu Ala Val Phe Val Thr Pro Leu Thr Asp Leu Arg Ser Asp Phe Ser
                 435                 440                 445
Lys Phe Gln Glu Met Ile Glu Thr Thr Leu Asp Met Asp Gln Val Glu
                 450                 455                 460
Asn His Glu Phe Leu Val Lys Pro Ser Phe Asp Pro Asn Leu Ser Glu
465                 470                 475                 480
Leu Arg Glu Ile Met Asn Asp Leu Glu Lys Lys Met Gln Ser Thr Leu
                 485                 490                 495
Ile Ser Ala Ala Arg Asp Leu Gly Leu Asp Pro Gly Lys Gln Ile Lys
                 500                 505                 510
Leu Asp Ser Ser Ala Gln Phe Gly Tyr Tyr Phe Arg Val Thr Cys Lys
                 515                 520                 525
Glu Glu Lys Val Leu Arg Asn Asn Lys Asn Phe Ser Thr Val Asp Ile
                 530                 535                 540
Gln Lys Asn Gly Val Lys Phe Thr Asn Ser Lys Leu Thr Ser Leu Asn
545                 550                 555                 560
Glu Glu Tyr Thr Lys Asn Lys Thr Glu Tyr Glu Glu Ala Gln Asp Ala
                 565                 570                 575
Ile Val Lys Glu Ile Val Asn Ile Ser Ser Gly Tyr Val Glu Pro Met
                 580                 585                 590
Gln Thr Leu Asn Asp Val Leu Ala Gln Leu Asp Ala Val Val Ser Phe
                 595                 600                 605
Ala His Val Ser Asn Gly Ala Pro Val Pro Tyr Val Arg Pro Ala Ile
                 610                 615                 620
Leu Glu Lys Gly Gln Gly Arg Ile Ile Leu Lys Ala Ser Arg His Ala
625                 630                 635                 640
Cys Val Glu Val Gln Asp Glu Ile Ala Phe Ile Pro Asn Asp Val Tyr
                 645                 650                 655
Phe Glu Lys Asp Lys Gln Met Phe His Ile Ile Thr Gly Pro Asn Met
                 660                 665                 670
Gly Gly Lys Ser Thr Tyr Ile Arg Gln Thr Gly Val Ile Val Leu Met
                 675                 680                 685
Ala Gln Ile Gly Cys Phe Val Pro Cys Glu Ser Ala Glu Val Ser Ile
                 690                 695                 700
Val Asp Cys Ile Leu Ala Arg Val Gly Ala Gly Asp Ser Gln Leu Lys
705                 710                 715                 720
Gly Val Ser Thr Phe Met Ala Glu Met Leu Glu Thr Ala Ser Ile Leu
                 725                 730                 735
Arg Ser Ala Thr Lys Asp Ser Leu Ile Ile Ile Asp Glu Leu Gly Arg
                 740                 745                 750
Gly Thr Ser Thr Tyr Asp Gly Phe Gly Leu Ala Trp Ala Ile Ser Glu
                 755                 760                 765
```

```
Tyr Ile Ala Thr Lys Ile Gly Ala Phe Cys Met Phe Ala Thr His Phe
    770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
        835                 840                 845

Leu Glu Leu Glu Glu Phe Gln Tyr Ile Gly Glu Ser Gln Gly Tyr Asp
    850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
                900                 905                 910

Ala Glu Val Ile Ala Lys Asn Asn Ser Phe Val Asn Glu Ile Ile Ser
        915                 920                 925

Arg Ile Lys Val Thr Thr
    930

<210> SEQ ID NO 23
<211> LENGTH: 2530
<212> TYPE: DNA
<213> ORGANISM: Homo sapiens

<400> SEQUENCE: 23
cagcttccct gtggtttccc gaggcttcct tgcttcccgc tctgcgagga gcctttcatc      60
cgaaggcggg acgatgccgg ataatcggca gccgaggaac cggcagccga ggatccgctc     120
cgggaacgag cctcgttccg cgcccgccat ggaaccggat ggtcgcggtg cctgggccca     180
cagtcgcgcc gcgctcgacc gcctggagaa gctgctgcgc tgctcgcgtt gtactaacat     240
tctgagagag cctgtgtgtt taggaggatg tgagcacatc ttctgtagta attgtgtaag     300
tgactgcatt ggaactggat gtccagtgtg ttacaccccg gcctggatac aagacttgaa     360
gataaataga caactggaca gcatgattca actttgtagt aagcttcgaa atttgctaca     420
tgacaatgag ctgtcagatt tgaaagaaga taaacctagg aaaagtttgt ttaatgatgc     480
aggaaacaag aagaattcaa ttaaaatgtg gtttagccct cgaagtaaga agtcagata     540 tgttgtgagt aaagcttcag tgcaaaccca gcctgcaata aaaaagatg caagtgctca     600 gcaagactca tatgaatttg tttccccaag tcctcctgca gatgtttctg agagggctaa     660
aaaggcttct gcaagatctg gaaaaaagca aaaaagaaa actttagctg aaatcaacca     720
aaaatggaat ttagaggcag aaaaagaaga tggtgaattt gactccaaag aggaatctaa     780
gcaaaagctg gtatccttct gtagccaacc atctgttatc tccagtcctc agataaatgg     840
tgaaatagac ttactagcaa gtggctcctt gacagaatct gaatgttttg aagtttaac     900 tgaagtctct ttaccattgg ctgagcaaat agagtctcca gacactaaga gcaggaatga     960
agtagtgact cctgagaagg tctgcaaaaa ttatcttaca tctaagaaat ctttgccatt    1020
agaaaataat ggaaaacgtg gccatcacaa tagactttcc agtcccattt ctaagagatg    1080
tagaaccagc attctgagca ccagtggaga ttttgttaag caaaccgtgc cctcagaaaa    1140
```

```
tataccattg cctgaatgtt cttcaccacc ttcatgcaaa cgtaaagttg gtggtacatc    1200
agggaggaaa aacagtaaca tgtccgatga attcattagt ctttcaccag gtacaccacc    1260
ttctacatta agtagttcaa gttacaggca agtgatgtct agtccctcag caatgaagct    1320
gttgcccaat atggctgtga aaagaaatca tagaggagag actttgctcc atattgcttc    1380
tattaagggc gacatacctt ctgttgaata ccttttacaa aatggaagtg atccaaatgt    1440
taaagaccat gctggatgga caccattgca tgaagcttgc aatcatgggc acctgaaggt    1500
agtggaatta ttgctccagc ataaggcatt ggtgaacacc accgggtatc aaaatgactc    1560
accacttcac gatgcagcca agaatgggca cgtggatata gtcaagctgt actttccta    1620 tggagcctcc agaaatgctg ttaatatatt tggtctgcgg cctgtcgatt atacagatga    1680
tgaaagtatg aaatcgctat tgctgctacc agagaagaat gaatcatcct cagctagcca    1740
ctgctcagta atgaacactg ggcagcgtag ggatggacct cttgtactta taggcagtgg    1800
gctgtcttca gaacaacaga aaatgctcag tgagcttgca gtaattctta aggctaaaaa    1860
atatactgag tttgacagta cagtaactca tgttgttgtt cctggtgatg cagttcaaag    1920
taccttgaag tgtatgcttg ggattctcaa tggatgctgg attctaaaat ttgaatgggt    1980
aaaagcatgt ctacgaagaa aagtatgtga acaggaagaa aagtatgaaa ttcctgaagg    2040
tccacgcaga agcaggctca acagagaaca gctgttgcca aagctgtttg atggatgcta    2100
cttctatttg tggggaacct tcaaacacca tccaaaggac aaccttatta agctcgtcac    2160
tgcaggtggg ggccagatcc tcagtagaaa gcccaagcca gacagtgacg tgactcagac    2220
catcaataca gtcgcatacc atgcgagacc cgattctgat cagcgcttct gcacacagta    2280
tatcatctat gaagatttgt gtaattatca cccagagagg gttcggcagg caaagtctg    2340 gaaggctcct tcgagctggt ttatagactg tgtgatgtcc tttgagttgc ttcctcttga    2400
cagctgaata ttataccaga tgaacatttc aaattgaatt tgcacggttt gtgagagccc    2460
agtcattgta ctgttttttaa tgttcacatt tttacaaata ggtagagtca ttcatatttg    2520
tctttgaatc                                                            2530
```

<210> SEQ ID NO 24
<211> LENGTH: 777
<212> TYPE: PRT
<213> ORGANISM: Homo sapiens

<400> SEQUENCE: 24

```
Met Pro Asp Asn Arg Gln Pro Arg Asn Arg Gln Pro Arg Ile Arg Ser
 1               5                  10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Thr Asn Ile Leu Arg Glu Pro Val Cys Leu Gly
    50                  55                  60

Gly Cys Glu His Ile Phe Cys Ser Asn Cys Val Ser Asp Cys Ile Gly
65                  70                  75                  80

Thr Gly Cys Pro Val Cys Tyr Thr Pro Ala Trp Ile Gln Asp Leu Lys
                85                  90                  95

Ile Asn Arg Gln Leu Asp Ser Met Ile Gln Leu Cys Ser Lys Leu Arg
            100                 105                 110

Asn Leu Leu His Asp Asn Glu Leu Ser Asp Leu Lys Glu Asp Lys Pro
```

-continued

```
            115                 120                 125
Arg Lys Ser Leu Phe Asn Asp Ala Gly Asn Lys Asn Ser Ile Lys
        130                 135                 140
Met Trp Phe Ser Pro Arg Ser Lys Lys Val Arg Tyr Val Ser Lys
145                 150                 155                 160
Ala Ser Val Gln Thr Gln Pro Ala Ile Lys Lys Asp Ala Ser Ala Gln
                165                 170                 175
Gln Asp Ser Tyr Glu Phe Val Ser Pro Ser Pro Ala Asp Val Ser
            180                 185                 190
Glu Arg Ala Lys Lys Ala Ser Ala Arg Ser Gly Lys Lys Gln Lys Lys
                195                 200                 205
Lys Thr Leu Ala Glu Ile Asn Gln Lys Trp Asn Leu Glu Ala Glu Lys
        210                 215                 220
Glu Asp Gly Glu Phe Asp Ser Lys Glu Glu Ser Lys Gln Lys Leu Val
225                 230                 235                 240
Ser Phe Cys Ser Gln Pro Ser Val Ile Ser Ser Pro Gln Ile Asn Gly
                245                 250                 255
Glu Ile Asp Leu Leu Ala Ser Gly Ser Leu Thr Glu Ser Glu Cys Phe
            260                 265                 270
Gly Ser Leu Thr Glu Val Ser Leu Pro Leu Ala Glu Gln Ile Glu Ser
        275                 280                 285
Pro Asp Thr Lys Ser Arg Asn Glu Val Val Thr Pro Glu Lys Val Cys
        290                 295                 300
Lys Asn Tyr Leu Thr Ser Lys Lys Ser Leu Pro Leu Glu Asn Asn Gly
305                 310                 315                 320
Lys Arg Gly His His Asn Arg Leu Ser Ser Pro Ile Ser Lys Arg Cys
                325                 330                 335
Arg Thr Ser Ile Leu Ser Thr Ser Gly Asp Phe Val Lys Gln Thr Val
                340                 345                 350
Pro Ser Glu Asn Ile Pro Leu Pro Glu Cys Ser Ser Pro Pro Ser Cys
            355                 360                 365
Lys Arg Lys Val Gly Gly Thr Ser Gly Arg Lys Asn Ser Asn Met Ser
        370                 375                 380
Asp Glu Phe Ile Ser Leu Ser Pro Gly Thr Pro Pro Ser Thr Leu Ser
385                 390                 395                 400
Ser Ser Ser Tyr Arg Gln Val Met Ser Ser Pro Ser Ala Met Lys Leu
                405                 410                 415
Leu Pro Asn Met Ala Val Lys Arg Asn His Arg Gly Glu Thr Leu Leu
            420                 425                 430
His Ile Ala Ser Ile Lys Gly Asp Ile Pro Ser Val Glu Tyr Leu Leu
        435                 440                 445
Gln Asn Gly Ser Asp Pro Asn Val Lys Asp His Ala Gly Trp Thr Pro
    450                 455                 460
Leu His Glu Ala Cys Asn His Gly His Leu Lys Val Val Glu Leu Leu
465                 470                 475                 480
Leu Gln His Lys Ala Leu Val Asn Thr Thr Gly Tyr Gln Asn Asp Ser
                485                 490                 495
Pro Leu His Asp Ala Ala Lys Asn Gly His Val Asp Ile Val Lys Leu
            500                 505                 510
Leu Leu Ser Tyr Gly Ala Ser Arg Asn Ala Val Asn Ile Phe Gly Leu
        515                 520                 525
Arg Pro Val Asp Tyr Thr Asp Asp Glu Ser Met Lys Ser Leu Leu Leu
    530                 535                 540
```

```
Leu Pro Glu Lys Asn Glu Ser Ser Ala Ser His Cys Ser Val Met
545                 550                 555                 560

Asn Thr Gly Gln Arg Arg Asp Gly Pro Leu Val Leu Ile Gly Ser Gly
                565                 570                 575

Leu Ser Ser Glu Gln Gln Lys Met Leu Ser Glu Leu Ala Val Ile Leu
            580                 585                 590

Lys Ala Lys Lys Tyr Thr Glu Phe Asp Ser Thr Val Thr His Val Val
        595                 600                 605

Val Pro Gly Asp Ala Val Gln Ser Thr Leu Lys Cys Met Leu Gly Ile
    610                 615                 620

Leu Asn Gly Cys Trp Ile Leu Lys Phe Glu Trp Val Lys Ala Cys Leu
625                 630                 635                 640

Arg Arg Lys Val Cys Glu Gln Glu Glu Lys Tyr Glu Ile Pro Glu Gly
                645                 650                 655

Pro Arg Arg Ser Arg Leu Asn Arg Glu Gln Leu Leu Pro Lys Leu Phe
            660                 665                 670

Asp Gly Cys Tyr Phe Tyr Leu Trp Gly Thr Phe Lys His His Pro Lys
        675                 680                 685

Asp Asn Leu Ile Lys Leu Val Thr Ala Gly Gly Gly Gln Ile Leu Ser
    690                 695                 700

Arg Lys Pro Lys Pro Asp Ser Asp Val Thr Gln Thr Ile Asn Thr Val
705                 710                 715                 720

Ala Tyr His Ala Arg Pro Asp Ser Asp Gln Arg Phe Cys Thr Gln Tyr
                725                 730                 735

Ile Ile Tyr Glu Asp Leu Cys Asn Tyr His Pro Glu Arg Val Arg Gln
            740                 745                 750

Gly Lys Val Trp Lys Ala Pro Ser Ser Trp Phe Ile Asp Cys Val Met
        755                 760                 765

Ser Phe Glu Leu Leu Pro Leu Asp Ser
    770                 775

<210> SEQ ID NO 25
<211> LENGTH: 2937
<212> TYPE: DNA
<213> ORGANISM: Homo sapiens

<400> SEQUENCE: 25
caatttcaga gtgggatatc agatctttag tgtgaagata catctacatt aaaccaggaa      60
tcactagaac tgacatttgg acaagaaaat ttggaaaatt ttaaaactgt gaaggttgat     120
catggaaatt aaagaggaag ggcatcaga agaagggcag cactttcttc ctacagccca     180
ggccaatgat cccgggact gtcagttcac aagtatccag aagactccaa atgaaccgca     240
gttggaattc atccttgcat gcaaggatct cgtggctcct gtccgtgatc gtaaactgaa     300
tacactggtg cagatctccg taatccaccc cgtggagcag agtctgacaa gatactccag     360
caccgaaatt gtggagggaa caagggaccc actgttttg actggtgtca cattcccatc     420
tgagtatccc atctatgagg agaccaaaat aaaactaaca gtctatgatg tcaaggataa     480
gtctcatgac accgttcgaa ccagtgtcct accagaacat aaggatcccc cgccagaagt     540
tggccgaagt ttcttgggct atgccagttt taaagtggga gagctgctga agtcaaagga     600
gcaattgctg gtcctgagcc tgagaacttc agatggtggc aaagtggttg caccataga     660 agtcagtgtc gtgaagatgg gggagattga ggatggggaa gccgaccaca tcaccacaga     720
tgtacaggga caaaagtgtg ccctggtatg tgaatgtaca gccccggaaa gtgtgagcgg     780
```

```
aaaagataac ttaccttttt tgaattcagt gttaaagaac ccagtatgta aattatatag    840
atttcccaca tctgacaata agtggatgcg aattcgagag cagatgtcag agagcattct    900
ttcctttcat attcctaagg aattgatttc ccttcacatt aaagaagatt tgtgcagaaa    960
ccaggagata aagaacttg gtgagctttc tccacattgg acaatctgc gaaaaatgt      1020
ccttacgcac tgtgatcaaa tggtaatat gttccaagac attctgacag aacttgccaa    1080
ggaaacaggg tcctctttca aatcaagcag cagcaaagga gagaaaacat tagaatttgt    1140
tccaataaat ctacatctgc aaagaatgca ggtacacagc cctcacttga agatgctct    1200
ctacgatgtc atcactgtgg gagccccagc tgcccatttt cagggattta agaatggtgg    1260
tcttcggaag ctactccata gatttgaaac agaaagaaga aataccggat accagtttat    1320
ttactattca cctgaaaaca cagccaaagc aaaggaagtt ctcagcaaca tcaatcaact    1380
acaacctctt atagcaaccc atgcagacct actgcttaat tctgcaagcc agcattctcc    1440
agacagcttg aagaattctt taaagatgct ttcagaaaaa acagagcttt ttgtacatgc    1500
cttcaaggat caacttgtca ggagtgctct tttagcactc tacactgcaa ggccaggagg    1560
cattcttaag aagccacccct ctcctaagag cagcacagag gagagcagtc cccaagacca    1620
acccccagtg atgagagggc aggactccat accacatcat tcagactatg atgaggaaga    1680
gtgggacagg gtgtgggcca atgtggggaa gagcctgaac tgcattattg ctatggtgga    1740
caaactgatt gaaagagatg gtggcagtga aggcagtggt ggcaacaatg atggagaaaa    1800
ggaaccttca ttaacagatg ccattccctc tcacccaaga gaggactggt atgaacagtt    1860
gtatcccctc atccttaccc tgaaggactg catgggagaa gtggtgaacc gagccaagca    1920
gtccctgaca tttgtgctcc ttcaggaact tgcgtacagc ttgccccagt gtctgatgct    1980
gacgctaaga agagacatcg tcttcagcca agcacttgct ggattggttt gtggttttat    2040
catcaaatta cagacaagtc tgtatgaccc aggcttccta cagcagcttc acacagtggg    2100
gttgatagta caatatgaag gattgttaag tacatacagc gatgaaattg gaatgttaga    2160
ggacatgccc gttggcattt ccgatttaaa gaaagttgca tttaaaataa ttgaagccaa    2220
atccaatgat gtattgccag ttataacagg aagacgagaa cattacgtgg tagaggtcaa    2280
gcttccagcc agaatgtttg agtcactacc tctacagatt aaagaaggac agttgcttca    2340
tgtgtatcca gtacttttta atgttggaat caatgaacag caaactctgg ctgaaaggtt    2400
tggagatgtc tctttgcaag aaagtattaa tcaggaaaac ttcgaacttc tacaagaata    2460
ttacaagata tttatggaaa agatgcctcc tgattatatt tcacattttc aggaacaaaa    2520
tgatttaaaa gcattgctag aaaatctcct tcaaaatatc caatccaaaa aagaaagaa    2580
tgtagaaatt atgtggctgg ctgcaacgat ttgccgcaaa ctgaatggta ttcgtttcac    2640
ctgttgtaaa agtgccaaag acaggacatc gatgtcagtg acacttgaac aatgctcaat    2700
cttgagagat gagcaccagt tacacaagga cttctttatc cgagcgctgg attgcatgag    2760
aagagaagga tgccgcatag agaatgtact gaagaatatc aaatgcagaa agtatgcttt    2820
caacatgcta cagctgatgg ctttccccaa gtactacaga cctccagagg ggacttatgg    2880
aaaagctgac acctaagttt accaacatgt taataaacag gaacacaaat acattttc     2937
```

<210> SEQ ID NO 26
<211> LENGTH: 924
<212> TYPE: PRT
<213> ORGANISM: Homo sapiens

<400> SEQUENCE: 26

```
Met Glu Ile Lys Glu Glu Gly Ala Ser Glu Glu Gly Gln His Phe Leu
 1               5                  10                  15

Pro Thr Ala Gln Ala Asn Asp Pro Gly Asp Cys Gln Phe Thr Ser Ile
            20                  25                  30

Gln Lys Thr Pro Asn Glu Pro Gln Leu Glu Phe Ile Leu Ala Cys Lys
        35                  40                  45

Asp Leu Val Ala Pro Val Arg Asp Arg Lys Leu Asn Thr Leu Val Gln
50                  55                  60

Ile Ser Val Ile His Pro Val Glu Gln Ser Leu Thr Arg Tyr Ser Ser
65                  70                  75                  80

Thr Glu Ile Val Glu Gly Thr Arg Asp Pro Leu Phe Leu Thr Gly Val
                85                  90                  95

Thr Phe Pro Ser Glu Tyr Pro Ile Tyr Glu Glu Thr Lys Ile Lys Leu
            100                 105                 110

Thr Val Tyr Asp Val Lys Asp Lys Ser His Asp Thr Val Arg Thr Ser
        115                 120                 125

Val Leu Pro Glu His Lys Asp Pro Pro Glu Val Gly Arg Ser Phe
130                 135                 140

Leu Gly Tyr Ala Ser Phe Lys Val Gly Glu Leu Leu Lys Ser Lys Glu
145                 150                 155                 160

Gln Leu Leu Val Leu Ser Leu Arg Thr Ser Asp Gly Lys Val Val
                165                 170                 175

Gly Thr Ile Glu Val Ser Val Val Lys Met Gly Glu Ile Glu Asp Gly
            180                 185                 190

Glu Ala Asp His Ile Thr Thr Asp Val Gln Gly Gln Lys Cys Ala Leu
        195                 200                 205

Val Cys Glu Cys Thr Ala Pro Glu Ser Val Ser Gly Lys Asp Asn Leu
210                 215                 220

Pro Phe Leu Asn Ser Val Leu Lys Asn Pro Val Cys Lys Leu Tyr Arg
225                 230                 235                 240

Phe Pro Thr Ser Asp Asn Lys Trp Met Arg Ile Arg Glu Gln Met Ser
                245                 250                 255

Glu Ser Ile Leu Ser Phe His Ile Pro Lys Glu Leu Ile Ser Leu His
            260                 265                 270

Ile Lys Glu Asp Leu Cys Arg Asn Gln Glu Ile Lys Glu Leu Gly Glu
        275                 280                 285

Leu Ser Pro His Trp Asp Asn Leu Arg Lys Asn Val Leu Thr His Cys
290                 295                 300

Asp Gln Met Val Asn Met Phe Gln Asp Ile Leu Thr Glu Leu Ala Lys
305                 310                 315                 320

Glu Thr Gly Ser Ser Phe Lys Ser Ser Ser Lys Gly Glu Lys Thr
                325                 330                 335

Leu Glu Phe Val Pro Ile Asn Leu His Leu Gln Arg Met Gln Val His
            340                 345                 350

Ser Pro His Leu Lys Asp Ala Leu Tyr Asp Val Ile Thr Val Gly Ala
        355                 360                 365

Pro Ala Ala His Phe Gln Gly Phe Lys Asn Gly Gly Leu Arg Lys Leu
370                 375                 380

Leu His Arg Phe Glu Thr Glu Arg Arg Asn Thr Gly Tyr Gln Phe Ile
385                 390                 395                 400

Tyr Tyr Ser Pro Glu Asn Thr Ala Lys Ala Lys Glu Val Leu Ser Asn
                405                 410                 415
```

```
Ile Asn Gln Leu Gln Pro Leu Ile Ala Thr His Ala Asp Leu Leu Leu
            420                 425                 430

Asn Ser Ala Ser Gln His Ser Pro Asp Ser Leu Lys Asn Ser Leu Lys
        435                 440                 445

Met Leu Ser Glu Lys Thr Glu Leu Phe Val His Ala Phe Lys Asp Gln
    450                 455                 460

Leu Val Arg Ser Ala Leu Leu Ala Leu Tyr Thr Ala Arg Pro Gly Gly
465                 470                 475                 480

Ile Leu Lys Lys Pro Pro Ser Pro Lys Ser Ser Thr Glu Glu Ser Ser
                485                 490                 495

Pro Gln Asp Gln Pro Pro Val Met Arg Gly Gln Asp Ser Ile Pro His
            500                 505                 510

His Ser Asp Tyr Asp Glu Glu Trp Asp Arg Val Trp Ala Asn Val
        515                 520                 525

Gly Lys Ser Leu Asn Cys Ile Ile Ala Met Val Asp Lys Leu Ile Glu
530                 535                 540

Arg Asp Gly Gly Ser Glu Gly Ser Gly Gly Asn Asn Asp Gly Glu Lys
545                 550                 555                 560

Glu Pro Ser Leu Thr Asp Ala Ile Pro Ser His Pro Arg Glu Asp Trp
                565                 570                 575

Tyr Glu Gln Leu Tyr Pro Leu Ile Leu Thr Leu Lys Asp Cys Met Gly
            580                 585                 590

Glu Val Val Asn Arg Ala Lys Gln Ser Leu Thr Phe Val Leu Leu Gln
        595                 600                 605

Glu Leu Ala Tyr Ser Leu Pro Gln Cys Leu Met Leu Thr Leu Arg Arg
    610                 615                 620

Asp Ile Val Phe Ser Gln Ala Leu Ala Gly Leu Val Cys Gly Phe Ile
625                 630                 635                 640

Ile Lys Leu Gln Thr Ser Leu Tyr Asp Pro Gly Phe Leu Gln Gln Leu
                645                 650                 655

His Thr Val Gly Leu Ile Val Gln Tyr Glu Gly Leu Leu Ser Thr Tyr
            660                 665                 670

Ser Asp Glu Ile Gly Met Leu Glu Asp Met Pro Val Gly Ile Ser Asp
        675                 680                 685

Leu Lys Lys Val Ala Phe Lys Ile Ile Glu Ala Lys Ser Asn Asp Val
    690                 695                 700

Leu Pro Val Ile Thr Gly Arg Arg Glu His Tyr Val Val Glu Val Lys
705                 710                 715                 720

Leu Pro Ala Arg Met Phe Glu Ser Leu Pro Leu Gln Ile Lys Glu Gly
                725                 730                 735

Gln Leu Leu His Val Tyr Pro Val Leu Phe Asn Val Gly Ile Asn Glu
            740                 745                 750

Gln Gln Thr Leu Ala Glu Arg Phe Gly Asp Val Ser Leu Gln Glu Ser
        755                 760                 765

Ile Asn Gln Glu Asn Phe Glu Leu Leu Gln Glu Tyr Tyr Lys Ile Phe
    770                 775                 780

Met Glu Lys Met Pro Pro Asp Tyr Ile Ser His Phe Gln Glu Gln Asn
785                 790                 795                 800

Asp Leu Lys Ala Leu Leu Glu Asn Leu Gln Asn Ile Gln Ser Lys
                805                 810                 815

Lys Arg Lys Asn Val Glu Ile Met Trp Leu Ala Ala Thr Ile Cys Arg
            820                 825                 830
```

```
Lys Leu Asn Gly Ile Arg Phe Thr Cys Cys Lys Ser Ala Lys Asp Arg
            835                 840                 845

Thr Ser Met Ser Val Thr Leu Glu Gln Cys Ser Ile Leu Arg Asp Glu
        850                 855                 860

His Gln Leu His Lys Asp Phe Phe Ile Arg Ala Leu Asp Cys Met Arg
865                 870                 875                 880

Arg Glu Gly Cys Arg Ile Glu Asn Val Leu Lys Asn Ile Lys Cys Arg
                885                 890                 895

Lys Tyr Ala Phe Asn Met Leu Gln Leu Met Ala Phe Pro Lys Tyr Tyr
            900                 905                 910

Arg Pro Pro Glu Gly Thr Tyr Gly Lys Ala Asp Thr
            915                 920

<210> SEQ ID NO 27
<211> LENGTH: 1846
<212> TYPE: DNA
<213> ORGANISM: Homo sapiens

<400> SEQUENCE: 27
cctctctctc tctccctctc tctctccctc tctctctctc cctgtgtcgc ttaaacaaca     60
gtcctaactt tgtgtgttg caaatataaa aggcaagcca tgtgacagag ggacagaaga    120
acaaaagcat ttggaagtaa caggacctct ttctagctct cagaaaagtc tgagaagaaa    180
ggagccctgc gttcccctaa gctgtgcagc agatactgtg atgatggatt gcaagtgcaa    240
agagtaagac aaaactccag cacataaagg acaatgacaa ccagaaagct tcagcccgat    300
cctgcccttt ccttgaacgg gactggatcc taggaggtga agccatttcc aattttttgt    360
cctctgcctc cctctgctgt tcttctagag aagttttttcc ttacaacaat gagaaaacat    420
gtactagctg catccttttc tatgctctcc ctgctggtga taatgggaga tacagacagt    480
aaaacggaca gctcattcat aatggactcg gaccctcgac gctgcatgag gcaccactat    540
gtggattcta tcagtcaccc attgtacaag tgtagctcaa agatggtgct cctggccagg    600
tgcgaggggc actgcagcca ggcgtcacgc tccgagcctt tggtgtcgtt cagcactgtc    660
ctcaagcaac ccttccgttc ctcctgtcac tgctgccggc cccagacttc caagctgaag    720
gcactgcggc tgcgatgctc agggggcatg cgactcactg ccacctaccg gtacatcctc    780
tcctgtcact gcgaggaatg caattcctga ggcccgctgc tgtgtgtggc ttctggatgg    840
gacaactgta gaggcagttc gaccagccag ggaaagactg gcaagaaaag agttaaggca    900
aaaaaggatg caacaattct cccgggactc tgcatattct agtaataaag actctacatg    960
cttgttgaca gagagagata tctctgggaac ttctttgcag ttcccatctc ctttctctgg   1020
tacaatttct tttggttcat tttcagattc aggcattttc ccccttggct ctcaatgctg   1080
tttgggtttc caacaattca gcattagtgg gaaaaagtgg gccctcatac acaagcgtgt   1140
caggctgtca gtgtttggtg cacgctgggg aagaatttac tttggaaagt agaaaagccc   1200
agcttttcct gggacatctt ctgttattgt tgatgttttt ttttaccttg tcatttttggt   1260
ctaaggttgc cattgctgct aaaggttacc gatttcaaag tccagatacc aagcatgtgg   1320
atatgtttag ctacgtttac tcacagccag cgaactgaca ttaaaataac taacaaacag   1380
attcttttat gtgatgctgg aactcttgac agctataatt attattcaga aatgactttt   1440
tgaaagtaaa agcagcataa agaatttgtc acaggaaggc tgtctcagat aaattatggt   1500
aaaattttgt aagggagcag acttttaaag acttgcacaa atacggatcc tgcactgact   1560
ctggaaaagg catatatgta ctagtggcat ggagaatgca ccatactcat gcatgcaaat   1620
```

```
tagacaacca agtatgaatc tatttgtggg tgtgctatag ctttagcgtg tcacgggcat    1680
cattctctaa tatccacttg tccatgtgaa acatgttgcc aaaatggtgg cctggcttgt    1740
cttctgaacg tttggttcaa atgtgttttg gtcctggagg ctcaaatttt gagttattcc    1800
cacgttttga ataaaaaga gtatattcaa aaaaaaaaaa aaaaaa                     1846
```

<210> SEQ ID NO 28
<211> LENGTH: 133
<212> TYPE: PRT
<213> ORGANISM: Homo sapiens

<400> SEQUENCE: 28

```
Met Arg Lys His Val Leu Ala Ala Ser Phe Ser Met Leu Ser Leu Leu
 1               5                  10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130
```

<210> SEQ ID NO 29
<211> LENGTH: 1505
<212> TYPE: DNA
<213> ORGANISM: Homo sapiens

<400> SEQUENCE: 29

```
gaattccggg cgcctggagc cacacaggga tccggagcct gggggaaaag cggcgcggga      60
gccggcaccc accgctggag gggcggcgac ggcggccgta gcgacctcgg gaggcaagcg     120
gagccgccat ggccgagttc ccgtcgaaag ttagcacgcg gaccagcagt cctgcgcagg     180
gcgccgaagc ctcggtgtcg gcgctgcgcc cggacctggg cttcgtgcgc tcccgcctcg     240
gggcgctcat gctgctgcag ctggtgctgg gctgctggt gtgggcgctg attgcggaca     300
ccccgtacca cctgtatccg gcctatggct gggtgatgtt cgtcgctgtc ttcctctggc     360
tggtgacaat cgtcctcttc aacctctacc tgtttcagct gcacatgaag ttgtacatgg     420
ttccctggcc actggtgtta atgatcttta acatcagcgc caccgttctc tacatcaccg     480
ccttcatcgc ctgctctgcg gcagttgacc tgacatccct gaggggcacc cggccttata     540
accagcgcgc ggctgcctcg ttctttgcgt gtttggtgat gatcgcctat ggagtgagtg     600
ccttcttcag ctaccaggcc tggcgaggag taggcagcaa tcggccacc agtcagatgg      660 ctggcggcta tgcctaaacc acctgtgcca cggccccctc tggggctgaa gccgccgctg     720
ggtcacagag cagggtcacc ctgcaagcct gaagctgggg agccctgcgt ggagtcagcc     780
caacagggac tgcatttgct cctctctgcc cgtcagacat aagctctcac agcgctaagg     840
```

```
aagcaggccc aggctggcag gcatctcggc ttgcaggagg ccaactgctg agacctcttc    900
tccatccccc ttattcagtg aagatgacg ggggatctga ggctgtgtct ctgccttgtc    960
tttagaggac ttcagcgtcc aagactgggg cccaccctttc tcaccagcac taaatgcact   1020
aacaaggact ccagacctgc agccccagac ccgccgtagt ataagcctaa caagcaacac   1080
gtagcacctt agtctttgtt ccaggagagc tgagcaagct ggtgaaacca ctctccttcc   1140
tttaaacacc gtttcaacca acctctccct ggagccaacc tgtaaaaagt gggttgattg   1200
ctgacagcat ggtcttccct ccctgcattt cagacatacc agttactgaa agcaaatcag   1260 tttttaagtga tttctcagtg ctgaaaagcc tgtccaggtt tccttccctt tcccaagcct   1320
ctctctgtaa tactcccttt gggcgaagct aacatcggtg cctccccgac cttgctgact   1380
aggcacatgg gacgcaaagg agggagggaa gcaaggcctt gcctggcgag ttgtcatgtg   1440
gttggtggtg actgttttat tttttttaat aaaaataaag atgagagaaa ttaaaaaaaa   1500
accgg                                                              1505

<210> SEQ ID NO 30
<211> LENGTH: 182
<212> TYPE: PRT
<213> ORGANISM: Homo sapiens

<400> SEQUENCE: 30

Met Ala Glu Phe Pro Ser Lys Val Ser Thr Arg Thr Ser Ser Pro Ala
 1               5                  10                  15

Gln Gly Ala Glu Ala Ser Val Ser Ala Leu Arg Pro Asp Leu Gly Phe
            20                  25                  30

Val Arg Ser Arg Leu Gly Ala Leu Met Leu Leu Gln Leu Val Leu Gly
        35                  40                  45

Leu Leu Val Trp Ala Leu Ile Ala Asp Thr Pro Tyr His Leu Tyr Pro
    50                  55                  60

Ala Tyr Gly Trp Val Met Phe Val Ala Val Phe Leu Trp Leu Val Thr
65                  70                  75                  80

Ile Val Leu Phe Asn Leu Tyr Leu Phe Gln Leu His Met Lys Leu Tyr
                85                  90                  95

Met Val Pro Trp Pro Leu Val Leu Met Ile Phe Asn Ile Ser Ala Thr
            100                 105                 110

Val Leu Tyr Ile Thr Ala Phe Ile Ala Cys Ser Ala Ala Val Asp Leu
        115                 120                 125

Thr Ser Leu Arg Gly Thr Arg Pro Tyr Asn Gln Arg Ala Ala Ala Ser
    130                 135                 140

Phe Phe Ala Cys Leu Val Met Ile Ala Tyr Gly Val Ser Ala Phe Phe
145                 150                 155                 160

Ser Tyr Gln Ala Trp Arg Gly Val Gly Ser Asn Ala Ala Thr Ser Gln
                165                 170                 175

Met Ala Gly Gly Tyr Ala
            180

<210> SEQ ID NO 31
<211> LENGTH: 3726
<212> TYPE: DNA
<213> ORGANISM: Homo sapiens

<400> SEQUENCE: 31
cagcgctgct ccccgggcgc tcctccccgg gcgctcctcc ccaggcctcc cgggcgcttg     60
```

```
gatcccggcc atctccgcac ccttcaagtg ggtgtgggtg atttcctggc ggggggagca    120
gccaggtgag cccaagatgc tgctgcgctc gaagcctgcg ctgccgccgc cgctgatgct    180
gctgctcctg gggccgctgg gtcccctctc ccctggcgcc ctgccccgac ctgcgcaagc    240
acaggacgtc gtggacctgg acttcttcac ccaggagccg ctgcacctgg tgagcccctc    300
gttcctgtcc gtcaccattg acgccaacct ggccacggac ccgcggttcc tcatcctcct    360
gggttctcca aagcttcgta ccttggccag aggcttgtct cctgcgtacc tgaggtttgg    420
tggcaccaag acagacttcc taattttcga tcccaagaag gaatcaacct ttgaagagag    480
aagttactgg caatctcaag tcaaccagga tatttgcaaa tatggatcca tccctcctga    540
tgtggaggag aagttacggt tggaatggcc ctaccaggag caattgctac tccgagaaca    600
ctaccagaaa aagttcaaga acagcaccta ctcaagaagc tctgtagatg tgctatacac    660
ttttgcaaac tgctcaggac tggacttgat ctttggccta aatgcgttat taagaacagc    720
agatttgcag tggaacagtt ctaatgctca gttgctcctg gactactgct cttccaaggg    780
gtataacatt tcttgggaac taggcaatga acctaacagt ttccttaaga aggctgatat    840
tttcatcaat gggtcgcagt taggagaaga ttttattcaa ttgcataaac ttctaagaaa    900
gtccaccttc aaaaatgcaa aactctatgg tcctgatgtt ggtcagcctc gaagaaagac    960
ggctaagatg ctgaagagct tcctgaaggc tggtggagaa gtgattgatt cagttacatg   1020
gcatcactac tatttgaatg gacggactgc taccagggaa gattttctaa accctgatgt   1080
attggacatt tttatttcat ctgtgcaaaa agttttccag gtggttgaga gcaccaggcc   1140
tggcaagaag gtctggttag agaaacaag ctctgcatat ggaggcggag cgcccttgct   1200
atccgacacc tttgcagctg gctttatgtg gctggataaa ttgggcctgt cagcccgaat   1260
gggaatagaa gtggtgatga ggcaagtatt cttggagca ggaaactacc atttagtgga   1320
tgaaaacttc gatcctttac ctgattattg gctatctctt ctgttcaaga aattggtggg   1380
caccaaggtg ttaatggcaa gcgtgcaagg ttcaaagaga aggaagcttc gagtatacct   1440
tcattgcaca aacactgaca atccaaggta taaagaagga gatttaactc tgtatgccat   1500
aaacctccat aatgtcacca agtacttgcg gttaccctat ccttttctcta acaagcaagt   1560 ggataaatac cttctaagac ctttgggacc tcatggatta cttttccaaat ctgtccaact   1620 caatggtcta actctaaaga tggtggatga tcaaaccttg ccaccttttaa tggaaaaacc   1680 tctccggcca ggaagttcac tgggcttgcc agctttctca tatagttttt ttgtgataag   1740
aaatgccaaa gttgctgctt gcatctgaaa ataaaatata ctagtcctga cactgaattt   1800
ttcaagtata ctaagagtaa agcaactcaa gttataggaa aggaagcaga taccttgcaa   1860
agcaactagt gggtgcttga gagacactgg gacactgtca gtgctagatt tagcacagta   1920
ttttgatctc gctaggtaga acactgctaa taataatagc taataatacc ttgttccaaa   1980
tactgcttag cattttgcat gttttacttt tatctaaagt tttgtttttgt tttattattt   2040 atttatttat ttatttttgtg acggagagag attccatctc aaaaaaacaa gttattaaaa   2100
atgtatatga atgctcctaa tatggtcagg aagcaaggaa gcgaaggata tattatgagt   2160
tttaagaagg tgcttagctg tatatttatc tttcaaaatg tattagaaga ttttagaatt   2220
ctttccttca tgtgccatct ctacaggcac ccatcagaaa aagcatactg ccgttaccgt   2280
gaaactggtt gtaaaagaga aactatctat ttgcacctta aaagacagct agattttgct   2340
gattttcttc tttcggtttt ctttgtcagc aataatatgt gagaggacag attgttagat   2400
atgatagtat aaaaaatggt taatgacaat tcagaggcga ggagattctg taaacttaaa   2460
```

```
attactataa atgaaattga tttgtcaaga ggataaattt tagaaaacac ccaatacctt    2520
ataactgtct gttaatgctt gcttttctc tacctttctt ccttgtttca gttgggaagc    2580
ttttggctgc aagtaacaga aactcctaat tcaaatggct taagcaataa ggaaatgtat    2640
attcccacat aactagacgt tcaaacaggc caggctccag cacttcagta cgtcaccagg    2700
ggatctgggt tcttcccagc tctctgctct gccatcttta gcgctggctt cattctcaga    2760
ctctggtagc atgatggctg tagctgtttc atgggcccct tcaaacctca tagcaaccag    2820
aggaagaaaa tgagccattt tttgagtctc cttcatagac ttgaataact cttttttcaga   2880 gcttctcaca gcaaacctct cctcatgtct cctcatgtct tattgttcag aaatgggtaa    2940
tgtggccatt tcaccagtca ctgccaacaa caacgaggtt cctataattg tctctgagta    3000
accctttgga atggagaggg tgttggtcag tctacaaact gaacactgca gttctgcgct    3060
ttttaccagt gaaaaaatgt aattattttc ccctcttaag gattaatatt cttcaaatgt    3120
atgcctgtta tggatatagt atctttaaaa ttttttattt taatagcttt aggggtacac    3180 acttttgct tacaggggtg aattgtgtag tggtgaagac tcggctttta atgtacttgt      3240
cacctgagtg atgtacattg tacccaatag gtaattttc atccattacc ctccttccgc      3300
cctcttccct tctgagtctc caacatccct tataccactg tgtatgttct tgtgtaccta    3360
cagctaagct tccacttata agtgagaaca tgcagtattt ggttttccat tcctgagtta    3420
cttcccttag gataacagcc cccagttccg tccaagttgc tgcaaaatac attattcttc    3480
tttatggctg agtaatagtc catggtacat atataccaca ttttctttat ccacttatca    3540
gttgatggac acttaggtta attccattca atttcattca atttaagtat atttgtaagg    3600
agctaaagct gaaaattaaa ttttagatct ttcaatactc ttaaatttta tatgtaagtg    3660
gtttttatat tttcacattt gaaataaagt aattttata accttgaaaa aaaaaaaaaa    3720
aaaaaa                                                                 3726
```

<210> SEQ ID NO 32
<211> LENGTH: 543
<212> TYPE: PRT
<213> ORGANISM: Homo sapiens

<400> SEQUENCE: 32

```
Met Leu Leu Arg Ser Lys Pro Ala Leu Pro Pro Leu Met Leu Leu
 1               5                  10                  15

Leu Leu Gly Pro Leu Gly Pro Leu Ser Pro Gly Ala Leu Pro Arg Pro
            20                  25                  30

Ala Gln Ala Gln Asp Val Val Asp Leu Asp Phe Phe Thr Gln Glu Pro
        35                  40                  45

Leu His Leu Val Ser Pro Ser Phe Leu Ser Val Thr Ile Asp Ala Asn
    50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                85                  90                  95

Thr Lys Thr Asp Phe Leu Ile Phe Asp Pro Lys Lys Glu Ser Thr Phe
           100                 105                 110

Glu Glu Arg Ser Tyr Trp Gln Ser Gln Val Asn Gln Asp Ile Cys Lys
       115                 120                 125

Tyr Gly Ser Ile Pro Pro Asp Val Glu Glu Lys Leu Arg Leu Glu Trp
   130                 135                 140
```

```
Pro Tyr Gln Glu Gln Leu Leu Arg Glu His Tyr Gln Lys Lys Phe
145                 150                 155                 160

Lys Asn Ser Thr Tyr Ser Arg Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Asn Ala Gln Leu Leu Leu
        195                 200                 205

Asp Tyr Cys Ser Ser Lys Gly Tyr Asn Ile Ser Trp Glu Leu Gly Asn
    210                 215                 220

Glu Pro Asn Ser Phe Leu Lys Lys Ala Asp Ile Phe Ile Asn Gly Ser
225                 230                 235                 240

Gln Leu Gly Glu Asp Phe Ile Gln Leu His Lys Leu Leu Arg Lys Ser
                245                 250                 255

Thr Phe Lys Asn Ala Lys Leu Tyr Gly Pro Asp Val Gly Gln Pro Arg
            260                 265                 270

Arg Lys Thr Ala Lys Met Leu Lys Ser Phe Leu Lys Ala Gly Gly Glu
        275                 280                 285

Val Ile Asp Ser Val Thr Trp His His Tyr Tyr Leu Asn Gly Arg Thr
290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
            340                 345                 350

Pro Leu Leu Ser Asp Thr Phe Ala Ala Gly Phe Met Trp Leu Asp Lys
        355                 360                 365

Leu Gly Leu Ser Ala Arg Met Gly Ile Glu Val Met Arg Gln Val
    370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                405                 410                 415

Lys Val Leu Met Ala Ser Val Gln Gly Ser Lys Arg Arg Lys Leu Arg
            420                 425                 430

Val Tyr Leu His Cys Thr Asn Thr Asp Asn Pro Arg Tyr Lys Glu Gly
        435                 440                 445

Asp Leu Thr Leu Tyr Ala Ile Asn Leu His Asn Val Thr Lys Tyr Leu
    450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                485                 490                 495

Gly Leu Thr Leu Lys Met Val Asp Asp Gln Thr Leu Pro Pro Leu Met
            500                 505                 510

Glu Lys Pro Leu Arg Pro Gly Ser Ser Leu Gly Leu Pro Ala Phe Ser
        515                 520                 525

Tyr Ser Phe Phe Val Ile Arg Asn Ala Lys Val Ala Ala Cys Ile
    530                 535                 540

<210> SEQ ID NO 33
<211> LENGTH: 2546
```

<212> TYPE: DNA
<213> ORGANISM: Homo sapiens

<400> SEQUENCE: 33

```
ttcctttcca gcctcacgcc cgtgggctgc agttggaacg atggcggcgg cagctgccgc      60
cgggcctagc ccggggtctg gacctgggga ctccccagaa gggcccgagg gggaggctcc     120
ggagcgtcgg cggaaggcgc acgggatgct gaagctttac tacggcctct cggaagggga     180
ggcggcggga cgcccgcgg ggcccgaccc cctggacccg actgatctga acggggcgca     240
cttcgacccg gaagtttacc tagacaagct gcgtagagag tgccctctgg cccagttgat     300
ggacagtgag acggacatgg tgcggcagat ccgggctcta gacagcgaca tgcagaccct     360
ggtctatgag aactacaaca agttcatctc agccacagac accatccgga agatgaagaa     420
cgatttccgg aagatggagg atgagatgga ccggctggcc accaacatgg cagtgatcac     480
cgacttcagc gctcgcatca gcgccacgct gcaggaccgc cacgagcgca tcaccaagct     540
ggcagggggtc cacgcgctgc tgcggaagct gcagttcctc tttgagctgc cctcgcgcct     600
caccaagtgc gtggaactgg gcgcctatgg gcaggcggtg cgctaccagg gccgcgcgca     660
ggccgtgctg cagcagtacc aacacctgcc ctcgttccgc gccatccagg acgactgcca     720
ggtcatcacg gcccgcctgg cccagcagct gcggcagcgc tttagggagg gcggctcagg     780
cgccccggag caggcagagt gcgtggagct gctgctggcc ctgggcgagc tgcggagga     840
gctgtgcgag gagttcctgg cgcacgcccg cggccggctg gagaaggagc tgagaaacct     900
ggaggccgag ctggggccct cacctccggc tcccgacgtg ttagagttca ccgaccatgg     960
aggcagtggc ttcgtgggcg gcctctgcca ggtggcggcg gcctaccagg agctgtttgc    1020
ggcccagggc ccagcaggtg ccgagaagct ggcggccttc gcccggcagc tgggcagccg    1080
ctattttgcg ctggtggagc ggcggctggc gcaggagcag ggtggtggtg acaactcact    1140
gctggtgcgg gcgctggacc gcttccaccg gcgcttgcgg gctcccgggg ccctgctggc    1200
cgctgccggg ctcgcagacg ctgccacgga gatcgtggaa cgagtggccc gcgagcgcct    1260
gggccaccac ctgcagggtc tccggcggc cttcctgggc tgcctgacag acgtccgcca    1320
ggcgctggca gcacctcgcg tggctgggaa ggagggccct ggcctggccg agttgctggc    1380
caatgtggcc agctccatcc tgagccacat taaggcctct ctggcagcag tgcacccttt    1440
caccgccaaa gaggtgtcct tctccaacaa gccctacttc cggggtgagt tctgcagtca    1500
gggtgtccgt gagggcctca tcgtgggctt cgtccactct atgtgccaga cggctcagag    1560
cttctgcgac agccctgggg agaaggggg tgccacacca cctgccctgc tcctgctgct    1620
ctcccgcctc tgcctggact acgagacggc caccatctcc tacatcctca ctctcactga    1680
tgaacagttt ctggtgcagg atcagttccc agtgacgccc gtgagcacgc tgtgtgcaga    1740
ggccagggaa acgcgcggc ggctgctgac ccactacgtg aaggtgcagg gcctggtcat    1800
atcacagatg ctgcgcaaga gcgtggagac tcgcgactgg ctcagcactc tggagccccg    1860
gaatgtgcgg gccgtcatga gcgggtggt ggaggatacc accgccatcg acgtgcaggt    1920
ggggctcctg tacgaagagg gtgttcgcaa ggcccagagc agcgactcca gcaagaggac    1980
tttctccgtg tacagcagct ctcggcagca gggccgctac gccccagct ataccccag    2040
tgcccccgatg gacaccaacc tcttgagcaa tatccagaag ctattctctg aacgtattga    2100
tgtgttcagc cctgtggagt tcaacaaggt gtcggtgctg accggcatca tcaagatcag    2160
cctgaagacg ctgctggagt gtgtgcggct gcgcacccttt gggcgcttcg ggctgcagca    2220
```

```
ggtgcaagtg gactgccact ttctgcagct ctacctgtgg cgttttgtgg ccgacgaaga    2280
actcgtgcac ttgctgctgg acgaagtggt ggcctctgct gccctgcgct gcccagaccc    2340
tgtgcccatg gagcccagtg tggttgaggt catctgcgag cgcggctagg cgcagccgct    2400
gccatgcacc ggtctgtccc tgcacccat ggcacccagg atctggtctc ggtggtcctt     2460
ccccgcaggc aggtgtcagg accggcctaa taaacatgtg tggcctcctc aaaaaaaaaa    2520 aaaaaaaaa aaaaaaaaaa aaaaaa                                          2546
```

<210> SEQ ID NO 34
<211> LENGTH: 782
<212> TYPE: PRT
<213> ORGANISM: Homo sapiens

<400> SEQUENCE: 34

```
Met Ala Ala Ala Ala Ala Gly Pro Ser Pro Gly Ser Gly Pro Gly
 1               5                  10                  15

Asp Ser Pro Glu Gly Pro Glu Gly Ala Pro Glu Arg Arg Arg Lys
                20                  25                  30

Ala His Gly Met Leu Lys Leu Tyr Tyr Gly Leu Ser Glu Gly Glu Ala
        35                  40                  45

Ala Gly Arg Pro Ala Gly Pro Asp Pro Leu Asp Pro Thr Asp Leu Asn
    50                  55                  60

Gly Ala His Phe Asp Pro Glu Val Tyr Leu Asp Lys Leu Arg Arg Glu
65                  70                  75                  80

Cys Pro Leu Ala Gln Leu Met Asp Ser Glu Thr Asp Met Val Arg Gln
                85                  90                  95

Ile Arg Ala Leu Asp Ser Asp Met Gln Thr Leu Val Tyr Glu Asn Tyr
            100                 105                 110

Asn Lys Phe Ile Ser Ala Thr Asp Thr Ile Arg Lys Met Lys Asn Asp
        115                 120                 125

Phe Arg Lys Met Glu Asp Glu Met Asp Arg Leu Ala Thr Asn Met Ala
    130                 135                 140

Val Ile Thr Asp Phe Ser Ala Arg Ile Ser Ala Thr Leu Gln Asp Arg
145                 150                 155                 160

His Glu Arg Ile Thr Lys Leu Ala Gly Val His Ala Leu Leu Arg Lys
                165                 170                 175

Leu Gln Phe Leu Phe Glu Leu Pro Ser Arg Leu Thr Lys Cys Val Glu
            180                 185                 190

Leu Gly Ala Tyr Gly Gln Ala Val Arg Tyr Gln Gly Arg Ala Gln Ala
        195                 200                 205

Val Leu Gln Gln Tyr Gln His Leu Pro Ser Phe Arg Ala Ile Gln Asp
    210                 215                 220

Asp Cys Gln Val Ile Thr Ala Arg Leu Ala Gln Gln Leu Arg Gln Arg
225                 230                 235                 240

Phe Arg Glu Gly Gly Ser Gly Ala Pro Glu Gln Ala Glu Cys Val Glu
                245                 250                 255

Leu Leu Leu Ala Leu Gly Glu Pro Ala Glu Glu Leu Cys Glu Glu Phe
            260                 265                 270

Leu Ala His Ala Arg Gly Arg Leu Glu Lys Glu Leu Arg Asn Leu Glu
        275                 280                 285

Ala Glu Leu Gly Pro Ser Pro Pro Ala Pro Asp Val Leu Glu Phe Thr
    290                 295                 300

Asp His Gly Gly Ser Gly Phe Val Gly Gly Leu Cys Gln Val Ala Ala
305                 310                 315                 320
```

```
Ala Tyr Gln Glu Leu Phe Ala Ala Gln Gly Pro Ala Gly Ala Glu Lys
                325                 330                 335

Leu Ala Ala Phe Ala Arg Gln Leu Gly Ser Arg Tyr Phe Ala Leu Val
            340                 345                 350

Glu Arg Arg Leu Ala Gln Gln Gly Gly Gly Asp Asn Ser Leu Leu
        355                 360                 365

Val Arg Ala Leu Asp Arg Phe His Arg Leu Arg Ala Pro Gly Ala
    370                 375                 380

Leu Leu Ala Ala Ala Gly Leu Ala Asp Ala Ala Thr Glu Ile Val Glu
385                 390                 395                 400

Arg Val Ala Arg Glu Arg Leu Gly His His Leu Gln Gly Leu Arg Ala
                405                 410                 415

Ala Phe Leu Gly Cys Leu Thr Asp Val Arg Gln Ala Leu Ala Ala Pro
            420                 425                 430

Arg Val Ala Gly Lys Glu Gly Pro Gly Leu Ala Glu Leu Leu Ala Asn
            435                 440                 445

Val Ala Ser Ser Ile Leu Ser His Ile Lys Ala Ser Leu Ala Ala Val
450                 455                 460

His Leu Phe Thr Ala Lys Glu Val Ser Phe Ser Asn Lys Pro Tyr Phe
465                 470                 475                 480

Arg Gly Glu Phe Cys Ser Gln Gly Val Arg Glu Gly Leu Ile Val Gly
                485                 490                 495

Phe Val His Ser Met Cys Gln Thr Ala Gln Ser Phe Cys Asp Ser Pro
            500                 505                 510

Gly Glu Lys Gly Gly Ala Thr Pro Ala Leu Leu Leu Leu Ser
            515                 520                 525

Arg Leu Cys Leu Asp Tyr Glu Thr Ala Thr Ile Ser Tyr Ile Leu Thr
            530                 535                 540

Leu Thr Asp Glu Gln Phe Leu Val Gln Asp Gln Phe Pro Val Thr Pro
545                 550                 555                 560

Val Ser Thr Leu Cys Ala Glu Ala Arg Glu Thr Ala Arg Arg Leu Leu
                565                 570                 575

Thr His Tyr Val Lys Val Gln Gly Leu Val Ile Ser Gln Met Leu Arg
            580                 585                 590

Lys Ser Val Glu Thr Arg Asp Trp Leu Ser Thr Leu Glu Pro Arg Asn
            595                 600                 605

Val Arg Ala Val Met Lys Arg Val Val Glu Asp Thr Thr Ala Ile Asp
            610                 615                 620

Val Gln Val Gly Leu Leu Tyr Glu Glu Gly Val Arg Lys Ala Gln Ser
625                 630                 635                 640

Ser Asp Ser Ser Lys Arg Thr Phe Ser Val Tyr Ser Ser Arg Gln
                645                 650                 655

Gln Gly Arg Tyr Ala Pro Ser Tyr Thr Pro Ser Ala Pro Met Asp Thr
            660                 665                 670

Asn Leu Leu Ser Asn Ile Gln Lys Leu Phe Ser Glu Arg Ile Asp Val
            675                 680                 685

Phe Ser Pro Val Glu Phe Asn Lys Val Ser Val Leu Thr Gly Ile Ile
            690                 695                 700

Lys Ile Ser Leu Lys Thr Leu Leu Glu Cys Val Arg Leu Arg Thr Phe
705                 710                 715                 720

Gly Arg Phe Gly Leu Gln Gln Val Gln Val Asp Cys His Phe Leu Gln
                725                 730                 735
```

| | | | | | | | | | | | | |
|---|---|---|---|---|---|---|---|---|---|---|---|---|
| Leu | Tyr | Leu | Trp | Arg | Phe | Val | Ala | Asp | Glu | Glu | Leu | Val | His | Leu | Leu |
| | | | 740 | | | | | 745 | | | | | 750 | | |

| | | | | | | | | | | | | |
|---|---|---|---|---|---|---|---|---|---|---|---|---|
| Leu | Asp | Glu | Val | Val | Ala | Ser | Ala | Ala | Leu | Arg | Cys | Pro | Asp | Pro | Val |
| | | 755 | | | | | 760 | | | | | 765 | | | |

| | | | | | | | | | | | |
|---|---|---|---|---|---|---|---|---|---|---|---|
| Pro | Met | Glu | Pro | Ser | Val | Val | Glu | Val | Ile | Cys | Glu | Arg | Gly |
| | 770 | | | | | 775 | | | | | 780 | | |

<210> SEQ ID NO 35
<211> LENGTH: 2857
<212> TYPE: DNA
<213> ORGANISM: Homo sapiens

<400> SEQUENCE: 35

```
ttttgaaaat cttgttgatt ctggggagcc gagcgcgcgg cgcgagcgtc acgccagaca    60
gcggcccgcg cgccttctcc tcggcgtcgg ccgccgccgc ctcccagaac ctcctcgtgc   120
cctcgcgtgc caggcccgcg gcggccgaaa tccgcggttc acagcatgtc cgcctcggcc   180
cctgctgcgg aggggaggg aaccccacc cagcccgcgt ccgagaaaga acccgaaatg   240
cccggtccca gagaggagag cgaggaggaa gaggacgagg acgacgagga ggaggaggag   300
gaggaaaaag aaaagagtct catcgtggaa ggcaagaggg aaaagaaaaa agtagagagg   360
ttgacaatgc aagtctcttc cttacagaga gagccattta caattgcaca aggaaagggg   420
cagaaacttt gtgaaattga aggatacat tttttctaa gtaagaagaa aaccgatgaa   480
cttagaaatc tacacaaact gctttacaac aggccaggca ctgtgtcctc attaaagaag   540
aatgtgggtc agttcagtgg ctttccattt gaaaaggga gtgtccaata taaaagaag   600
gaagaaatgt tgaaaaaatt tagaaatgcc atgttaaaga gcatctgtga ggttcttgat   660
ttggagagat caggtgtaaa tagtgaacta gtgaagagga tcttgaattt cttaatgcat   720
ccaaagcctt ctggcaaacc attgccgaaa tctaaaaaaa cttgtagcaa aggcagtaaa   780
aaggaacgga cagttctgg aatggcaagg aaggctaagc gaaccaaatg tcctgaaatt   840
ctgtcagatg aatctagtag tgatgaagat gaaagaaaa caaggaaga gtcttcagat   900
gatgaagata agaaagtga agaggagcca ccaaaaaaga cagccaaaag agaaaaacct   960
aaacagaaag ctacttctaa aagtaaaaaa tctgtgaaaa gtgccaatgt taagaaagca  1020
gatagcagca ccaccaagaa gaatcaaaac agttccaaaa aagaaagtga gtctgaggat  1080
agttcagatg atgaaccttt aattaaaaag ttgaagaaac cccctacaga tgaagagtta  1140
aaggaaacaa taagaaatt actggccagt gctaacttgg aagaagtcac aatgaaacag  1200
atttgcaaaa aggtctatga aaattatcct acttatgatt taactgaaag aaaagatttc  1260
ataaaaacaa ctgtaaaaga gctaatttct gagatagag gacagagaag atgactcgtt  1320
cccatagatt tgaagatctg atttatacca ttataccagc aaagagaatg tatttccttt  1380
tctaaatcct tgttaagcaa cgttagtaga acttactgct gaccttttta tcttgagtgt  1440
tatgtgaatt tgagtttgct gttttaaatt gcatttctat gccatttta gtttaaaatc  1500
ttgcatggca ttaattgttc cttgctttta tagttgtatt ttgtacattt tggatttctt  1560
tatataaggt catagattct tgagctgttg tggttttag tgcacttaat attagcttgc  1620
ttaaggcata cttttaatca agtagaacaa aaactattat caccaggatt tatacataca  1680
gagattgtag tatttagtat atgaaatatt ttgaatacac atctctgtca gtgtgaaaat  1740
tcagcggcag tgtgtccatc atattaaaaa tatacaagct acagttgtcc agatcactga  1800
attggaactt ttctcctgca tgtgtatata tgtcaaattg tcagcatgac aaaagtgaca  1860
```

-continued

```
gatgttatttt ttgtattttt aaaaaacaat tggttgtata taaagtttttt ttatttcttt    1920 tgtgcagatc acttttttaaa ctcacatagg taggtatctt tatagttgta gactatggaa    1980
tgtcagtgtt cagccaaaca gtatgatgga acagtgaaag tcaattcagt gatggcaaca    2040
ctgaaggaac agttaccctg ctttgcctcg aaagtgtcat caatttgtaa ttttagtatt    2100
aactctgtaa aagtgtctgt aggtacgttt tatattatat aaggacagac caaaaatcaa    2160
cctatcaaag cttcaaaaac tttgggaaag ggtgggatta agtacaagca catttggctt    2220
acagtaaatg aactgatttt tattaactgc ttttgcccat ataaaatgct gatatttact    2280
ggaaacctag ccagcttcac gattatgact aaagtaccag attataatgc cagaatataa    2340
tgtgcaggca atcgtggatg tctctgacaa agtgtgtctc aaaaataata tacttttaca    2400
ttaaagaaat ttaatgtttc tctggagttg gggctcttgg ctttcagagt ttggttaatc    2460
agtgttgatt ctagatgatc aacataatgg accactcctg aatgagactt aattttgtct    2520
ttcaaattta ctgtcttaaa tcagtttatt aaatctgaat tttaaaacat gctgtttatg    2580
acacaatgac acatttgttg caccaattaa gtgttgaaaa atatctttgc atcatagaac    2640
agaaatatat aaaatatat gttgaatgtt aacaggtatt ttcacaggtt tgtttcttga    2700
tagttactca gacactaggg aaaggtaaat acaagtgaac aaaataagca actaaatgag    2760
acctaataat tggccttcga ttttaaatat ttgttcttat aaaccttgtc aataaaaata    2820
aatctaaatc aaaaaaaaaa aaaaaaaaaa aaaaaaa                               2857
```

<210> SEQ ID NO 36
<211> LENGTH: 375
<212> TYPE: PRT
<213> ORGANISM: Homo sapiens

<400> SEQUENCE: 36

```
Met Ser Ala Ser Ala Pro Ala Glu Gly Glu Gly Thr Pro Thr Gln
 1               5                  10                  15
Pro Ala Ser Glu Lys Glu Pro Glu Met Pro Gly Pro Arg Glu Ser
                20                  25                  30
Glu Glu Glu Glu Asp Glu Asp Asp Glu Glu Glu Glu Glu Glu Lys
                35                  40                  45
Glu Lys Ser Leu Ile Val Glu Gly Lys Arg Glu Lys Lys Val Glu
 50                  55                  60
Arg Leu Thr Met Gln Val Ser Ser Leu Gln Arg Glu Pro Phe Thr Ile
 65                  70                  75                  80
Ala Gln Gly Lys Gly Gln Lys Leu Cys Glu Ile Glu Arg Ile His Phe
                    85                  90                  95
Phe Leu Ser Lys Lys Lys Thr Asp Glu Leu Arg Asn Leu His Lys Leu
                    100                 105                 110
Leu Tyr Asn Arg Pro Gly Thr Val Ser Leu Lys Lys Asn Val Gly
                    115                 120                 125
Gln Phe Ser Gly Phe Pro Phe Glu Lys Gly Ser Val Gln Tyr Lys Lys
                    130                 135                 140
Lys Glu Glu Met Leu Lys Lys Phe Arg Asn Ala Met Leu Lys Ser Ile
 145                 150                 155                 160
Cys Glu Val Leu Asp Leu Glu Arg Ser Gly Val Asn Ser Glu Leu Val
                    165                 170                 175
Lys Arg Ile Leu Asn Phe Leu Met His Pro Lys Pro Ser Gly Lys Pro
                    180                 185                 190
Leu Pro Lys Ser Lys Lys Thr Cys Ser Lys Gly Ser Lys Lys Glu Arg
                    195                 200                 205
Asn Ser Ser Gly Met Ala Arg Lys Ala Lys Arg Thr Lys Cys Pro Glu
 210                 215                 220
Ile Leu Ser Asp Glu Ser Ser Asp Glu Asp Lys Lys Asn Lys
 225                 230                 235                 240
Glu Glu Ser Ser Asp Asp Glu Asp Lys Glu Ser Glu Glu Pro Pro
                    245                 250                 255
Lys Lys Thr Ala Lys Arg Glu Lys Pro Lys Gln Lys Ala Thr Ser Lys
                    260                 265                 270
Ser Lys Lys Ser Val Lys Ser Ala Asn Val Lys Lys Ala Asp Ser Ser
                    275                 280                 285
Thr Thr Lys Lys Asn Gln Asn Ser Ser Lys Lys Glu Ser Glu Ser Glu
```

|  |  |  |  |  | 290 |  |  |  |  | 295 |  |  |  |  | 300 |  |
|---|---|---|---|---|---|---|---|---|---|---|---|---|---|---|---|---|
| Asp | Ser | Ser | Asp | Asp | Glu | Pro | Leu | Ile | Lys | Lys | Leu | Lys | Lys | Pro | Pro |  |
| 305 |  |  |  |  | 310 |  |  |  |  | 315 |  |  |  |  | 320 |  |
| Thr | Asp | Glu | Glu | Leu | Lys | Glu | Thr | Ile | Lys | Lys | Leu | Leu | Ala | Ser | Ala |  |
|  |  |  |  | 325 |  |  |  |  | 330 |  |  |  |  | 335 |  |  |
| Asn | Leu | Glu | Glu | Val | Thr | Met | Lys | Gln | Ile | Cys | Lys | Lys | Val | Tyr | Glu |  |
|  |  |  | 340 |  |  |  |  | 345 |  |  |  |  | 350 |  |  |  |
| Asn | Tyr | Pro | Thr | Tyr | Asp | Leu | Thr | Glu | Arg | Lys | Asp | Phe | Ile | Lys | Thr |  |
|  |  | 355 |  |  |  |  | 360 |  |  |  |  | 365 |  |  |  |  |
| Thr | Val | Lys | Glu | Leu | Ile | Ser |  |  |  |  |  |  |  |  |  |  |
|  |  | 370 |  |  |  | 375 |  |  |  |  |  |  |  |  |  |  |

<210> SEQ ID NO 37
<211> LENGTH: 3923
<212> TYPE: DNA
<213> ORGANISM: Homo sapiens

<400> SEQUENCE: 37

```
ctctctgagg ctgcgccaag acctgaagcg gcggaccgag agcccgggtc tgagactgag     60
agagcaacgg aatggaggcg gggtagaggc ggaaacacaa cctgcagggc cagagcgagg    120
cgcgagaagg acggcggcgt gaggggggcgg ggcgcgcagc gcgagaaggc aggcacgagg    180
ggcgagcgcg aggcggggca cggcgcgtgg cgtgagacgg ggcggggcgc gcgtatcggc    240
gccgcggccg cgtgacgcgt tttcaaatct tcaaccgccg cagcccactc gtttgtgctt    300
tgcgccttcc tcctccgcgc cttggagccg atccggccc cggaaacccg acctgcagac    360
gcggtacctc tactgcgtag aggccgtagc tggcggaagg agagaggcgg ccgtcctgtc    420
aacaggccgg gggaagccgt gctttcgcgg ctgcccggtg cgacactttc tccggaccca    480
gcatgtaggt gccgggcgac tgccatgaac tccggagcca tgaggatcca cagtaaagga    540
catttccagg gtggaatcca agtcaaaaat gaaaaaaaca gaccatctct gaaatctctg    600
aaaactgata acaggccaga aaatccaaa tgtaagccac tttggggaaa agtatttac    660
cttgacttac cttctgtcac catatctgaa aaacttcaaa aggacattaa ggatctggga    720
gggcgagttg aagaatttct cagcaaagat atcagttatc ttatttcaaa taagaaggaa    780
gctaaatttg cacaaaacctt gggtcgaatt tctcctgtac caagtccaga atctgcatat    840
actgcagaaa ccacttcacc tcatcccagc catgatggaa gttcatttaa gtcaccagac    900
acagtgtgtt taagcagagg aaaattatta gttgaaaaag ctatcaagga ccatgatttt    960
attccttcaa atagtatatt atcaaatgcc ttgtcatggg gagtaaaaat tcttcatatt   1020
gatgacatta gatactacat tgaacaaaag aaaaaagagt tgtatttact caagaaatca   1080
agtacttcag taagagatgg gggcaaaaga gttggtagtg tgcacaaaaa acaagaaca   1140
ggaagactca aaaagccttt tgtaaaggtg gaagatatga gccaactttta taggccatttt   1200
tatcttcagc tgaccaatat gccttttata aattattcta ttcagaagcc ctgcagtcca   1260
tttgatgtag acaagccatc tagtatgcaa aagcaaactc aggttaaact aagaatccaa   1320
acagatggcg ataagtatgg tggaacctca attcaactcc agttgaaaga agaagaagaa   1380
aaaggatatt gtgaatgttg cttgcagaaa tatgaagatc tagaaactca ccttctaagt   1440
gagcaacaca gaaactttgc acagagtaac cagtatcaag ttgttgatga tattgtatct   1500
aagttagttt ttgactttgt ggaatatgaa aaggacacac taaaaagaa aagaataaaa   1560
tacagtgttg gatccctttc tcctgtttct gcaagtgtcc tgaaaagac tgaacaaaag   1620
gaaaaagtgg aattgcaaca tatttctcag aaagattgcc aggaagatga tacaacagtg   1680
aaggagcaga atttcctgta taagagacc caggaaactg aaaaaaagct cctgtttatt   1740
tcagagccca tcccccaccc ttcaaatgaa ttgagagggc ttaatgagaa aatgagtaat   1800
```

|  |  |
|---|---|
| aaatgttcca tgttaagtac agctgaagat gacataagac agaattttac acagctacct | 1860 |
| ctacataaaa acaaacagga atgcattctt gacatttccg aacacacatt aagtgaaaat | 1920 |
| gacttagaag aactaagggt agatcactat aaatgtaaca tacaggcatc tgtacatgtt | 1980 |
| tctgatttca gtacagataa tagtggatct caaccaaaac agaagtcaga tactgtgctt | 2040 |
| tttccagcaa aggatctcaa ggaaaaggac cttcattcaa tatttactca tgattctggt | 2100 |
| ctgataacaa taaacagttc acaagagcac ctaactgttc aggcaaaggc tccattccat | 2160 |
| actcctcctg aggaacccaa tgaatgtgac ttcaagaata tggatagttt accttctggt | 2220 |
| aaaatacatc gaaagtgaa aataatatta ggacgaaata gaaagaaaa tctggaacca | 2280 |
| aatgctgaat tgataaaag aactgaattt attacacaag aagaaaacag aatttgtagt | 2340 |
| tcaccggtac agtctttact agacttgttt cagactagtg aagagaaatc agaattttg | 2400 |
| ggtttcacaa gctacacaga aaagagtggt atatgcaatg ttttagatat ttgggaagag | 2460 |
| gaaaattcag ataatctgtt aacagcgttt ttctcgtccc cttcaacttc tacatttact | 2520 |
| ggcttttaga atttaaaaaa tgcatacttt tcagaagtga taaggatcat attcttgaaa | 2580 |
| tttttataaa tatgtatgga aattcttagg atttttttac cagctttgtt tacagaccca | 2640 |
| aatgtaaata ttaaaaataa atatttgcaa ttttctacag aattgaatac ctgttaaaga | 2700 |
| aaaattacag aataaacttg tgactggtct tgttttacat tatatatatg ttcgtaattg | 2760 |
| tttcctgaga attacaatga ataataattt gctttgtcac tgaaaaccac cagtgaagtg | 2820 |
| caatttgggg aatatcaaac ttagcattat acatttggat attctagttg tattgtaaat | 2880 |
| tttaaaagat tatcaggata acatgacctt gccttgaaaa acctaaattt catacagaaa | 2940 |
| ggaaaaatac atttctatgc ttgaattctg gaaatcatca gaatattga cacttgaggg | 3000 |
| tcactggtgg accatgctag tattttggtg ctgagtaatt agattatgta taggggtaac | 3060 |
| tggaagccat gaaggaagga cttaaccagg ctaccaagtg aatataatt tatctgctat | 3120 |
| tttaattac ttaccttgta ataactttta ataatattca aaagttgact ctcctgtggc | 3180 |
| tcatgccaca ggatcccagc actttgggag gccgaggcag gctgatcacg aggtcagaag | 3240 |
| atcaagacca tcctggccaa catggtgaaa ccttgtctac taaaaataca aaaaattagc | 3300 |
| tgggcatggc ggcatgcgcc tgtagtccca gctactccct ccagaggctg agaattgctt | 3360 |
| gaacctggga agtgcaggtt gcagtgagcc aagattgtgc cactgtattc cagactgggt | 3420 |
| gacagagtga gactccatct caaaaaaaaa aagttgact ctaccccta atttggtagg | 3480 |
| agatgaagga gaaaaggatg gcattgaatt atagatacag ttttgggata tatacaagga | 3540 |
| ttgccttgat ctggcactta ctgatacaag catttggaga agagaaaatt caaatataag | 3600 |
| aaatttcaat ttgaatctgt ggatataagg catttgcctt tgagtatgtt cttgtaggag | 3660 |
| taagactacc accagtgaca ttcaattggt tctattgcat agtacatgaa tctattgtca | 3720 |
| ctaaaaatta ggttactaat cttaattttt ttgaaatata tgattctcag tacaggacta | 3780 |
| attcatatgc ttttcctgca tacattattt tgatcatttg gataacatca atgaacactg | 3840 |
| gcttttttaac acctttgttt ttcataccag tacctgaagt aggctcaata aaagagtctt | 3900 |
| tacagtgaaa aaaaaaaaa aaa | 3923 |

<210> SEQ ID NO 38
<211> LENGTH: 674
<212> TYPE: PRT
<213> ORGANISM: Homo sapiens

<400> SEQUENCE: 38

```
Met Asn Ser Gly Ala Met Arg Ile His Ser Lys Gly His Phe Gln Gly
 1               5                  10                  15

Gly Ile Gln Val Lys Asn Glu Lys Asn Arg Pro Ser Leu Lys Ser Leu
                20                  25                  30

Lys Thr Asp Asn Arg Pro Glu Lys Ser Lys Cys Lys Pro Leu Trp Gly
            35                  40                  45

Lys Val Phe Tyr Leu Asp Leu Pro Ser Val Thr Ile Ser Glu Lys Leu
        50                  55                  60

Gln Lys Asp Ile Lys Asp Leu Gly Gly Arg Val Glu Glu Phe Leu Ser
 65                  70                  75                  80

Lys Asp Ile Ser Tyr Leu Ile Ser Asn Lys Lys Glu Ala Lys Phe Ala
                85                  90                  95

Gln Thr Leu Gly Arg Ile Ser Pro Val Pro Ser Pro Glu Ser Ala Tyr
            100                 105                 110

Thr Ala Glu Thr Thr Ser Pro His Pro Ser His Asp Gly Ser Ser Phe
        115                 120                 125

Lys Ser Pro Asp Thr Val Cys Leu Ser Arg Gly Lys Leu Leu Val Glu
130                 135                 140

Lys Ala Ile Lys Asp His Asp Phe Ile Pro Ser Asn Ser Ile Leu Ser
145                 150                 155                 160

Asn Ala Leu Ser Trp Gly Val Lys Ile Leu His Ile Asp Asp Ile Arg
                165                 170                 175

Tyr Tyr Ile Glu Gln Lys Lys Lys Glu Leu Tyr Leu Leu Lys Lys Ser
                180                 185                 190

Ser Thr Ser Val Arg Asp Gly Gly Lys Arg Val Gly Ser Gly Ala Gln
            195                 200                 205

Lys Thr Arg Thr Gly Arg Leu Lys Lys Pro Phe Val Lys Val Glu Asp
210                 215                 220

Met Ser Gln Leu Tyr Arg Pro Phe Tyr Leu Gln Leu Thr Asn Met Pro
225                 230                 235                 240

Phe Ile Asn Tyr Ser Ile Gln Lys Pro Cys Ser Pro Phe Asp Val Asp
                245                 250                 255

Lys Pro Ser Ser Met Gln Lys Gln Thr Gln Val Lys Leu Arg Ile Gln
            260                 265                 270

Thr Asp Gly Asp Lys Tyr Gly Gly Thr Ser Ile Gln Leu Gln Leu Lys
        275                 280                 285

Glu Lys Lys Lys Gly Tyr Cys Glu Cys Leu Gln Lys Tyr Glu
290                 295                 300

Asp Leu Glu Thr His Leu Leu Ser Glu Gln His Arg Asn Phe Ala Gln
305                 310                 315                 320

Ser Asn Gln Tyr Gln Val Val Asp Asp Ile Val Ser Lys Leu Val Phe
                325                 330                 335

Asp Phe Val Glu Tyr Glu Lys Asp Thr Pro Lys Lys Arg Ile Lys
            340                 345                 350

Tyr Ser Val Gly Ser Leu Ser Pro Val Ser Ala Ser Val Leu Lys Lys
        355                 360                 365

Thr Glu Gln Lys Glu Lys Val Glu Leu Gln His Ile Ser Gln Lys Asp
370                 375                 380

Cys Gln Glu Asp Asp Thr Thr Val Lys Glu Gln Asn Phe Leu Tyr Lys
385                 390                 395                 400

Glu Thr Gln Glu Thr Glu Lys Lys Leu Leu Phe Ile Ser Glu Pro Ile
                405                 410                 415
```

```
Pro His Pro Ser Asn Glu Leu Arg Gly Leu Asn Glu Lys Met Ser Asn
            420                 425                 430

Lys Cys Ser Met Leu Ser Thr Ala Glu Asp Asp Ile Arg Gln Asn Phe
            435                 440                 445

Thr Gln Leu Pro Leu His Lys Asn Lys Gln Glu Cys Ile Leu Asp Ile
            450                 455                 460

Ser Glu His Thr Leu Ser Glu Asn Asp Leu Glu Glu Leu Arg Val Asp
465                 470                 475                 480

His Tyr Lys Cys Asn Ile Gln Ala Ser Val His Val Ser Asp Phe Ser
                485                 490                 495

Thr Asp Asn Ser Gly Ser Gln Pro Lys Gln Lys Ser Asp Thr Val Leu
            500                 505                 510

Phe Pro Ala Lys Asp Leu Lys Glu Lys Asp Leu His Ser Ile Phe Thr
            515                 520                 525

His Asp Ser Gly Leu Ile Thr Ile Asn Ser Ser Gln Glu His Leu Thr
            530                 535                 540

Val Gln Ala Lys Ala Pro Phe His Thr Pro Glu Glu Pro Asn Glu
545                 550                 555                 560

Cys Asp Phe Lys Asn Met Asp Ser Leu Pro Ser Gly Lys Ile His Arg
                565                 570                 575

Lys Val Lys Ile Ile Leu Gly Arg Asn Arg Lys Glu Asn Leu Glu Pro
            580                 585                 590

Asn Ala Glu Phe Asp Lys Arg Thr Glu Phe Ile Thr Gln Glu Glu Asn
            595                 600                 605

Arg Ile Cys Ser Ser Pro Val Gln Ser Leu Leu Asp Leu Phe Gln Thr
            610                 615                 620

Ser Glu Glu Lys Ser Glu Phe Leu Gly Phe Thr Ser Tyr Thr Glu Lys
625                 630                 635                 640

Ser Gly Ile Cys Asn Val Leu Asp Ile Trp Glu Glu Asn Ser Asp
                645                 650                 655

Asn Leu Leu Thr Ala Phe Phe Ser Ser Pro Ser Thr Ser Thr Phe Thr
            660                 665                 670

Gly Phe

<210> SEQ ID NO 39
<211> LENGTH: 1946
<212> TYPE: DNA
<213> ORGANISM: Homo sapiens

<400> SEQUENCE: 39
gatggcggcg cccaggccct gccacgcaga cttccgcccg gcgcggagac cgaaggctgg      60
cggctggtcg cgttgcaggc aacatgtcgg aaggaaacgc cgccggcgag cccagcacgc     120
cgggagggcc ccgacctctc ctgactgggg cccgggggct catcgggcgg cggccggcgc     180
ctcccctcac ccccggccgc cttccctcca tccgttccag ggacctcacc ctcggggggag    240 tcaagaagaa aaccttcacc ccaaatatca tcagtcggaa gatcaaggaa gagcccaagg     300
aagaagtaac tgtcaagaag gagaagcgtg aagggacag agaccgacaa cgagaggggc      360
atggacgagg gcgaggccgt ccagaagtga tccagtctca ctccatcttt gagcagggcc     420
cagctgaaat gatgaagaaa aagggaact gggataagac agtggatgtg tcagacatgg      480
gaccttctca tatcatcaac atcaaaaaag agaagagaga gacagacgaa gaaactaaac     540
agatcttgcg tatgctggag aaggacgatt tcctcgatga ccccggcctg aggaacgaca     600
```

```
ctcgaaatat gcctgtgcag ctgccgctgg ctcactcagg atggcttttt aaggaagaaa      660
atgacgaacc agatgttaaa ccttggctgg ctggccccaa ggaagaggac atggaggtgg      720
acatacctgc tgtgaaagtg aaagaggagc cacgagatga ggaggaagag gccaagatga      780
aggctcctcc caaagcagcc aggaagactc caggcctccc gaaggatgta tctgtggcag      840
agctgctgag ggagctgagc ctcaccaagg aagaggaact gctgtttctg cagctgccag      900
acaccctccc tggccagcca cccacccagg acatcaagcc tatcaagaca gaggtgcagg      960
gcgaggacgg acaggtggtg ctcatcaagc aggagaaaga ccgagaagcc aaattggcag     1020
agaatgcttg taccctggct gacctgacag agggtcaggt tggcaagcta ctcatccgca     1080
agtctggaag ggtgcaactc ctcttgggca aggtgactct ggacgtgacc atgggaactg     1140
cctgctcctt cctgcaggag ctggtgtccg tgggccttgg agacagtagg acaggggaga     1200
tgacagtcct gggacacgtg aagcacaaac ttgtatgttc ccctgatttt gaatccctct     1260
tggatcacaa acaccggtaa aatgagcagg tggaggagga cggcgcctgt gcccacggct     1320
gctgcctgct ccagacattt tgttcttgaa tctgtgagac ccagaagggg cccactgagc     1380
ccactcactc cagcctttgg caaccattgt tccaggtccc ccagggcttc ctcccacagc     1440
agctgtgaat ggcacagtga ccttcctgca gcgtggagat ggcacatcct tgctgctggg     1500
gacttggccc tgctatttat ttttgtattt atgtcttaat ctcttccact gatgcatcct     1560
ccaagggtag atggggaggg tctgtgtgaa ggggccggct tctcttggtg cctgctgggt     1620
tgcaggggca ggaagcgtgt ggactgcagc ttctgctggt gctcccccg tcctcctgga     1680
ggcagtatag gagagagagc aaggattgag tctgagactt aagcactcgg tcccagcttg     1740
ccagttcctg gttctgtgtc cttggacaaa ctacctaacc tttctgagcc tcctataccc     1800
catccgacac aaatggggat gataccctacc tccaggggttg gcgtgaggat tcatgggcta     1860
ttatagatga aaactgcaca aggccagaac cagcaggcac tcaataaacg ttcatgtcct     1920
ttttctctaa aaaaaaaaaa aaaaaa                                          1946
```

<210> SEQ ID NO 40
<211> LENGTH: 398
<212> TYPE: PRT
<213> ORGANISM: Homo sapiens

<400> SEQUENCE: 40

```
Met Ser Glu Gly Asn Ala Ala Gly Glu Pro Ser Thr Pro Gly Gly Pro
 1               5                  10                  15

Arg Pro Leu Leu Thr Gly Ala Arg Gly Leu Ile Gly Arg Arg Pro Ala
                20                  25                  30

Pro Pro Leu Thr Pro Gly Arg Leu Pro Ser Ile Arg Ser Arg Asp Leu
            35                  40                  45

Thr Leu Gly Gly Val Lys Lys Lys Thr Phe Thr Pro Asn Ile Ile Ser
        50                  55                  60

Arg Lys Ile Lys Glu Glu Pro Lys Glu Glu Val Thr Val Lys Lys Glu
 65                  70                  75                  80

Lys Arg Glu Arg Asp Arg Asp Arg Gln Arg Glu Gly His Gly Arg Gly
                85                  90                  95

Arg Gly Arg Pro Glu Val Ile Gln Ser His Ser Ile Phe Glu Gln Gly
               100                 105                 110

Pro Ala Glu Met Met Lys Lys Lys Gly Asn Trp Asp Lys Thr Val Asp
           115                 120                 125

Val Ser Asp Met Gly Pro Ser His Ile Ile Asn Ile Lys Lys Glu Lys
```

```
                130                 135                 140
Arg Glu Thr Asp Glu Thr Lys Gln Ile Leu Arg Met Leu Glu Lys
145                 150                 155                 160

Asp Asp Phe Leu Asp Asp Pro Gly Leu Arg Asn Asp Thr Arg Asn Met
                165                 170                 175

Pro Val Gln Leu Pro Leu Ala His Ser Gly Trp Leu Phe Lys Glu Glu
            180                 185                 190

Asn Asp Glu Pro Asp Val Lys Pro Trp Leu Ala Gly Pro Lys Glu Glu
        195                 200                 205

Asp Met Glu Val Asp Ile Pro Ala Val Lys Val Lys Glu Glu Pro Arg
210                 215                 220

Asp Glu Glu Glu Glu Ala Lys Met Lys Ala Pro Pro Lys Ala Ala Arg
225                 230                 235                 240

Lys Thr Pro Gly Leu Pro Lys Asp Val Ser Val Ala Glu Leu Leu Arg
                245                 250                 255

Glu Leu Ser Leu Thr Lys Glu Glu Leu Leu Phe Leu Gln Leu Pro
            260                 265                 270

Asp Thr Leu Pro Gly Gln Pro Pro Thr Gln Asp Ile Lys Pro Ile Lys
        275                 280                 285

Thr Glu Val Gln Gly Glu Asp Gly Gln Val Val Leu Ile Lys Gln Glu
290                 295                 300

Lys Asp Arg Glu Ala Lys Leu Ala Glu Asn Ala Cys Thr Leu Ala Asp
305                 310                 315                 320

Leu Thr Glu Gly Gln Val Gly Lys Leu Leu Ile Arg Lys Ser Gly Arg
                325                 330                 335

Val Gln Leu Leu Leu Gly Lys Val Thr Leu Asp Val Thr Met Gly Thr
            340                 345                 350

Ala Cys Ser Phe Leu Gln Glu Leu Val Ser Val Gly Leu Gly Asp Ser
        355                 360                 365

Arg Thr Gly Glu Met Thr Val Leu Gly His Val Lys His Lys Leu Val
370                 375                 380

Cys Ser Pro Asp Phe Glu Ser Leu Leu Asp His Lys His Arg
385                 390                 395

<210> SEQ ID NO 41
<211> LENGTH: 2150
<212> TYPE: DNA
<213> ORGANISM: Homo sapiens

<400> SEQUENCE: 41
ctcgagccac gaaggcccg ctgtcctgtc tagcagatac ttgcacggtt tacagaaatt     60
cggtccctgg gtcgtgtcag gaaactggaa aaaggtcat aagcatgaag cgcagttcag    120
tttccagcgg tggtgctggc cgcctctcca tgcaggagtt aagatcccag gatgtaaata    180
aacaaggcct ctatccct caaaccaaag agaaaccaac ctttggaaag ttgagtataa    240
acaaaccgac atctgaaaga aaagtctcgc tatttggcaa agaactagt ggacatggat    300 cccggaatag tcaacttggt atattttcca gttctgagaa aatcaaggac ccgagaccac    360
ttaatgacaa agcattcatt cagcagtgta ttcgacaact ctgtgagttt cttacagaaa    420
atggttatgc acataatgtg tccatgaaat ctctacaagc tccctctgtt aaagacttcc    480
tgaagatctt cacatttctt tatggcttcc tgtgcccctc atacgaactt cctgacacaa    540
agtttgaaga gagggttcca agaatcttta agaccttgg gtatcctttt gcactatcca    600 aagctccat gtacacagtg ggggctcctc atacatggcc tcacattgtg gcagccttag    660
```

```
tttggctaat agactgcatc aagatacata ctgccatgaa agaaagctca cctttatttg    720
atgatgggca gccttgggga gaagaaactg aagatggaat tatgcataat aagttgtttt    780
tggactacac cataaaatgc tatgagagtt ttatgagtgg tgccgacagc tttgatgaga    840
tgaatgcaga gctgcagtca aaactgaagg atttatttaa tgtggatgct tttaagctgg    900
aatcattaga agcaaaaaac agagcattga atgaacagat tgcaagattg aacaagaaa     960 gagaaaaaga accgaatcgt ctagagtcgt tgagaaaact gaaggcttcc ttacaaggag   1020
atgttcaaaa gtatcaggca tacatgagca atttggagtc tcattcagcc attcttgacc   1080
agaaattaaa tggtctcaat gaggaaattg ctagagtaga actagaatgt gaaacaataa   1140
aacaggagaa cactcgacta cagaatatca ttgacaacca gaagtactca gttgcagaca   1200
ttgagcgaat aaatcatgaa agaaatgaat tgcagcagac tattaataaa ttaaccaagg   1260
acctggaagc tgaacaacag aagttgtgga atgaggagtt aaaatatgcc agaggcaaag   1320
aagcgattga aacacaatta gcagagtatc acaaattggc tagaaaatta aaacttattc   1380
ctaaaggtgc tgagaattcc aaaggttatg actttgaaat taagtttaat cccgaggctg   1440
gtgccaactg ccttgtcaaa tacagggctc aagtttatgt acctcttaag gaactcctga   1500
atgaaactga agaagaaatt aataaagccc taaataaaaa aatgggtttg gaggatactt   1560
tagaacaatt gaatgcaatg ataacagaaa gcaagagaag tgtgagaact ctgaaagaag   1620
aagttcaaaa gctggatgat ctttaccaac aaaaaattaa ggaagcagag aagaggatg    1680 aaaaatgtgc cagtgagctt gagtccttgg agaaacacag gcacctgcta gaaagtactg   1740
ttaaccaggg gctcagtgaa gctatgaatg aattagatgc tgttcagcgg gaataccaac   1800
tagttgtgca accacgact gaagaaagac gaaagtgggg aaataacttg caacgtctgt    1860
tagagatggt tgctacacat gttgggtctg tagagaaaca tcttgaggag cagattgcta   1920
aagttgatag agaatatgaa gaatgcatgt cagaagatct ctcggaaaat attaaagaga   1980
ttagagataa gtatgagaag aaagctactc taattaagtc ttctgaagaa tgaagataaa   2040
atgttgatca tgtatatata tccatagtga ataaaattgt ctcagtaaaa aaaaaaaaa    2100 aaaaaaaaaa aaaaaaaaaa aaaaaaaaaa aaaaaaaaaa aaaaaaaaa               2150
```

<210> SEQ ID NO 42
<211> LENGTH: 642
<212> TYPE: PRT
<213> ORGANISM: Homo sapiens

<400> SEQUENCE: 42

```
Met Lys Arg Ser Ser Val Ser Ser Gly Gly Ala Gly Arg Leu Ser Met
 1               5                  10                  15

Gln Glu Leu Arg Ser Gln Asp Val Asn Lys Gln Gly Leu Tyr Thr Pro
             20                  25                  30

Gln Thr Lys Glu Lys Pro Thr Phe Gly Lys Leu Ser Ile Asn Lys Pro
         35                  40                  45

Thr Ser Glu Arg Lys Val Ser Leu Phe Gly Lys Arg Thr Ser Gly His
     50                  55                  60

Gly Ser Arg Asn Ser Gln Leu Gly Ile Phe Ser Ser Glu Lys Ile
 65                  70                  75                  80

Lys Asp Pro Arg Pro Leu Asn Asp Lys Ala Phe Ile Gln Gln Cys Ile
                 85                  90                  95

Arg Gln Leu Cys Glu Phe Leu Thr Glu Asn Gly Tyr Ala His Asn Val
            100                 105                 110
```

-continued

```
Ser Met Lys Ser Leu Gln Ala Pro Ser Val Lys Asp Phe Leu Lys Ile
        115                 120                 125
Phe Thr Phe Leu Tyr Gly Phe Leu Cys Pro Ser Tyr Glu Leu Pro Asp
        130                 135                 140
Thr Lys Phe Glu Glu Val Pro Arg Ile Phe Lys Asp Leu Gly Tyr
145                 150                 155                 160
Pro Phe Ala Leu Ser Lys Ser Ser Met Tyr Thr Val Gly Ala Pro His
                    165                 170                 175
Thr Trp Pro His Ile Val Ala Ala Leu Val Trp Leu Ile Asp Cys Ile
                180                 185                 190
Lys Ile His Thr Ala Met Lys Glu Ser Ser Pro Leu Phe Asp Asp Gly
            195                 200                 205
Gln Pro Trp Gly Glu Glu Thr Glu Asp Gly Ile Met His Asn Lys Leu
        210                 215                 220
Phe Leu Asp Tyr Thr Ile Lys Cys Tyr Glu Ser Phe Met Ser Gly Ala
225                 230                 235                 240
Asp Ser Phe Asp Glu Met Asn Ala Glu Leu Gln Ser Lys Leu Lys Asp
                245                 250                 255
Leu Phe Asn Val Asp Ala Phe Lys Leu Glu Ser Leu Glu Ala Lys Asn
                260                 265                 270
Arg Ala Leu Asn Glu Gln Ile Ala Arg Leu Glu Gln Glu Arg Glu Lys
            275                 280                 285
Glu Pro Asn Arg Leu Glu Ser Leu Arg Lys Leu Lys Ala Ser Leu Gln
        290                 295                 300
Gly Asp Val Gln Lys Tyr Gln Ala Tyr Met Ser Asn Leu Glu Ser His
305                 310                 315                 320
Ser Ala Ile Leu Asp Gln Lys Leu Asn Gly Leu Asn Glu Glu Ile Ala
                325                 330                 335
Arg Val Glu Leu Glu Cys Glu Thr Ile Lys Gln Glu Asn Thr Arg Leu
            340                 345                 350
Gln Asn Ile Ile Asp Asn Gln Lys Tyr Ser Val Ala Asp Ile Glu Arg
        355                 360                 365
Ile Asn His Glu Arg Asn Glu Leu Gln Gln Thr Ile Asn Lys Leu Thr
    370                 375                 380
Lys Asp Leu Glu Ala Glu Gln Gln Lys Leu Trp Asn Glu Glu Leu Lys
385                 390                 395                 400
Tyr Ala Arg Gly Lys Glu Ala Ile Glu Thr Gln Leu Ala Glu Tyr His
                405                 410                 415
Lys Leu Ala Arg Lys Leu Lys Leu Ile Pro Lys Gly Ala Glu Asn Ser
            420                 425                 430
Lys Gly Tyr Asp Phe Glu Ile Lys Phe Asn Pro Glu Ala Gly Ala Asn
        435                 440                 445
Cys Leu Val Lys Tyr Arg Ala Gln Val Tyr Val Pro Leu Lys Glu Leu
    450                 455                 460
Leu Asn Glu Thr Glu Glu Ile Asn Lys Ala Leu Asn Lys Lys Met
465                 470                 475                 480
Gly Leu Glu Asp Thr Leu Glu Gln Leu Asn Ala Met Ile Thr Glu Ser
                485                 490                 495
Lys Arg Ser Val Arg Thr Leu Lys Glu Val Gln Lys Leu Asp Asp
            500                 505                 510
Leu Tyr Gln Gln Lys Ile Lys Glu Ala Glu Glu Asp Glu Lys Cys
        515                 520                 525
```

```
Ala Ser Glu Leu Glu Ser Leu Glu Lys His Lys His Leu Leu Glu Ser
    530                 535                 540

Thr Val Asn Gln Gly Leu Ser Glu Ala Met Asn Glu Leu Asp Ala Val
545                 550                 555                 560

Gln Arg Glu Tyr Gln Leu Val Val Gln Thr Thr Thr Glu Glu Arg Arg
                565                 570                 575

Lys Val Gly Asn Asn Leu Gln Arg Leu Leu Glu Met Val Ala Thr His
                580                 585                 590

Val Gly Ser Val Glu Lys His Leu Glu Glu Gln Ile Ala Lys Val Asp
            595                 600                 605

Arg Glu Tyr Glu Glu Cys Met Ser Glu Asp Leu Ser Glu Asn Ile Lys
    610                 615                 620

Glu Ile Arg Asp Lys Tyr Glu Lys Lys Ala Thr Leu Ile Lys Ser Ser
625                 630                 635                 640

Glu Glu
```

<210> SEQ ID NO 43
<211> LENGTH: 3398
<212> TYPE: DNA
<213> ORGANISM: Homo sapiens

<400> SEQUENCE: 43

| | | |
|---|---|---|
| cgctgtcgcc gccagtagca gccttcgcca gcagcgccgc ggcggaaccg ggcgcagggg | 60 |
| agcgagcccg gccccgccag cccagcccag cccagcccta ctccctcccc acgccagggc | 120 |
| agcagccgtt gctcagagag aaggtggagg aagaaatcca gacctagca cgcgcgcacc | 180 |
| atcatggacc attatgattc tcagcaaacc aacgattaca tgcagccaga agaggactgg | 240 |
| gaccgggacc tgctcctgga cccggcctgg gagaagcagc agagaaagac attcacggca | 300 |
| tggtgtaact cccacctccg gaaggcgggg acacagatcg agaacatcga gaggacttc | 360 |
| cgggatggcc tgaagctcat gctgctgctg gaggtcatct caggtgaacg cttggccaag | 420 |
| ccagagcgag gcaagatgag agtgcacaag atctccaacg tcaacaaggc cctggatttc | 480 |
| atagccagca aaggcgtcaa actggtgtcc atcggagccg aagaaatcgt ggatgggaat | 540 |
| gtgaagatga ccctgggcat gatctggacc atcatcctgc gctttgccat ccaggacatc | 600 |
| tccgtggaag agacttcagc caaggaaggg ctgctcctgt ggtgtcagag aaagacagcc | 660 |
| ccttacaaaa atgtcaacat ccagaacttc cacataagct ggaaggatgg cctcggcttc | 720 |
| tgtgctttga tccaccgaca ccggcccgag ctgattgact acgggaagct gcggaaggat | 780 |
| gatccactca caaatctgaa tacggctttt gacgtggcag agaagtacct ggacatcccc | 840 |
| aagatgctgg atgccgaaga catcgttgga actgcccgac cggatgagaa agccatcatg | 900 |
| acttacgtgt ctagcttcta ccacgccttc tctggagccc agaaggcgga gacagcagcc | 960 |
| aatcgcatct gcaaggtgtt ggccgtcaac caggagaacg agcagcttat ggaagactac | 1020 |
| gagaagctgg ccagtgatct gttggagtgg atccgccgca caatcccgtg gctggagaac | 1080 |
| cgggtgcccg agaacaccat gcatgccatg aacagaagc tggaggactt ccgggactac | 1140 |
| cggcgcctgc acaagccgcc caaggtgcag gagaagtgcc agctggagat caacttcaac | 1200 |
| acgctgcaga ccaagctgcg gctcagcaac cggcctgcct tcatgccctc tgagggcagg | 1260 |
| atggtctcgg acatcaacaa tgcctggggc tgcctggagc aggtggagaa gggctatgag | 1320 |
| gagtggttgc tgaatgagat ccggaggctg agcgactgg accacctggc agaagttc | 1380 |
| cggcagaagg cctccatcca cgaggcctgg actgacggca agaggccat gctgcgacag | 1440 |

```
aaggactatg agaccgccac cctctcggag atcaaggccc tgctcaagaa gcatgaggcc    1500
ttcgagagtg acctggctgc ccaccaggac cgtgtggagc agattgccgc catcgcacag    1560
gagctcaatg agctggacta ttatgactca cccagtgtca acgcccgttg ccaaaagatc    1620
tgtgaccagt ggggacaatct gggggcccta actcagaagc gaagggaagc tctggagcgg    1680
accgagaaac tgctggagac cattgaccag ctgtacttgg agtatgccaa gcgggctgca    1740
cccttcaaca actggatgga gggggccatg gaggacctgc aggacacctt cattgtgcac    1800
accattgagg atccagggg actgaccaca gcccatgagc agttcaaggc caccctccct    1860
gatgccgaca aggagcgcct ggccatcctg gcatccaca atgaggtgtc caagattgtc    1920
cagacctacc acgtcaatat ggcgggcacc aaccctaca caaccatcac gcctcaggag    1980
atcaatggca aatgggacca cgtgcggcag ctggtgcctc ggagggacca agctctgacg    2040
gaggagcatg cccgacagca gcacaatgag aggctacgca agcagtttgg agcccaggcc    2100
aatgtcatcg ggccctggat ccagaccaag atggaggaga tcgggaggat ctccattgag    2160
atgcatggga ccctggagga ccagctcagc cacctgcggc agtatgagaa gagcatcgtc    2220
aactacaagc caaagattga tcagctggag ggcgaccacc agctcatcca ggaggcgctc    2280
atcttcgaca caagcacacc caactacacc atggagcaca tccgtgtggg ctgggagcag    2340
ctgctcacca ccatcgccag gaccatcaat gaggtagaga accagatcct gacccgggat    2400
gccaagggca tcagccagga gcagatgaat gagttccggg cctccttcaa ccactttgac    2460
cgggatcact ccggcacact gggtcccgag gagttcaaag cctgcctcat cagcttgggt    2520
tatgatattg caacgacccc ccagggagaa gcagaatttg cccgcatcat gagcattgtg    2580 gacccccaacc gcctggggt agtgacattc caggccttca ttgacttcat gtcccgcgag    2640
acagccgaca cagatacagc agaccaagtc atggcttcct tcaagatcct ggctggggac    2700
aagaactaca ttaccatgga cgagctgcgc cgcgagctgc cacccgacca ggctgagtac    2760
tgcatcgcgc ggatggcccc ctacaccggc cccgactccg tgccaggtgc tctggactac    2820
atgtccttct ccacggcgct gtacggcgag agtgacctct aatccacccc gcccggccgc    2880
cctcgtcttg tgcgccgtgc cctgccttgc acctccgccg tcgcccatct cctgcctggg    2940
ttcggtttca gctcccagcc tccacccggg tgagctgggg cccacgtggc atcgatcctc    3000
cctgcccgcg aagtgacagt ttacaaaatt attttctgca aaaagaaaa aaagttacg    3060 ttaaaaacca aaaaactaca tattttatta tagaaaaagt attttttctc caccagacaa    3120
atggaaaaaa agaggaaaga ttaactattt gcaccgaaat gtcttgtttt gttgcgacat    3180
aggaaaataa ccaagcacaa agttatattc catccttttt actgattttt ttttcttcta    3240
tctgttccat ctgctgtatt catttctcca atctcatgtc catttggtg tgggagtcgg    3300 ggtagggggt actcttgtca aaaggcacat tggtgcgtgt gtgtttgcta gctcacttgt    3360
ccatgaaaat attttatgat attaaagaaa atcttttg                          3398
```

<210> SEQ ID NO 44
<211> LENGTH: 892
<212> TYPE: PRT
<213> ORGANISM: Homo sapiens

<400> SEQUENCE: 44

```
Met Asp His Tyr Asp Ser Gln Gln Thr Asn Asp Tyr Met Gln Pro Glu
 1               5                   10                  15

Glu Asp Trp Asp Arg Asp Leu Leu Leu Asp Pro Ala Trp Glu Lys Gln
             20                  25                  30
```

```
Gln Arg Lys Thr Phe Thr Ala Trp Cys Asn Ser His Leu Arg Lys Ala
            35                  40                  45

Gly Thr Gln Ile Glu Asn Ile Glu Glu Asp Phe Arg Asp Gly Leu Lys
        50                  55                  60

Leu Met Leu Leu Leu Glu Val Ile Ser Gly Glu Arg Leu Ala Lys Pro
65                  70                  75                  80

Glu Arg Gly Lys Met Arg Val His Lys Ile Ser Asn Val Asn Lys Ala
                85                  90                  95

Leu Asp Phe Ile Ala Ser Lys Gly Val Lys Leu Val Ser Ile Gly Ala
            100                 105                 110

Glu Glu Ile Val Asp Gly Asn Val Lys Met Thr Leu Gly Met Ile Trp
        115                 120                 125

Thr Ile Ile Leu Arg Phe Ala Ile Gln Asp Ile Ser Val Glu Glu Thr
    130                 135                 140

Ser Ala Lys Glu Gly Leu Leu Leu Trp Cys Gln Arg Lys Thr Ala Pro
145                 150                 155                 160

Tyr Lys Asn Val Asn Ile Gln Asn Phe His Ile Ser Trp Lys Asp Gly
                165                 170                 175

Leu Gly Phe Cys Ala Leu Ile His Arg His Arg Pro Glu Leu Ile Asp
            180                 185                 190

Tyr Gly Lys Leu Arg Lys Asp Asp Pro Leu Thr Asn Leu Asn Thr Ala
        195                 200                 205

Phe Asp Val Ala Glu Lys Tyr Leu Asp Ile Pro Lys Met Leu Asp Ala
    210                 215                 220

Glu Asp Ile Val Gly Thr Ala Arg Pro Asp Glu Lys Ala Ile Met Thr
225                 230                 235                 240

Tyr Val Ser Ser Phe Tyr His Ala Phe Ser Gly Ala Gln Lys Ala Glu
                245                 250                 255

Thr Ala Ala Asn Arg Ile Cys Lys Val Leu Ala Val Asn Gln Glu Asn
            260                 265                 270

Glu Gln Leu Met Glu Asp Tyr Glu Lys Leu Ala Ser Asp Leu Leu Glu
        275                 280                 285

Trp Ile Arg Arg Thr Ile Pro Trp Leu Glu Asn Arg Val Pro Glu Asn
    290                 295                 300

Thr Met His Ala Met Gln Gln Lys Leu Glu Asp Phe Arg Asp Tyr Arg
305                 310                 315                 320

Arg Leu His Lys Pro Pro Lys Val Gln Glu Lys Cys Gln Leu Glu Ile
                325                 330                 335

Asn Phe Asn Thr Leu Gln Thr Lys Leu Arg Leu Ser Asn Arg Pro Ala
            340                 345                 350

Phe Met Pro Ser Glu Gly Arg Met Val Ser Asp Ile Asn Asn Ala Trp
        355                 360                 365

Gly Cys Leu Glu Gln Val Glu Lys Gly Tyr Glu Glu Trp Leu Leu Asn
    370                 375                 380

Glu Ile Arg Arg Leu Glu Arg Leu Asp His Leu Ala Glu Lys Phe Arg
385                 390                 395                 400

Gln Lys Ala Ser Ile His Glu Ala Trp Thr Asp Gly Lys Glu Ala Met
                405                 410                 415

Leu Arg Gln Lys Asp Tyr Glu Thr Ala Thr Leu Ser Glu Ile Lys Ala
            420                 425                 430

Leu Leu Lys Lys His Glu Ala Phe Glu Ser Asp Leu Ala Ala His Gln
        435                 440                 445
```

```
Asp Arg Val Glu Gln Ile Ala Ala Ile Ala Gln Glu Leu Asn Glu Leu
450                 455                 460
Asp Tyr Tyr Asp Ser Pro Ser Val Asn Ala Arg Cys Gln Lys Ile Cys
465                 470                 475                 480
Asp Gln Trp Asp Asn Leu Gly Ala Leu Thr Gln Lys Arg Arg Glu Ala
                485                 490                 495
Leu Glu Arg Thr Glu Lys Leu Leu Glu Thr Ile Asp Gln Leu Tyr Leu
            500                 505                 510
Glu Tyr Ala Lys Arg Ala Ala Pro Phe Asn Asn Trp Met Glu Gly Ala
        515                 520                 525
Met Glu Asp Leu Gln Asp Thr Phe Ile Val His Thr Ile Glu Glu Ile
530                 535                 540
Gln Gly Leu Thr Thr Ala His Glu Gln Phe Lys Ala Thr Leu Pro Asp
545                 550                 555                 560
Ala Asp Lys Glu Arg Leu Ala Ile Leu Gly Ile His Asn Glu Val Ser
                565                 570                 575
Lys Ile Val Gln Thr Tyr His Val Asn Met Ala Gly Thr Asn Pro Tyr
            580                 585                 590
Thr Thr Ile Thr Pro Gln Glu Ile Asn Gly Lys Trp Asp His Val Arg
        595                 600                 605
Gln Leu Val Pro Arg Arg Asp Gln Ala Leu Thr Glu Glu His Ala Arg
610                 615                 620
Gln Gln His Asn Glu Arg Leu Arg Lys Gln Phe Gly Ala Gln Ala Asn
625                 630                 635                 640
Val Ile Gly Pro Trp Ile Gln Thr Lys Met Glu Glu Ile Gly Arg Ile
                645                 650                 655
Ser Ile Glu Met His Gly Thr Leu Glu Asp Gln Leu Ser His Leu Arg
            660                 665                 670
Gln Tyr Glu Lys Ser Ile Val Asn Tyr Lys Pro Lys Ile Asp Gln Leu
        675                 680                 685
Glu Gly Asp His Gln Leu Ile Gln Glu Ala Leu Ile Phe Asp Asn Lys
690                 695                 700
His Thr Asn Tyr Thr Met Glu His Ile Arg Val Gly Trp Glu Gln Leu
705                 710                 715                 720
Leu Thr Thr Ile Ala Arg Thr Ile Asn Glu Val Glu Asn Gln Ile Leu
                725                 730                 735
Thr Arg Asp Ala Lys Gly Ile Ser Gln Glu Gln Met Asn Glu Phe Arg
            740                 745                 750
Ala Ser Phe Asn His Phe Asp Arg Asp His Ser Gly Thr Leu Gly Pro
        755                 760                 765
Glu Glu Phe Lys Ala Cys Leu Ile Ser Leu Gly Tyr Asp Ile Gly Asn
770                 775                 780
Asp Pro Gln Gly Glu Ala Glu Phe Ala Arg Ile Met Ser Ile Val Asp
785                 790                 795                 800
Pro Asn Arg Leu Gly Val Val Thr Phe Gln Ala Phe Ile Asp Phe Met
                805                 810                 815
Ser Arg Glu Thr Ala Asp Thr Asp Thr Ala Asp Gln Val Met Ala Ser
            820                 825                 830
Phe Lys Ile Leu Ala Gly Asp Lys Asn Tyr Ile Thr Met Asp Glu Leu
        835                 840                 845
Arg Arg Glu Leu Pro Pro Asp Gln Ala Glu Tyr Cys Ile Ala Arg Met
850                 855                 860
Ala Pro Tyr Thr Gly Pro Asp Ser Val Pro Gly Ala Leu Asp Tyr Met
```

```
                865                 870                 875                 880
Ser Phe Ser Thr Ala Leu Tyr Gly Glu Ser Asp Leu
                      885                 890

<210> SEQ ID NO 45
<211> LENGTH: 2649
<212> TYPE: DNA
<213> ORGANISM: Homo sapiens

<400> SEQUENCE: 45
aggaggacct gggggtgtgg cagcgaggaa gggccgagcc acggactgtg gggccgaaac      60
tcgctcccgc ccacccttc tcgaggctgt ggcctccgcg agagccgagc gggccgcacc     120
gccggccgtg cgactgcccc agtcagacac gaccccggct tctagcccgc ctaagcctgt     180
ttggggttgc tgactcgttt cctccccgag tttcccgcgg gaactaactc ttcaagagga     240
ccaaccgcag cccagagctt cgcagacccg gccaaccaga ggcgaggttg agagcccggc     300
gggccgcggg gagagagcgt cccatctgtc ctggaaagcc tgggcgggtg gattgggacc     360
ccgagagaag caggggagct cggcggggtg cagaagtgcc caggcccctc cccgctgggg     420
ttgggagctt gggcaggcca gcttcaccct tcctaagtcc gcttctggtc tccgggccca     480
gcctcggcca ccatgtcccg ccagaccacc tctgtgggct ccagctgcct ggacctgtgg     540
agggaaaaga atgaccggct cgttcgacag gccaaggtgg ctcagaactc cggtctgact     600
ctgaggcgac agcagttggc tcaggatgca ctggaagggc tcagagggct cctccatagt     660
ctgcaagggc tccctgcagc tgttcctgtt cttcccttgg agctgactgt cacctgcaac     720
ttcattatcc tgagggcaag cttggcccag ggtttcacag aggatcaggc ccaggatatc     780
cagcggagcc tagagagagt gctggagaca caggagcagc aggggcccag gttggaacag     840
gggctcaggg agctgtggga ctctgtcctt cgtgcttcct gccttctgcc ggagctgctg     900
tctgccctgc accgctggt tggcctgcag gctgccctct ggttgagtgc tgaccgtctt     960
ggggacctgg ccttgttact agagaccctg aatggcagcc agagtggagc ctctaaggat    1020
ctgctgttac ttctgaaaac ttggagtccc ccagctgagg aattagatgc tccattgacc    1080
ctgcaggatg cccagggatt gaaggatgtc ctcctgacag catttgccta ccgccaaggt    1140
ctccaggagc tgatcacagg gaacccagac aaggcactaa gcagccttca tgaagcggcc    1200
tcaggcctgt gtccacggcc tgtgttggtc caggtgtaca cagcactggg gtcctgtcac    1260
cgtaagatgg gaaatccaca gagagcactg ttgtacttgg ttgcagccct gaaagaggga    1320
tcagcctggg gtcctccact tctggaggcc tctaggctct atcagcaact gggggacaca    1380
acagcagagc tggagagtct ggagctgcta gttgaggcct tgaatgtccc atgcagttcc    1440
aaagccccgc agtttctcat tgaggtagaa ttactactgc caccacctga cctagcctca    1500
ccccttcatt gtggcactca gagccagacc aagcacatac tagcaagcag gtgcctacag    1560
acggggaggg caggagacgc tgcagagcat tacttggacc tgctggccct gttgctggat    1620
agctcggagc caaggttctc cccaccccc tccctccag ggccctgtat gcctgaggtg    1680
tttttggagg cagcggtagc actgatccag gcaggcagag cccaagatgc cttgactcta    1740
tgtgaggagt tgctcagccg cacatcatct ctgctaccca gatgtcccg gctgtgggaa    1800 gatgccagaa aaggaaccaa ggaactgcca tactgcccac tctgggtctc tgccacccac    1860
ctgcttcagg gccaggcctg ggttcaactg ggtgcccaaa aagtggcaat tagtgaattt    1920
agcaggtgcc tcgagctgct cttccgggcc acacctgagg aaaaagaaca agggcagct    1980
```

-continued

```
ttcaactgtg agcagggatg taagtcagat gcggcactgc agcagcttcg ggcagccgcc    2040
ctaattagtc gtggactgga atgggtagcc agcggccagg ataccaaagc cttacaggac    2100
ttcctcctca gtgtgcagat gtgcccaggt aatcgagaca cttactttca cctgcttcag    2160
actctgaaga ggctagatcg gagggatgag gccactgcac tctggtggag gctggaggcc    2220
caaactaagg ggtcacatga agatgctctg tggtctctcc ccctgtacct agaaagctat    2280
ttgagctgga tccgtccctc tgatcgtgac gccttccttg aagaatttcg acatctctg     2340 ccaaagtctt gtgacctgta gctgccacgt tttgaagagc ttgagctggg tccccagtgg    2400
gctgtctctc tgtggggagg gctttctgct tcaccatcat taggaatgtg accattccta    2460
tataattcct ggactggtga gattggtggt aggcctgtga aatttgccct agttactacc    2520
attctcgttt tggaggaaac aatctctgcc accaccaagt cattgacttt gctcgaggca    2580
ccttttttcc tgtttctcct tttctgttgt cgagtaaaat ttcatattta taaaaaaaa    2640 aaaaaaaaa                                                            2649
```

<210> SEQ ID NO 46
<211> LENGTH: 622
<212> TYPE: PRT
<213> ORGANISM: Homo sapiens

<400> SEQUENCE: 46

```
Met Ser Arg Gln Thr Thr Ser Val Gly Ser Cys Leu Asp Leu Trp
 1               5                  10                  15

Arg Glu Lys Asn Asp Arg Leu Val Arg Gln Ala Lys Val Ala Gln Asn
                20                  25                  30

Ser Gly Leu Thr Leu Arg Arg Gln Gln Leu Ala Gln Asp Ala Leu Glu
            35                  40                  45

Gly Leu Arg Gly Leu Leu His Ser Leu Gln Gly Leu Pro Ala Ala Val
        50                  55                  60

Pro Val Leu Pro Leu Glu Leu Thr Val Thr Cys Asn Phe Ile Ile Leu
    65                  70                  75                  80

Arg Ala Ser Leu Ala Gln Gly Phe Thr Glu Asp Gln Ala Gln Asp Ile
                85                  90                  95

Gln Arg Ser Leu Glu Arg Val Leu Glu Thr Gln Glu Gln Gly Pro
            100                 105                 110

Arg Leu Glu Gln Gly Leu Arg Glu Leu Trp Asp Ser Val Leu Arg Ala
        115                 120                 125

Ser Cys Leu Leu Pro Glu Leu Ser Ala Leu His Arg Leu Val Gly
    130                 135                 140

Leu Gln Ala Ala Leu Trp Leu Ser Ala Asp Arg Leu Gly Asp Leu Ala
145                 150                 155                 160

Leu Leu Leu Glu Thr Leu Asn Gly Ser Gln Ser Gly Ala Ser Lys Asp
                165                 170                 175

Leu Leu Leu Leu Lys Thr Trp Ser Pro Pro Ala Glu Glu Leu Asp
            180                 185                 190

Ala Pro Leu Thr Leu Gln Asp Ala Gln Gly Leu Lys Asp Val Leu Leu
        195                 200                 205

Thr Ala Phe Ala Tyr Arg Gln Gly Leu Gln Glu Leu Ile Thr Gly Asn
    210                 215                 220

Pro Asp Lys Ala Leu Ser Ser Leu His Glu Ala Ala Ser Gly Leu Cys
225                 230                 235                 240

Pro Arg Pro Val Leu Val Gln Val Tyr Thr Ala Leu Gly Ser Cys His
                245                 250                 255
```

```
Arg Lys Met Gly Asn Pro Gln Arg Ala Leu Leu Tyr Leu Val Ala Ala
            260                 265                 270

Leu Lys Glu Gly Ser Ala Trp Gly Pro Pro Leu Leu Glu Ala Ser Arg
        275                 280                 285

Leu Tyr Gln Gln Leu Gly Asp Thr Thr Ala Glu Leu Glu Ser Leu Glu
    290                 295                 300

Leu Leu Val Glu Ala Leu Asn Val Pro Cys Ser Ser Lys Ala Pro Gln
305                 310                 315                 320

Phe Leu Ile Glu Val Glu Leu Leu Pro Pro Asp Leu Ala Ser
                325                 330                 335

Pro Leu His Cys Gly Thr Gln Ser Gln Thr Lys His Ile Leu Ala Ser
                340                 345                 350

Arg Cys Leu Gln Thr Gly Arg Ala Gly Asp Ala Ala Glu His Tyr Leu
            355                 360                 365

Asp Leu Leu Ala Leu Leu Leu Asp Ser Ser Glu Pro Arg Phe Ser Pro
        370                 375                 380

Pro Pro Ser Pro Pro Gly Pro Cys Met Pro Glu Val Phe Leu Glu Ala
385                 390                 395                 400

Ala Val Ala Leu Ile Gln Ala Gly Arg Ala Gln Asp Ala Leu Thr Leu
                405                 410                 415

Cys Glu Glu Leu Leu Ser Arg Thr Ser Ser Leu Leu Pro Lys Met Ser
            420                 425                 430

Arg Leu Trp Glu Asp Ala Arg Lys Gly Thr Lys Glu Leu Pro Tyr Cys
        435                 440                 445

Pro Leu Trp Val Ser Ala Thr His Leu Leu Gln Gly Gln Ala Trp Val
    450                 455                 460

Gln Leu Gly Ala Gln Lys Val Ala Ile Ser Glu Phe Ser Arg Cys Leu
465                 470                 475                 480

Glu Leu Leu Phe Arg Ala Thr Pro Glu Glu Lys Glu Gln Gly Ala Ala
                485                 490                 495

Phe Asn Cys Glu Gln Gly Cys Lys Ser Asp Ala Ala Leu Gln Gln Leu
            500                 505                 510

Arg Ala Ala Ala Leu Ile Ser Arg Gly Leu Glu Trp Val Ala Ser Gly
        515                 520                 525

Gln Asp Thr Lys Ala Leu Gln Asp Phe Leu Leu Ser Val Gln Met Cys
    530                 535                 540

Pro Gly Asn Arg Asp Thr Tyr Phe His Leu Leu Gln Thr Leu Lys Arg
545                 550                 555                 560

Leu Asp Arg Arg Asp Glu Ala Thr Ala Leu Trp Trp Arg Leu Glu Ala
                565                 570                 575

Gln Thr Lys Gly Ser His Glu Asp Ala Leu Trp Ser Leu Pro Leu Tyr
            580                 585                 590

Leu Glu Ser Tyr Leu Ser Trp Ile Arg Pro Ser Asp Arg Asp Ala Phe
        595                 600                 605

Leu Glu Glu Phe Arg Thr Ser Leu Pro Lys Ser Cys Asp Leu
    610                 615                 620

<210> SEQ ID NO 47
<211> LENGTH: 2376
<212> TYPE: DNA
<213> ORGANISM: Homo sapiens

<400> SEQUENCE: 47
gaggaggagt ggggaccggg cggggggtgg aggaagaggc ctcgcgcaga ggagggagca      60
```

```
attgaatttc aaacacaaac aactcgacga gcgcgcaccc accgcgcggg agccttgccc      120
cgatccgcgc ccgccccgtc cgtgcggcgc gcgggcggag acgccgtggc cgcgccggag      180
ctcgggccgg gggccaccat cgaggcgggg ccgcgcgag ggccggagcg gagcggcgcc       240
gccaccgccg cacgcgcaaa cttgggctcg cgcttccgg cccggcgcgg agcccggggc       300
gcccggagcc ccgccatgtc gcgatccaac cggcagaagg agtacaaatg cggggacctg      360
gtgttcgcca agatgaaggg ctacccacac tggccggccc ggattgacga gatgcctgag      420
gctgccgtga aatcaacagc caacaaatac caagtctttt ttttcgggac ccacgagacg      480
gcattcctgg gccccaaaga cctcttccct tacgaggaat ccaaggagaa gtttggcaag      540
cccaacaaga ggaaagggtt cagcgagggg ctgtgggaga tcgagaacaa ccctactgtc      600
aaggcttccg gctatcagtc ctcccagaaa aagagctgtg tggaagagcc tgaaccagag      660
cccgaagctg cagagggtga cggtgataag aaggggaatg cagagggcag cagcgacgag      720
gaagggaagc tggtcattga tgagccagcc aaggagaaga acgagaaagg agcgttgaag      780
aggagagcag gggacttgct ggaggactct cctaaacgtc ccaaggaggc agaaaacccct    840 gaaggagagg agaaggaggc agccaccttg gaggttgaga ggccccttcc tatggaggtg      900
gaaaagaata gcaccccctc tgagcccggc tctggccggg ggcctcccca agaggaagaa      960
gaagaggagg atgaagagga gaggctacc aaggaagatg ctgaggcccc aggcatcaga      1020
gatcatgaga gcctgtagcc accaatgttt caagaggagc ccccaccctg ttcctgctgc      1080
tgtctgggtg ctactgggga aactggccat ggcctgcaaa ctgggaaccc ctttcccacc      1140
ccaacctgct ctcctcttct actcacttt cccactccaa gcccagccca tggagattga      1200
cctggatggg gcaggccacc tggctctcac ctctaggtcc ccatactcct atgatctgag      1260
tcagagccat gtcttctccc tggaatgagt tgaggccact gtgttccttc cgcttggagc      1320 tatttttccag gcttctgctg gggcctggga caactgctcc cacctcctga caccccttctc    1380 ccactctcct aggcattctg gacctctggg ttgggatcag gggtaggaat ggaaggatgg      1440
agcatcaaca gcagggtggg cttgtggggc ctggagggg caatcctcaa atgcggggtg       1500
ggggcagcac aggagggcgg cctccttctg agctcctgtc ccctgctaca cctattatcc      1560
cagctgccta gattcaggga aagtgggaca gcttgtaggg gagggctcc tttccataaa       1620 tccttgatga ttgacaacac ccattttcc ttttgccgac cccaagagtt ttgggagttg      1680
tagttaatca tcaagagaat ttggggcttc caagttgttc gggccaagga cctgagacct     1740
gaagggttga ctttacccat ttgggtggga gtgttgagca tctgtccccc tttagatctc     1800
tgaagccaca aataggatgc ttgggaagac tcctagctgt cctttttcct ctccacacag     1860
tgctcaaggc cagcttatag tcatatatat cacccagaca taaggaaaa gacacatttt     1920 ttaggaaatg tttttaataa aagaaaatta caaaaaaaa ttttaaagac ccctaaccct     1980
ttgtgtgctc tccattctgc ccttcccca tcgttgcccc catttctgag gtgcactggg      2040
aggctcccct tctatttggg gcttgatgac tttcttttg tagctgggc tttgatgttc       2100 cttccagtgt catttctcat ccacataccc tgacctggcc ccctcagtgt tgtcaccaga      2160
tctgatttgt aacccactga gaggacagag agaaataagt gccctctccc accctcttcc     2220
tactggtctc tctatgcctc tctacagtct cgtctctttt accctggccc ctctcccttg     2280
ggctctgatg aaaattgct gactgtagct ttggaagttt agctctgaga accgtagatg      2340
atttcagttc taggaaaata aaacccgttg attact                               2376
```

<210> SEQ ID NO 48
<211> LENGTH: 240
<212> TYPE: PRT
<213> ORGANISM: Homo sapiens

<400> SEQUENCE: 48

```
Met Ser Arg Ser Asn Arg Gln Lys Glu Tyr Lys Cys Gly Asp Leu Val
 1               5                  10                  15

Phe Ala Lys Met Lys Gly Tyr Pro His Trp Pro Ala Arg Ile Asp Glu
             20                  25                  30

Met Pro Glu Ala Ala Val Lys Ser Thr Ala Asn Lys Tyr Gln Val Phe
         35                  40                  45

Phe Phe Gly Thr His Glu Thr Ala Phe Leu Gly Pro Lys Asp Leu Phe
     50                  55                  60

Pro Tyr Glu Glu Ser Lys Glu Lys Phe Gly Lys Pro Asn Lys Arg Lys
 65                  70                  75                  80

Gly Phe Ser Glu Gly Leu Trp Glu Ile Glu Asn Asn Pro Thr Val Lys
                 85                  90                  95

Ala Ser Gly Tyr Gln Ser Ser Gln Lys Lys Ser Cys Val Glu Glu Pro
            100                 105                 110

Glu Pro Glu Pro Glu Ala Ala Glu Gly Asp Gly Asp Lys Lys Gly Asn
        115                 120                 125

Ala Glu Gly Ser Ser Asp Glu Glu Gly Lys Leu Val Ile Asp Glu Pro
    130                 135                 140

Ala Lys Glu Lys Asn Glu Lys Gly Ala Leu Lys Arg Arg Ala Gly Asp
145                 150                 155                 160

Leu Leu Glu Asp Ser Pro Lys Arg Pro Lys Glu Ala Glu Asn Pro Glu
                165                 170                 175

Gly Glu Glu Lys Glu Ala Ala Thr Leu Glu Val Glu Arg Pro Leu Pro
            180                 185                 190

Met Glu Val Glu Lys Asn Ser Thr Pro Ser Glu Pro Gly Ser Gly Arg
        195                 200                 205

Gly Pro Pro Gln Glu Glu Glu Glu Glu Asp Glu Glu Glu Ala
    210                 215                 220

Thr Lys Glu Asp Ala Glu Ala Pro Gly Ile Arg Asp His Glu Ser Leu
225                 230                 235                 240
```

<210> SEQ ID NO 49
<211> LENGTH: 4160
<212> TYPE: DNA
<213> ORGANISM: Homo sapiens

<400> SEQUENCE: 49

```
gcgcttgcgg aggattgcgt tgacgagact cttatttatt gtcaccaacc tgtggtggaa      60
tttgcagttg cacattggat ctgattcgcc ccgccccgaa tgcgcctgc ccggaggcag      120 tgaaagtaca gccgcgccgc cccaagtcag cctggacaca taatcagca gcggccgga      180 gaaccccgca atctctgcgc ccacaaaata caccgacgat gcccgatcta ctttaagggc      240
tgaaacccac gggcctgaga gactataaga gcgttcccta ccgccatgga caacggga       300 cagaacgccc cggccgcttc ggggccccgg aaaaggcacg gcccaggacc cagggaggcg      360
cggggagcca ggcctgggct ccgggtcccc aagacccttg tgctcgttgt cgccgcggtc      420
ctgctgttgg tctcagctga gtctgctctg atcacccaac aagacctagc tccccagcag      480
agagcggccc cacaacaaaa gaggtccagc ccctcagagg gattgtgtcc acctggacac      540
```

```
catatctcag aagacggtag agattgcatc tcctgcaaat atggacagga ctatagcact    600
cactggaatg acctccttt ctgcttgcgc tgcaccaggt gtgattcagg tgaagtggag     660
ctaagtccct gcaccacgac cagaaacaca gtgtgtcagt gcgaagaagg caccttccgg    720
gaagaagatt ctcctgagat gtgccggaag tgccgcacag ggtgtcccag agggatggtc    780
aaggtcggtg attgtacacc ctggagtgac atcgaatgtg tccacaaaga atcaggtaca    840
aagcacagtg gggaagcccc agctgtggag agacggtga cctccagccc agggactcct     900
gcctctccct gttctctctc aggcatcatc ataggagtca cagttgcagc cgtagtcttg    960
attgtggctg tgtttgtttg caagtcttta ctgtggaaga aagtccttcc ttacctgaaa    1020
ggcatctgct caggtggtgg tggggaccct gagcgtgtgg acagaagctc acaacgacct    1080
ggggctgagg acaatgtcct caatgagatc gtgagtatct tgcagcccac ccaggtccct    1140
gagcaggaaa tggaagtcca ggagccagca gagccaacag gtgtcaacat gttgtccccc    1200
ggggagtcag agcatctgct ggaaccggca gaagctgaaa ggtctcagag gaggaggctg    1260
ctggttccag caaatgaagg tgatcccact gagactctga cagtgcttt cgatgacttt     1320 gcagacttgg tgccctttga ctcctgggag ccgctcatga ggaagttggg cctcatggac    1380
aatgagataa aggtggctaa agctgaggca gcgggccaca gggacacctt gtacacgatg    1440
ctgataaagt gggtcaacaa aaccgggcga gatgcctctg tccacaccct gctggatgcc    1500
ttggagacgc tgggagagag acttgccaag cagaagattg aggaccactt gttgagctct    1560
ggaaagttca tgtatctaga aggtaatgca gactctgcca tgtcctaagt gtgattctct    1620
tcaggaagtc agaccttccc tggtttacct tttttctgga aaaagcccaa ctggactcca    1680
gtcagtagga aagtgccaca attgtcacat gaccggtact ggaagaaact ctcccatcca    1740 acatcacccca gtggatggaa catcctgtaa cttttcactg cacttggcat tatttttata   1800
agctgaatgt gataataagg acactatgga aatgtctgga tcattccgtt tgtgcgtact    1860
ttgagatttg gtttgggatg tcattgtttt cacagcactt ttttatccta atgtaaatgc    1920
tttatttatt tatttgggct acattgtaag atccatctac acagtcgttg tccgacttca    1980
cttgatacta tatgatatga accttttttg ggtgggggt gcggggcagt tcactctgtc      2040
tcccaggctg gagtgcaatg gtgcaatctt ggctcactat agccttgacc tctcaggctc    2100
aagcgattct cccacctcag ccatccaaat agctgggacc acaggtgtgc accaccacgc    2160
ccggctaatt ttttgtattt tgtctagata tagggctct ctatgttgct cagggtggtc     2220
tcgaattcct ggactcaagc agtctgccca cctcagactc ccaaagcggt ggaattagag    2280
gcgtgagccc ccatgcttgg ccttaccttt ctacttttat aattctgtat gttattattt    2340
tatgaacatg aagaaacttt agtaaatgta cttgtttaca tagttatgtg aatagattag    2400
ataaacataa aaggaggaga catacaatgg gggaagaaga agaagtcccc tgtaagatgt    2460
cactgtctgg gttccagccc tccctcagat gtactttggc ttcaatgatt ggcaacttct    2520
acagggccca gtcttttgaa ctggacaacc ttacaagtat atgagtatta tttataggta    2580
gttgtttaca tatgagtcgg gaccaaagag aactggatcc acgtgaagtc ctgtgtgtgg    2640
ctggtcccta cctgggcagt ctcatttgca cccatagccc ccatctatgg acaggctggg    2700
acagaggcag atgggttaga tcacacataa caatagggtc tatgtcatat cccaagtgaa    2760
cttgagccct gtttgggctc aggagataga agacaaaatc tgtctcccac gtctgccatg    2820
gcatcaaggg ggaagagtag atggtgcttg agaatggtgt gaaatggttg ccatctcagg    2880
agtagatggc ccggctcact tctggttatc tgtcaccctg agcccatgag ctgccttta    2940
```

-continued

```
gggtacagat tgcctacttg aggaccttgg ccgctctgta agcatctgac tcatctcaga    3000
aatgtcaatt cttaaacact gtggcaacag gacctagaat ggctgacgca ttaaggtttt    3060
cttcttgtgt cctgttctat tattgtttta agacctcagt aaccatttca gcctctttcc    3120
agcaaaccct tctccatagt atttcagtca tggaaggatc atttatgcag gtagtcattc    3180
caggagtttt tggtcttttc tgtctcaagg cattgtgtgt tttgttccgg gactggtttg    3240
ggtgggacaa agttagaatt gcctgaagat cacacattca gactgttgtg tctgtggagt    3300
tttaggagtg gggggtgacc tttctggtct ttgcacttcc atcctctccc acttccatct    3360
ggcatcccac gcgttgtccc ctgcacttct ggaaggcaca gggtgctgct gcctcctggt    3420
ctttgccttt gctgggcctt ctgtgcagga cgctcagcct cagggctcag aaggtgccag    3480
tccggtccca ggtccttgt cccttccaca gaggccttcc tagaagatgc atctagagtg     3540
tcagccttat cagtgtttaa gatttgtctt ttatttttaa ttttttttgag acagaatctc   3600 actctctcgc ccaggctgga gtgcaacggt acgatcttgg ctcagtgcaa cctccgcctc   3660
ctgggttcaa gcgattctcg tgcctcagcc tccggagtag ctgggattgc aggcacccgc   3720
caccacgcct ggctaatttt tgtatttta gtagagacgg ggtttcacca tgttggtcag   3780
gctggtctcg aactcctgac ctcaggtgat ccaccttggc ctccgaaagt gctgggatta   3840
caggcgtgag ccaccagcca ggccaagcta ttcttttaaa gtaagcttcc tgacgacatg   3900
aaataattgg gggttttgtt gtttagttac attaggcttt gctatatccc caggccaaat   3960
agcatgtgac acaggacagc catagtatag tgtgtcactc gtggttggtg tcctttcatg   4020
cttctgccct gtcaaaggtc cctatttgaa atgtgttata atacaaacaa ggaagcacat   4080
tgtgtacaaa atacttatgt atttatgaat ccatgaccaa attaaatatg aaaccttata   4140 taaaaaaaa aaaaaaaaa                                                  4160
```

<210> SEQ ID NO 50
<211> LENGTH: 440
<212> TYPE: PRT
<213> ORGANISM: Homo sapiens

<400> SEQUENCE: 50

```
Met Glu Gln Arg Gly Gln Asn Ala Pro Ala Ala Ser Gly Ala Arg Lys
 1               5                  10                  15

Arg His Gly Pro Gly Pro Arg Glu Ala Arg Gly Ala Arg Pro Gly Leu
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
```

```
                145                 150                 155                 160
        Pro Arg Gly Met Val Lys Val Gly Asp Cys Thr Pro Trp Ser Asp Ile
                        165                 170                 175
        Glu Cys Val His Lys Glu Ser Gly Thr Lys His Ser Gly Glu Ala Pro
                    180                 185                 190
        Ala Val Glu Glu Thr Val Thr Ser Ser Pro Gly Thr Pro Ala Ser Pro
                    195                 200                 205
        Cys Ser Leu Ser Gly Ile Ile Ile Gly Val Thr Val Ala Ala Val Val
                210                 215                 220
        Leu Ile Val Ala Val Phe Val Cys Lys Ser Leu Leu Trp Lys Lys Val
        225                 230                 235                 240
        Leu Pro Tyr Leu Lys Gly Ile Cys Ser Gly Gly Gly Asp Pro Glu
                        245                 250                 255
        Arg Val Asp Arg Ser Ser Gln Arg Pro Gly Ala Glu Asp Asn Val Leu
                    260                 265                 270
        Asn Glu Ile Val Ser Ile Leu Gln Pro Thr Gln Val Pro Glu Gln Glu
                    275                 280                 285
        Met Glu Val Gln Glu Pro Ala Glu Pro Thr Gly Val Asn Met Leu Ser
                290                 295                 300
        Pro Gly Glu Ser Glu His Leu Leu Glu Pro Ala Glu Ala Glu Arg Ser
        305                 310                 315                 320
        Gln Arg Arg Arg Leu Leu Val Pro Ala Asn Glu Gly Asp Pro Thr Glu
                        325                 330                 335
        Thr Leu Arg Gln Cys Phe Asp Asp Phe Ala Asp Leu Val Pro Phe Asp
                    340                 345                 350
        Ser Trp Glu Pro Leu Met Arg Lys Leu Gly Leu Met Asp Asn Glu Ile
                    355                 360                 365
        Lys Val Ala Lys Ala Glu Ala Ala Gly His Arg Asp Thr Leu Tyr Thr
                370                 375                 380
        Met Leu Ile Lys Trp Val Asn Lys Thr Gly Arg Asp Ala Ser Val His
        385                 390                 395                 400
        Thr Leu Leu Asp Ala Leu Glu Thr Leu Gly Glu Arg Leu Ala Lys Gln
                        405                 410                 415
        Lys Ile Glu Asp His Leu Leu Ser Ser Gly Lys Phe Met Tyr Leu Glu
                    420                 425                 430
        Gly Asn Ala Asp Ser Ala Met Ser
                    435                 440

<210> SEQ ID NO 51
<211> LENGTH: 4073
<212> TYPE: DNA
<213> ORGANISM: Homo sapiens

<400> SEQUENCE: 51
gcgcttgcgg aggattgcgt tgacgagact cttatttatt gtcaccaacc tgtggtggaa        60
tttgcagttg cacattggat ctgattcgcc ccgccccgaa tgacgcctgc ccggaggcag       120
tgaaagtaca gccgcgccgc cccaagtcag cctggacaca taatcagca cgcggccgga        180 gaacccgca atctctgcgc ccacaaaata caccgacgat gcccgatcta ctttaagggc       240
tgaaacccac gggcctgaga gactataaga gcgttcccta ccgccatgga caacggggga       300
cagaacgccc cggccgcttc ggggccccgg aaaaggcacg cccaggacc agggaggcg        360 cggggagcca ggcctgggct ccgggtcccc aagaccttg tgctcgttgt cgccgcggtc       420
ctgctgttgg tctcagctga gtctgctctg atcacccaac aagacctagc tccccagcag       480
```

-continued

```
agagcggccc cacaacaaaa gaggtccagc ccctcagagg gattgtgtcc acctggacac    540
catatctcag aagacggtag agattgcatc tcctgcaaat atggacagga ctatagcact    600
cactggaatg acctcctttt ctgcttgcgc tgcaccaggt gtgattcagg tgaagtggag    660
ctaagtccct gcaccacgac cagaaacaca gtgtgtcagt gcgaagaagg caccttccgg    720
gaagaagatt ctcctgagat gtgccggaag tgccgcacag ggtgtcccag agggatggtc    780
aaggtcggtg attgtacacc ctggagtgac atcgaatgtg tccacaaaga atcaggcatc    840
atcataggag tcacagttgc agccgtagtc ttgattgtgg ctgtgtttgt ttgcaagtct    900
ttactgtgga agaaagtcct tccttacctg aaaggcatct gctcaggtgg tggtggggac    960
cctgagcgtg tggacagaag ctcacaacga cctggggctg aggacaatgt cctcaatgag   1020
atcgtgagta tcttgcagcc cacccaggtc cctgagcagg aaatggaagt ccaggagcca   1080
gcagagccaa caggtgtcaa catgttgtcc ccgggggagt cagagcatct gctggaaccg   1140
gcagaagctg aaaggtctca gaggaggagg ctgctggttc agcaaatgaa ggtgatccc    1200 actgagactc tgagacagtg cttcgatgac tttgcagact tggtgccctt tgactcctgg   1260
gagccgctca tgaggaagtt gggcctcatg gacaatgaga taaaggtggc taaagctgag   1320
gcagcgggcc acagggacac cttgtacacg atgctgataa agtgggtcaa caaaaccggg   1380
cgagatgcct ctgtccacac cctgctggat gccttggaga cgctgggaga gagacttgcc   1440
aagcagaaga ttgaggacca cttgttgagc tctggaaagt tcatgtatct agaaggtaat   1500
gcagactctg ccatgtccta agtgtgattc tcttcaggaa gtcagacctt ccctggttta   1560 cctttttttct ggaaaaagcc caactggact ccagtcagta ggaaagtgcc acaattgtca   1620
catgaccggt actggaagaa actctcccat ccaacatcac ccagtggatg aacatcctg    1680 taactttca ctgcacttgg cattatttt ataagctgaa tgtgataata aggacactat   1740
ggaaatgtct ggatcattcc gtttgtgcgt actttgagat ttggtttggg atgtcattgt   1800
tttcacagca cttttttatc ctaatgtaaa tgctttattt atttatttgg ctacattgt    1860 aagatccatc tacacagtcg ttgtccgact tcacttgata ctatatgata tgaacctttt   1920
ttgggtgggg ggtgcggggc agttcactct gtctcccagg ctggagtgca atggtgcaat   1980
cttggctcac tatagccttg acctctcagg ctcaagcgat tctcccacct cagccatcca   2040
aatagctggg accacaggtg tgcaccacca cgcccggcta attttttgta ttttgtctag   2100
atataggggc tctctatgtt gctcagggtg gtctcgaatt cctggactca agcagtctgc   2160
ccacctcaga ctcccaaagc ggtggaatta gaggcgtgag ccccatgct tggccttacc    2220 tttctactt tataattctg tatgttatta ttttatgaac atgaagaaac tttagtaaat    2280
gtacttgttt acatagttat gtgaatagat tagataaaca taaaaggagg agacatacaa   2340
tgggggaaga agaagaagtc ccctgtaaga tgtcactgtc tgggttccag ccctccctca   2400
gatgtacttt ggcttcaatg attggcaact tctacagggg ccagtctttt gaactggaca   2460
accttacaag tatatgagta ttatttatag gtagttgttt acatatgagt cgggaccaaa   2520
gagaactgga tccacgtgaa gtcctgtgtg tggctggtcc ctacctgggc agtctcattt   2580
gcacccatag cccccatcta tggacaggct gggacagagg cagatgggtt agatcacaca   2640
taacaatagg gtctatgtca tatcccaagt gaacttgagc cctgtttggg ctcaggagat   2700
agaagacaaa atctgtctcc cacgtctgcc atggcatcaa gggggaagag tagatggtgc   2760
ttgagaatgg tgtgaaatgg ttgccatctc aggagtagat ggcccggctc acttctggtt   2820
```

-continued

```
atctgtcacc ctgagcccat gagctgcctt ttagggtaca gattgcctac ttgaggacct    2880
tggccgctct gtaagcatct gactcatctc agaaatgtca attcttaaac actgtggcaa    2940
caggacctag aatggctgac gcattaaggt tttcttcttg tgtcctgttc tattattgtt    3000
ttaagacctc agtaaccatt tcagcctctt ccagcaaac ccttctccat agtatttcag     3060
tcatggaagg atcatttatg caggtagtca ttccaggagt ttttggtctt ttctgtctca    3120
aggcattgtg tgttttgttc cgggactggt ttgggtggga caaagttaga attgcctgaa    3180
gatcacacat tcagactgtt gtgtctgtgg agttttagga gtgggggtg accttctgg      3240
tctttgcact tccatcctct cccacttcca tctggcatcc cacgcgttgt ccctgcact     3300
tctggaaggc acagggtgct gctgcctcct ggtctttgcc tttgctgggc cttctgtgca    3360
ggacgctcag cctcagggct cagaaggtgc cagtccggtc ccaggtccct tgtcccttcc    3420
acagaggcct tcctagaaga tgcatctaga gtgtcagcct tatcagtgtt taagatttgt    3480
cttttatttt taattttttt gagacagaat ctcactctct cgcccaggct ggagtgcaac    3540
ggtacgatct tggctcagtg caacctccgc ctcctgggtt caagcgattc tcgtgcctca    3600
gcctccggag tagctgggat tgcaggcacc cgccaccacg cctggctaat ttttgtattt    3660
ttagtagaga cggggtttca ccatgttggt caggctggtc tcgaactcct gacctcaggt    3720
gatccacctt ggcctccgaa agtgctggga ttacaggcgt gagccaccag ccaggccaag    3780
ctattctttt aaagtaagct tcctgacgac atgaaataat tgggggtttt gttgtttagt    3840
tacattaggc tttgctatat ccccaggcca aatagcatgt gacacaggac agccatagta    3900
tagtgtgtca ctcgtggttg gtgtcctttc atgcttctgc cctgtcaaag gtccctattt    3960
gaaatgtgtt ataatacaaa caaggaagca cattgtgtac aaaatactta tgtatttatg    4020
aatccatgac caaattaaat atgaaacctt atataaaaaa aaaaaaaaaa aaa           4073
```

<210> SEQ ID NO 52
<211> LENGTH: 411
<212> TYPE: PRT
<213> ORGANISM: Homo sapiens

<400> SEQUENCE: 52

```
Met Glu Gln Arg Gly Gln Asn Ala Pro Ala Ser Gly Ala Arg Lys
 1               5                   10                  15

Arg His Gly Pro Gly Pro Arg Glu Ala Arg Gly Ala Arg Pro Gly Leu
                20                  25                  30

Arg Val Pro Lys Thr Leu Val Leu Val Ala Val Leu Leu Leu
            35                  40                  45

Val Ser Ala Glu Ser Ala Leu Ile Thr Gln Gln Asp Leu Ala Pro Gln
50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160
```

Pro Arg Gly Met Val Lys Val Gly Asp Cys Thr Pro Trp Ser Asp Ile
            165                 170                 175

Glu Cys Val His Lys Glu Ser Gly Ile Ile Ile Gly Val Thr Val Ala
            180                 185                 190

Ala Val Val Leu Ile Val Ala Val Phe Val Cys Lys Ser Leu Leu Trp
            195                 200                 205

Lys Lys Val Leu Pro Tyr Leu Lys Gly Ile Cys Ser Gly Gly Gly Gly
            210                 215                 220

Asp Pro Glu Arg Val Asp Arg Ser Ser Gln Arg Pro Gly Ala Glu Asp
225                 230                 235                 240

Asn Val Leu Asn Glu Ile Val Ser Ile Leu Gln Pro Thr Gln Val Pro
            245                 250                 255

Glu Gln Glu Met Glu Val Gln Glu Pro Ala Glu Pro Thr Gly Val Asn
            260                 265                 270

Met Leu Ser Pro Gly Glu Ser Glu His Leu Leu Glu Pro Ala Glu Ala
            275                 280                 285

Glu Arg Ser Gln Arg Arg Arg Leu Leu Val Pro Ala Asn Glu Gly Asp
            290                 295                 300

Pro Thr Glu Thr Leu Arg Gln Cys Phe Asp Asp Phe Ala Asp Leu Val
305                 310                 315                 320

Pro Phe Asp Ser Trp Glu Pro Leu Met Arg Lys Leu Gly Leu Met Asp
            325                 330                 335

Asn Glu Ile Lys Val Ala Lys Ala Glu Ala Ala Gly His Arg Asp Thr
            340                 345                 350

Leu Tyr Thr Met Leu Ile Lys Trp Val Asn Lys Thr Gly Arg Asp Ala
            355                 360                 365

Ser Val His Thr Leu Leu Asp Ala Leu Glu Thr Leu Gly Glu Arg Leu
            370                 375                 380

Ala Lys Gln Lys Ile Glu Asp His Leu Leu Ser Ser Gly Lys Phe Met
385                 390                 395                 400

Tyr Leu Glu Gly Asn Ala Asp Ser Ala Met Ser
            405                 410

<210> SEQ ID NO 53
<211> LENGTH: 22
<212> TYPE: DNA
<213> ORGANISM: Homo sapiens

<400> SEQUENCE: 53
ttagaaggyg ggaataattt tg                                          22

<210> SEQ ID NO 54
<211> LENGTH: 22
<212> TYPE: DNA
<213> ORGANISM: Homo sapiens

<400> SEQUENCE: 54
tcaatctcaa acccraactc tc                                          22

<210> SEQ ID NO 55
<211> LENGTH: 15
<212> TYPE: DNA
<213> ORGANISM: Homo sapiens

<400> SEQUENCE: 55
ggtgacgggc ggggt                                                  15

```
<210> SEQ ID NO 56
<211> LENGTH: 20
<212> TYPE: DNA
<213> ORGANISM: Homo sapiens

<400> SEQUENCE: 56
aaacccgaac tctcgatccg                                              20

<210> SEQ ID NO 57
<211> LENGTH: 20
<212> TYPE: DNA
<213> ORGANISM: Homo sapiens

<400> SEQUENCE: 57
ttttggtgat gggtggggtt                                              20

<210> SEQ ID NO 58
<211> LENGTH: 23
<212> TYPE: DNA
<213> ORGANISM: Homo sapiens

<400> SEQUENCE: 58
ctcaaaccca aactctcaat cca                                          23

<210> SEQ ID NO 59
<211> LENGTH: 24
<212> TYPE: DNA
<213> ORGANISM: Homo sapiens

<400> SEQUENCE: 59
gtatttggyg ttttaggttt ttag                                         24

<210> SEQ ID NO 60
<211> LENGTH: 20
<212> TYPE: DNA
<213> ORGANISM: Homo sapiens

<400> SEQUENCE: 60
cccctccaac rataaatacc                                              20

<210> SEQ ID NO 61
<211> LENGTH: 25
<212> TYPE: DNA
<213> ORGANISM: Homo sapiens

<400> SEQUENCE: 61
ttttagtttc gacgtttttt gtagc                                        25

<210> SEQ ID NO 62
<211> LENGTH: 22
<212> TYPE: DNA
<213> ORGANISM: Homo sapiens

<400> SEQUENCE: 62
caacgataaa taccgactcc cg                                           22

<210> SEQ ID NO 63
<211> LENGTH: 28
<212> TYPE: DNA
<213> ORGANISM: Homo sapiens

<400> SEQUENCE: 63 ggttttagt tttgatgttt ttgtagt                                       28
```

<210> SEQ ID NO 64
<211> LENGTH: 24
<212> TYPE: DNA
<213> ORGANISM: Homo sapiens

<400> SEQUENCE: 64
tccaacaata ataccaact ccca                                    24

<210> SEQ ID NO 65
<211> LENGTH: 21
<212> TYPE: DNA
<213> ORGANISM: Homo sapiens

<400> SEQUENCE: 65
ggtgggtaga ggttgagttt t                                      21

<210> SEQ ID NO 66
<211> LENGTH: 26
<212> TYPE: DNA
<213> ORGANISM: Homo sapiens

<400> SEQUENCE: 66
ccattacaat catatatcaa tcaaac                                 26

<210> SEQ ID NO 67
<211> LENGTH: 23
<212> TYPE: DNA
<213> ORGANISM: Homo sapiens

<400> SEQUENCE: 67
aggttgagtt ttcgataacg agc                                    23

<210> SEQ ID NO 68
<211> LENGTH: 27
<212> TYPE: DNA
<213> ORGANISM: Homo sapiens

<400> SEQUENCE: 68
catatatcaa tcaaacgcgt acgaccg                                27

<210> SEQ ID NO 69
<211> LENGTH: 28
<212> TYPE: DNA
<213> ORGANISM: Homo sapiens

<400> SEQUENCE: 69
ggtagaggtt gagtttttga taatgagt                               28

<210> SEQ ID NO 70
<211> LENGTH: 28
<212> TYPE: DNA
<213> ORGANISM: Homo sapiens

<400> SEQUENCE: 70
aatcatatat caatcaaaca tacaacca                               28

<210> SEQ ID NO 71
<211> LENGTH: 20
<212> TYPE: DNA
<213> ORGANISM: Homo sapiens

<400> SEQUENCE: 71

```
tagtggggat gggaggtgtt                                          20

<210> SEQ ID NO 72
<211> LENGTH: 19
<212> TYPE: DNA
<213> ORGANISM: Homo sapiens

<400> SEQUENCE: 72
ccccaaaacc caaataaaa                                           19

<210> SEQ ID NO 73
<211> LENGTH: 21
<212> TYPE: DNA
<213> ORGANISM: Homo sapiens

<400> SEQUENCE: 73
atgggaggtg ttcgagacgt c                                        21

<210> SEQ ID NO 74
<211> LENGTH: 20
<212> TYPE: DNA
<213> ORGANISM: Homo sapiens

<400> SEQUENCE: 74
aacgcatcca aaacgaaacg                                          20

<210> SEQ ID NO 75
<211> LENGTH: 23
<212> TYPE: DNA
<213> ORGANISM: Homo sapiens

<400> SEQUENCE: 75
ggatgggagg tgtttgagat gtt                                      23

<210> SEQ ID NO 76
<211> LENGTH: 26
<212> TYPE: DNA
<213> ORGANISM: Homo sapiens

<400> SEQUENCE: 76
ctacaaaaca catccaaaac aaaaca                                   26

<210> SEQ ID NO 77
<211> LENGTH: 19
<212> TYPE: DNA
<213> ORGANISM: Homo sapiens

<400> SEQUENCE: 77
gggtttggat ttggggatt                                           19

<210> SEQ ID NO 78
<211> LENGTH: 22
<212> TYPE: DNA
<213> ORGANISM: Homo sapiens

<400> SEQUENCE: 78
caaatcaatc raatccaaaa aa                                       22

<210> SEQ ID NO 79
<211> LENGTH: 19
<212> TYPE: DNA
<213> ORGANISM: Homo sapiens

<400> SEQUENCE: 79
```

```
gggggaggttt cggagcgtc                                              19

<210> SEQ ID NO 80
<211> LENGTH: 19
<212> TYPE: DNA
<213> ORGANISM: Homo sapiens

<400> SEQUENCE: 80
caaaaaatcg aaccccgcg                                               19

<210> SEQ ID NO 81
<211> LENGTH: 22
<212> TYPE: DNA
<213> ORGANISM: Homo sapiens

<400> SEQUENCE: 81 gaggggagg ttttggagtg tt                                            22

<210> SEQ ID NO 82
<211> LENGTH: 23
<212> TYPE: DNA
<213> ORGANISM: Homo sapiens

<400> SEQUENCE: 82
aatccaaaaa atcaaacccc aca                                          23

<210> SEQ ID NO 83
<211> LENGTH: 20
<212> TYPE: DNA
<213> ORGANISM: Homo sapiens

<400> SEQUENCE: 83
gaggtggggt gttgggttat                                              20

<210> SEQ ID NO 84
<211> LENGTH: 19
<212> TYPE: DNA
<213> ORGANISM: Homo sapiens

<400> SEQUENCE: 84
cccccaaaaa aacctaccc                                               19

<210> SEQ ID NO 85
<211> LENGTH: 18
<212> TYPE: DNA
<213> ORGANISM: Homo sapiens

<400> SEQUENCE: 85
taggcgtttg gcggaagc                                                18

<210> SEQ ID NO 86
<211> LENGTH: 18
<212> TYPE: DNA
<213> ORGANISM: Homo sapiens

<400> SEQUENCE: 86
acctacccgc caacgacg                                                18

<210> SEQ ID NO 87
<211> LENGTH: 24
<212> TYPE: DNA
<213> ORGANISM: Homo sapiens
```

```
<400> SEQUENCE: 87
gggttatagg tgtttggtgg aagt                                          24

<210> SEQ ID NO 88
<211> LENGTH: 23
<212> TYPE: DNA
<213> ORGANISM: Homo sapiens

<400> SEQUENCE: 88
aaaaaaccta cccaccaaca aca                                           23

<210> SEQ ID NO 89
<211> LENGTH: 24
<212> TYPE: DNA
<213> ORGANISM: Homo sapiens

<400> SEQUENCE: 89
gagtygtttg ggttgtagtt ttat                                          24

<210> SEQ ID NO 90
<211> LENGTH: 28
<212> TYPE: DNA
<213> ORGANISM: Homo sapiens

<400> SEQUENCE: 90
atctaaatct cctataaact tctacctc                                      28

<210> SEQ ID NO 91
<211> LENGTH: 19
<212> TYPE: DNA
<213> ORGANISM: Homo sapiens

<400> SEQUENCE: 91
tcgggagtcg gtagggagc                                                19

<210> SEQ ID NO 92
<211> LENGTH: 25
<212> TYPE: DNA
<213> ORGANISM: Homo sapiens

<400> SEQUENCE: 92
ctcgcgacta ctcctaaaat atacg                                         25

<210> SEQ ID NO 93
<211> LENGTH: 24
<212> TYPE: DNA
<213> ORGANISM: Homo sapiens

<400> SEQUENCE: 93
tttatttggg agttggtagg gagt                                          24

<210> SEQ ID NO 94
<211> LENGTH: 30
<212> TYPE: DNA
<213> ORGANISM: Homo sapiens

<400> SEQUENCE: 94
tctacctcac aactactcct aaaatataca                                    30

<210> SEQ ID NO 95
<211> LENGTH: 20
<212> TYPE: DNA
<213> ORGANISM: Homo sapiens
```

-continued

<400> SEQUENCE: 95
gaagtygttt ttggggattg                                               20

<210> SEQ ID NO 96
<211> LENGTH: 19
<212> TYPE: DNA
<213> ORGANISM: Homo sapiens

<400> SEQUENCE: 96
atcctcctac tcccrcaaa                                                19

<210> SEQ ID NO 97
<211> LENGTH: 20
<212> TYPE: DNA
<213> ORGANISM: Homo sapiens

<400> SEQUENCE: 97
ggattgagcg ttgcggtttc                                               20

<210> SEQ ID NO 98
<211> LENGTH: 19
<212> TYPE: DNA
<213> ORGANISM: Homo sapiens

<400> SEQUENCE: 98
ccgcaaacaa aaccgaacg                                                19

<210> SEQ ID NO 99
<211> LENGTH: 22
<212> TYPE: DNA
<213> ORGANISM: Homo sapiens

<400> SEQUENCE: 99
ggggattgag tgttgtggtt tt                                            22

<210> SEQ ID NO 100
<211> LENGTH: 22
<212> TYPE: DNA
<213> ORGANISM: Homo sapiens

<400> SEQUENCE: 100
ctcccacaaa caaaaccaaa ca                                            22

<210> SEQ ID NO 101
<211> LENGTH: 25
<212> TYPE: DNA
<213> ORGANISM: Homo sapiens

<400> SEQUENCE: 101
gaygttttta gggttatttt ttata                                         25

<210> SEQ ID NO 102
<211> LENGTH: 24
<212> TYPE: DNA
<213> ORGANISM: Homo sapiens

<400> SEQUENCE: 102
tccacaaata tttactaaac accc                                          24

<210> SEQ ID NO 103
<211> LENGTH: 26
<212> TYPE: DNA

```
<213> ORGANISM: Homo sapiens

<400> SEQUENCE: 103 gttattttt  atacggtaag  tacggc                                    26

<210> SEQ ID NO 104
<211> LENGTH: 20
<212> TYPE: DNA
<213> ORGANISM: Homo sapiens

<400> SEQUENCE: 104
acccgcgatt  cttaacaacg                                           20

<210> SEQ ID NO 105
<211> LENGTH: 29
<212> TYPE: DNA
<213> ORGANISM: Homo sapiens

<400> SEQUENCE: 105
agggttattt  tttatatggt  aagtatggt                                29

<210> SEQ ID NO 106
<211> LENGTH: 26
<212> TYPE: DNA
<213> ORGANISM: Homo sapiens

<400> SEQUENCE: 106
ctaaacaccc  acaattctta  acaaca                                   26

<210> SEQ ID NO 107
<211> LENGTH: 19
<212> TYPE: DNA
<213> ORGANISM: Homo sapiens

<400> SEQUENCE: 107
ggygggagga  agtgttaga                                            19

<210> SEQ ID NO 108
<211> LENGTH: 21
<212> TYPE: DNA
<213> ORGANISM: Homo sapiens

<400> SEQUENCE: 108
ccccaaaaac  aacaacatca  a                                        21

<210> SEQ ID NO 109
<211> LENGTH: 24
<212> TYPE: DNA
<213> ORGANISM: Homo sapiens

<400> SEQUENCE: 109
ttagagtttt  cgattttcg  ttgc                                      24

<210> SEQ ID NO 110
<211> LENGTH: 22
<212> TYPE: DNA
<213> ORGANISM: Homo sapiens

<400> SEQUENCE: 110
aacaacaaca  tcaacgacga  cg                                       22

<210> SEQ ID NO 111
<211> LENGTH: 29
```

```
<212> TYPE: DNA
<213> ORGANISM: Homo sapiens

<400> SEQUENCE: 111
aagtgttaga gttttgatt ttttgttgt                              29

<210> SEQ ID NO 112
<211> LENGTH: 26
<212> TYPE: DNA
<213> ORGANISM: Homo sapiens

<400> SEQUENCE: 112
caaaaacaac aacatcaaca acaaca                                26

<210> SEQ ID NO 113
<211> LENGTH: 20
<212> TYPE: DNA
<213> ORGANISM: Homo sapiens

<400> SEQUENCE: 113
gtttttggga agggagaag                                        20

<210> SEQ ID NO 114
<211> LENGTH: 28
<212> TYPE: DNA
<213> ORGANISM: Homo sapiens

<400> SEQUENCE: 114
aattaaaaaa aacacttaaa aaattaac                              28

<210> SEQ ID NO 115
<211> LENGTH: 22
<212> TYPE: DNA
<213> ORGANISM: Homo sapiens

<400> SEQUENCE: 115
gattaagacg cgtttggaaa gc                                    22

<210> SEQ ID NO 116
<211> LENGTH: 20
<212> TYPE: DNA
<213> ORGANISM: Homo sapiens

<400> SEQUENCE: 116
attaacgcct cccgaaatcg                                       20

<210> SEQ ID NO 117
<211> LENGTH: 28
<212> TYPE: DNA
<213> ORGANISM: Homo sapiens

<400> SEQUENCE: 117
ggagaagatt aagatgtgtt tggaaagt                              28

<210> SEQ ID NO 118
<211> LENGTH: 26
<212> TYPE: DNA
<213> ORGANISM: Homo sapiens

<400> SEQUENCE: 118
taaaaaatta acacctccca aaatca                                26

<210> SEQ ID NO 119
```

```
<211> LENGTH: 25
<212> TYPE: DNA
<213> ORGANISM: Homo sapiens

<400> SEQUENCE: 119
ttaaattgga aagattagga aagtt                                              25

<210> SEQ ID NO 120
<211> LENGTH: 18
<212> TYPE: DNA
<213> ORGANISM: Homo sapiens

<400> SEQUENCE: 120
tcaaactaaa cccrcccc                                                      18

<210> SEQ ID NO 121
<211> LENGTH: 23
<212> TYPE: DNA
<213> ORGANISM: Homo sapiens

<400> SEQUENCE: 121
attaggaaag ttcgtttacg ggc                                                23

<210> SEQ ID NO 122
<211> LENGTH: 20
<212> TYPE: DNA
<213> ORGANISM: Homo sapiens

<400> SEQUENCE: 122
cgaaaaaacc tacgaccgcg                                                    20

<210> SEQ ID NO 123
<211> LENGTH: 28
<212> TYPE: DNA
<213> ORGANISM: Homo sapiens

<400> SEQUENCE: 123
gaaagattag gaaagtttgt ttatgggt                                           28

<210> SEQ ID NO 124
<211> LENGTH: 22
<212> TYPE: DNA
<213> ORGANISM: Homo sapiens

<400> SEQUENCE: 124
cccgaaaaaa cctacaacca ca                                                 22

<210> SEQ ID NO 125
<211> LENGTH: 19
<212> TYPE: DNA
<213> ORGANISM: Homo sapiens

<400> SEQUENCE: 125
ttggggtgay gtagttggg                                                     19

<210> SEQ ID NO 126
<211> LENGTH: 19
<212> TYPE: DNA
<213> ORGANISM: Homo sapiens

<400> SEQUENCE: 126
ccaaatcctt cctcraccc                                                     19
```

```
<210> SEQ ID NO 127
<211> LENGTH: 22
<212> TYPE: DNA
<213> ORGANISM: Homo sapiens

<400> SEQUENCE: 127
cgtagttggg cgcgattagt ac                                          22

<210> SEQ ID NO 128
<211> LENGTH: 18
<212> TYPE: DNA
<213> ORGANISM: Homo sapiens

<400> SEQUENCE: 128
tctccgccga cgctaacg                                               18

<210> SEQ ID NO 129
<211> LENGTH: 27
<212> TYPE: DNA
<213> ORGANISM: Homo sapiens

<400> SEQUENCE: 129
ggtgatgtag ttgggtgtga ttagtat                                     27

<210> SEQ ID NO 130
<211> LENGTH: 27
<212> TYPE: DNA
<213> ORGANISM: Homo sapiens

<400> SEQUENCE: 130
atttaaaatt ctccaccaac actaaca                                     27

<210> SEQ ID NO 131
<211> LENGTH: 23
<212> TYPE: DNA
<213> ORGANISM: Homo sapiens

<400> SEQUENCE: 131
ggttttygtt atgtgggata ttt                                         23

<210> SEQ ID NO 132
<211> LENGTH: 19
<212> TYPE: DNA
<213> ORGANISM: Homo sapiens

<400> SEQUENCE: 132
acccaaaccc tccaaaacc                                              19

<210> SEQ ID NO 133
<211> LENGTH: 22
<212> TYPE: DNA
<213> ORGANISM: Homo sapiens

<400> SEQUENCE: 133
ttgggtcgtt tcggattgat ac                                          22

<210> SEQ ID NO 134
<211> LENGTH: 23
<212> TYPE: DNA
<213> ORGANISM: Homo sapiens

<400> SEQUENCE: 134
ccgactacaa aacaaaaacg acg                                         23
```

```
<210> SEQ ID NO 135
<211> LENGTH: 24
<212> TYPE: DNA
<213> ORGANISM: Homo sapiens

<400> SEQUENCE: 135
ttttgggttg ttttggattg atat                                          24

<210> SEQ ID NO 136
<211> LENGTH: 26
<212> TYPE: DNA
<213> ORGANISM: Homo sapiens

<400> SEQUENCE: 136
aaaccaacta caaaacaaaa acaaca                                        26

<210> SEQ ID NO 137
<211> LENGTH: 24
<212> TYPE: DNA
<213> ORGANISM: Homo sapiens

<400> SEQUENCE: 137
tttaggtaat atgtyggaag gaaa                                          24

<210> SEQ ID NO 138
<211> LENGTH: 24
<212> TYPE: DNA
<213> ORGANISM: Homo sapiens

<400> SEQUENCE: 138
ccctaaaacr aataaaaaaa aaac                                          24

<210> SEQ ID NO 139
<211> LENGTH: 22
<212> TYPE: DNA
<213> ORGANISM: Homo sapiens

<400> SEQUENCE: 139
tttagtacgt cgggagggtt tc                                            22

<210> SEQ ID NO 140
<211> LENGTH: 23
<212> TYPE: DNA
<213> ORGANISM: Homo sapiens

<400> SEQUENCE: 140
aacgaataaa aaaaaaacga ccg                                           23

<210> SEQ ID NO 141
<211> LENGTH: 25
<212> TYPE: DNA
<213> ORGANISM: Homo sapiens

<400> SEQUENCE: 141
gagtttagta tgttgggagg gtttt                                         25

<210> SEQ ID NO 142
<211> LENGTH: 27
<212> TYPE: DNA
<213> ORGANISM: Homo sapiens

<400> SEQUENCE: 142
ctaaaacaaa taaaaaaaaa acaacca                                       27
```

```
<210> SEQ ID NO 143
<211> LENGTH: 24
<212> TYPE: DNA
<213> ORGANISM: Homo sapiens

<400> SEQUENCE: 143
ttttaggttt ttttagtttt tggg                                              24

<210> SEQ ID NO 144
<211> LENGTH: 20
<212> TYPE: DNA
<213> ORGANISM: Homo sapiens

<400> SEQUENCE: 144
cataaaacca atcaacrccc                                                   20

<210> SEQ ID NO 145
<211> LENGTH: 23
<212> TYPE: DNA
<213> ORGANISM: Homo sapiens

<400> SEQUENCE: 145
tttagttttt gggcgtacgt ttc                                               23

<210> SEQ ID NO 146
<211> LENGTH: 17
<212> TYPE: DNA
<213> ORGANISM: Homo sapiens

<400> SEQUENCE: 146
caatcaacgc ccgaccg                                                      17

<210> SEQ ID NO 147
<211> LENGTH: 27
<212> TYPE: DNA
<213> ORGANISM: Homo sapiens

<400> SEQUENCE: 147
tttttttagt ttttgggtgt atgtttt                                           27

<210> SEQ ID NO 148
<211> LENGTH: 22
<212> TYPE: DNA
<213> ORGANISM: Homo sapiens

<400> SEQUENCE: 148
aaaaccaatc aacacccaac ca                                                22

<210> SEQ ID NO 149
<211> LENGTH: 22
<212> TYPE: DNA
<213> ORGANISM: Homo sapiens

<400> SEQUENCE: 149
ttatygtttt ttggttttgg tt                                                22

<210> SEQ ID NO 150
<211> LENGTH: 20
<212> TYPE: DNA
<213> ORGANISM: Homo sapiens

<400> SEQUENCE: 150
```

```
acaaaaccac ttcctaccrc                                              20

<210> SEQ ID NO 151
<211> LENGTH: 20
<212> TYPE: DNA
<213> ORGANISM: Homo sapiens

<400> SEQUENCE: 151
ggttttggtt ggtcgttcgc                                              20

<210> SEQ ID NO 152
<211> LENGTH: 18
<212> TYPE: DNA
<213> ORGANISM: Homo sapiens

<400> SEQUENCE: 152
cttcctaccg cgaccccg                                                18

<210> SEQ ID NO 153
<211> LENGTH: 23
<212> TYPE: DNA
<213> ORGANISM: Homo sapiens

<400> SEQUENCE: 153
tttggttttg gttggttgtt tgt                                          23

<210> SEQ ID NO 154
<211> LENGTH: 21
<212> TYPE: DNA
<213> ORGANISM: Homo sapiens

<400> SEQUENCE: 154
ccacttccta ccacaacccc a                                            21

<210> SEQ ID NO 155
<211> LENGTH: 25
<212> TYPE: DNA
<213> ORGANISM: Homo sapiens

<400> SEQUENCE: 155
gtttagtttt taggtttygt ttttt                                        25

<210> SEQ ID NO 156
<211> LENGTH: 24
<212> TYPE: DNA
<213> ORGANISM: Homo sapiens

<400> SEQUENCE: 156
aaacaaaaca aaacractaa aacc                                         24

<210> SEQ ID NO 157
<211> LENGTH: 22
<212> TYPE: DNA
<213> ORGANISM: Homo sapiens

<400> SEQUENCE: 157
ggtttcgttt tttcggttaa gc                                           22

<210> SEQ ID NO 158
<211> LENGTH: 21
<212> TYPE: DNA
<213> ORGANISM: Homo sapiens

<400> SEQUENCE: 158
```

```
acgactaaaa ccgaaatccc g                                          21

<210> SEQ ID NO 159
<211> LENGTH: 27
<212> TYPE: DNA
<213> ORGANISM: Homo sapiens

<400> SEQUENCE: 159 tttttaggttt tgttttttg gttaagt                                    27

<210> SEQ ID NO 160
<211> LENGTH: 24
<212> TYPE: DNA
<213> ORGANISM: Homo sapiens

<400> SEQUENCE: 160
aaaacaacta aaccaaaat ccca                                        24

<210> SEQ ID NO 161
<211> LENGTH: 26
<212> TYPE: DNA
<213> ORGANISM: Homo sapiens

<400> SEQUENCE: 161
gtttttagtt atygtttttt ggaaat                                     26

<210> SEQ ID NO 162
<211> LENGTH: 21
<212> TYPE: DNA
<213> ORGANISM: Homo sapiens

<400> SEQUENCE: 162
ccccaaatcc tcctaaattc c                                          21

<210> SEQ ID NO 163
<211> LENGTH: 23
<212> TYPE: DNA
<213> ORGANISM: Homo sapiens

<400> SEQUENCE: 163
ttggaaatat tattcgtcgg ggc                                        23

<210> SEQ ID NO 164
<211> LENGTH: 19
<212> TYPE: DNA
<213> ORGANISM: Homo sapiens

<400> SEQUENCE: 164
ccgcttccac cgaaaaccg                                             19

<210> SEQ ID NO 165
<211> LENGTH: 28
<212> TYPE: DNA
<213> ORGANISM: Homo sapiens

<400> SEQUENCE: 165 gtttttgga aatattattt gttggggt                                    28

<210> SEQ ID NO 166
<211> LENGTH: 27
<212> TYPE: DNA
<213> ORGANISM: Homo sapiens
```

-continued

```
<400> SEQUENCE: 166
ctaaattccc tcttccacct aaaacct                                          27

<210> SEQ ID NO 167
<211> LENGTH: 22
<212> TYPE: DNA
<213> ORGANISM: Homo sapiens

<400> SEQUENCE: 167
ggttgggttt tttttaatt tt                                                22

<210> SEQ ID NO 168
<211> LENGTH: 21
<212> TYPE: DNA
<213> ORGANISM: Homo sapiens

<400> SEQUENCE: 168
ttttccctaa aaatccraaa a                                                21

<210> SEQ ID NO 169
<211> LENGTH: 20
<212> TYPE: DNA
<213> ORGANISM: Homo sapiens

<400> SEQUENCE: 169
gcgtttgttg ttgggtcgtc                                                  20

<210> SEQ ID NO 170
<211> LENGTH: 19
<212> TYPE: DNA
<213> ORGANISM: Homo sapiens

<400> SEQUENCE: 170
cccgaataaa cgactcccg                                                   19

<210> SEQ ID NO 171
<211> LENGTH: 23
<212> TYPE: DNA
<213> ORGANISM: Homo sapiens

<400> SEQUENCE: 171
tttgtgtttg ttgttgggtt gtt                                              23

<210> SEQ ID NO 172
<211> LENGTH: 21
<212> TYPE: DNA
<213> ORGANISM: Homo sapiens

<400> SEQUENCE: 172
cccccaaata aacaactccc a                                                21
```

METHYLATION MARKERS FOR DIAGNOSIS AND TREATMENT OF OVARIAN CANCER

This application claims the benefit of provisional application 60/724,265 filed Oct. 7, 2005. The entire disclosure of the provisional application is incorporated herein by reference.

This application incorporates by reference the contents of each of two duplicate CD-ROMs. Each CD-ROM contains an identical 186 kB file labeled "000040NC0 sequence listing" and containing the sequence listing for this application. Each CD-ROM also contains an identical 4.8 MB file labeled "ovarian.combinations" containing TABLE 1. The CD-ROMs were created on Oct. 06, 3006.

TECHNICAL FIELD OF THE INVENTION

This invention is related to the area of cancer diagnostics and therapeutics. In particular, it relates to aberrant methylation patterns of particular genes in cancers.

BACKGROUND OF THE INVENTION

DNA Methylation and its Role in Carcinogenesis

The information to make the cells of all living organisms is contained in their DNA. DNA is made up of a unique sequence of four bases: adenine (A), guanine (G), thymine (T) and cytosine (C). These bases are paired A to T and G to C on the two strands that form the DNA double helix. Strands of these pairs store information to make specific molecules grouped into regions called genes. Within each cell, there are processes that control what gene is turned on, or expressed, thus defining the unique function of the cell. One of these control mechanisms is provided by adding a methyl group onto cytosine (C). The methyl group tagged C can be written as mC.

DNA methylation plays an important role in determining whether some genes are expressed or not. By turning genes off that are not needed, DNA methylation functions as an essential control mechanism for the normal development and functioning of organisms. Conversely, abnormal DNA methylation is one of the mechanisms underlying the changes observed with aging and development of many cancers.

Historically, cancers have been linked to genetic changes caused by chromosomal mutations within the DNA. Mutations, hereditary or acquired, can lead to the loss of expression of genes critical for maintaining a healthy state. Evidence now indicates that a relatively large number of cancers originate, not from mutations, but from inappropriate DNA methylation. In many cases, hyper-methylation of DNA incorrectly switches off critical genes, such as tumor suppressor genes or DNA repair genes, allowing cancers to develop and progress. This non-mutational process for controlling gene expression is described as epigenetics.

DNA methylation is a chemical modification of DNA performed by enzymes called methyltransferases, in which a methyl group (m) is added to certain cytosines (C) of DNA. This non-mutational (epigenetic) process (mC) is a critical factor in gene expression regulation. See, J. G. Herman, Seminars in Cancer Biology, 9: 359-67, 1999.

Although the phenomenon of gene methylation has attracted the attention of cancer researchers for some time, its true role in the progression of human cancers is just now being recognized. In normal cells, methylation occurs predominantly in regions of DNA that have few CG base repeats, while CpG islands, regions of DNA that have long repeats of CG bases, remain non-methylated. Gene promoter regions that control protein expression are often CpG island-rich. Aberrant methylation of these normally non-methylated CpG islands in the promoter region causes transcriptional inactivation or silencing of certain tumor suppressor expression in human cancers.

Genes that are hypermethylated in tumor cells are strongly specific to the tissue of origin of the tumor. Molecular signatures of cancers of all types can be used to improve cancer detection, the assessment of cancer risk and response to therapy. Hypermethylated promoters events provide some of the most promising markers for such purposes.

Promoter Gene Hypermethylation: Promising Tumor Markers

Information regarding the hypermethylation of specific promoters of genes can be beneficial to diagnosis, prognosis and treatment of various cancers. Methylation of specific promoter regions can occur early and often in carcinogenesis making these markers ideal targets for cancer diagnostics.

Methylation patterns are tumor specific. Positive signals are always found in the same location of a gene. Real time PCR-based methods are highly sensitive, quantitative, and suitable for clinical use. DNA is stable and is found intact in readily available fluids (e.g., serum, sputum, stool and urine) and paraffin embedded tissues. Panels of pertinent gene markers may cover most human cancers.

Diagnosis

Key to improving the clinical outcome in patients with cancer is diagnosis at its earliest stage, while the cancer is still localized and readily treatable. The characteristics noted above provide the means for a more accurate screening and surveillance program by identifying higher-risk patients on a molecular basis. They could also provide justification for more definitive follow-up of patients who have molecular features, but not yet all the pathological or clinical features associated with malignancy.

Predicting Treatment Response

Information about how a cancer develops through molecular events could allow a clinician to predict more accurately how such a cancer is likely to respond to specific chemotherapeutic agents. In this way, a regimen based on knowledge of the tumor's chemosensitivity could be rationally designed. Studies have shown that hypermethylation of the MGMT promoter in glioma patients is indicative of a good response to therapy, greater overall survival, and a longer time to progression.

There is a continuing need in the art for new diagnostic markers and therapeutic targets for cancer to improve management of patient care.

SUMMARY OF THE INVENTION

According to a first embodiment of the invention a method is provided for identifying an ovarian cell as neoplastic or predisposed to neoplasia. Epigenetic silencing of at least one gene listed in Table 2 is detected in a test cell. The test cell is identified as neoplastic or predisposed to neoplasia based on the detection of epigenetic silencing.

In another embodiment of the invention a method is provided for reducing or inhibiting neoplastic growth of an ovarian cell which exhibits epigenetic silenced transcription of at least one gene associated with a cancer. Expression of a polypeptide encoded by the epigenetic silenced gene is restored in the cell by contacting the cell with a CpG dinucleotide demethylating agent. The gene is selected from those listed in Table 2. Unregulated growth of the cell is thereby reduced or inhibited.

Another aspect of the invention is a method of reducing or inhibiting neoplastic growth of an ovarian cell which exhibits epigenetic silenced transcription of at least one gene associated with a cancer. A polynucleotide encoding a polypeptide is introduced into an ovarian cell which exhibits epigenetic silenced transcription of at least one gene listed in Table 2. The polypeptide is encoded by the epigenetic-silenced gene. The polypeptide is thereby expressed in the cell thereby restoring expression of the polypeptide in the cell.

Still another aspect of the invention is a method of treating an ovarian cancer patient. A demethylating agent is administered to the patient in sufficient amounts to restore expression of a tumor-associated methylation-silenced gene selected from those listed in Table 2 in the patient's tumor.

An additional embodiment of the invention provides a method of treating an ovarian cancer patient. A polynucleotide encoding a polypeptide is administered to the patient. The polypeptide is encoded by a gene listed in Table 2. The polypeptide is expressed in the patient's tumor thereby restoring expression of the polypeptide in the tumor.

Yet another embodiment of the invention is a method for selecting a therapeutic strategy for treating an ovarian cancer patient. A gene selected from those listed in Table 2 whose expression in cancer cells of the patient is reactivated by a demethylating agent is identified. A therapeutic agent which reactivates expression of the gene is selected for treating the cancer patient.

A further embodiment of the invention is a kit for assessing methylation in an ovarian cell sample. The kit comprises certain components in a package. One component is a reagent that (a) modifies methylated cytosine residues but not non-methylated cytosine residues, or that (b) modifies non-methylated cytosine residues but not methylated cytosine residues. A second component is a pair of oligonucleotide primers that specifically hybridizes under amplification conditions to a region of a gene selected from those listed in Table 2. The region is within about 1 kb of said gene's transcription start site.

These and other embodiments which will be apparent to those of skill in the art upon reading the specification provide the art with tools and methods for detection, diagnosis, therapy, and drug selection pertaining to neoplastic cells and cancers.

BRIEF DESCRIPTION OF THE TABLES

Table 1 lists combinations of 2, 3, 4, 5, and 6 genes which are hypermethylated in ovarian cancer cells.

Table 2 lists genes and splice variants which are hypermethylated in ovarian cancer cells. Accession numbers for the encoded proteins and nucleic acids are shown.

Table 3 accompanies the Sequence Listing.

Table 4 shows primers and annealing temperatures used for MSP reactions

Table 5 shows promoter hypermethylation results of tubae standard genes.

Table 6 shows MSP methascore results and the SCA grading for each of the subjects.

DETAILED DESCRIPTION OF THE INVENTION

The inventors have discovered a set of genes whose transcription is epigenetically silenced in ovarian cancers. These genes include those encoding TTKTTK protein kinase, CGI-38 brain specific protein, DUSP4 dual specificity phosphatase 4, RUNX3 runt-related transcription factor 3, TRIP13 thyroid hormone receptor interactor 13, TK1 thymidine kinase 1 (soluble), SMPD2 sphingomyelin phosphodiesterase 2 (neutral membrane; neutral sphingomyelinase), MYBL2 v-myb myeloblastosis viral oncogene homolog (avian)-like 2, MSH2 mutS homolog 2, nonpolyposis type 1 colon cancer, BARD1 BRCA1 associated RING domain 1, INPP4B inositol polyphosphate-4-phosphatase, type II (105 kDa), NDP Norrie disease (pseudoglioma), TM4SF11 transmembrane 4 superfamily member 11 (plasmolipin), HPSE heparanase, C11orf2 chromosome 11 open reading frame 2, DEKDEK oncogene (DNA binding), ASK activator of S phase kinase, POLR3D polymerase (RNA) III (DNA directed) polypeptide D (44 kDa), HEC highly expressed in cancer, rich in leucine heptad repeats, ACTN1 actinin (alpha 1), FANCG Fanconi anemia (complementation group G), HDGF hepatoma-derived growth factor (high-mobility group protein 1-like), and TNFRSF10B tumor necrosis factor receptor superfamily (member 10b). All of the identified genes are shown in Table 2.

TABLE 2

| | | |
|---|---|---|
| 1. TTK | NP_003309 | NM_003318 |
| 2. CGI-38 | NP_057048, | NM_015964.2, |
| | NP_057224 | NM_016140.2 |
| 3. DUSP4 | NP_476499, | NM_057158.2, |
| | NP_001385 | NM_001394.5 |
| 4. RUNX3 | NP_004341 | NM_004350.1 |
| 5. TRIP13 | NP_004228 | NM_004237.2 |
| 6. TK1 | NP_003249 | NM_003258.1 |
| 7. SMPD2 | NP_003071 | NM_003080.1 |
| 8. MYBL2 | NP_002457 | NM_002466.2 |
| 9. MSH2 | NP_000242 | NM_000251.1 |
| 10. BARD1 | NP_000456 | NM_000465.1 |
| 11. INPP4B | NP_003857 | NM_003866.1 |
| 12. NDP | NP_000257 | NM_000266.1 |
| 13. TM4SF11 | NP_057077 | NM_015993.1 |
| 14. HPSE | NP_006656 | NM_006665.2 |
| 15. C11orf2 | NP_037397 | NM_013265.2 |
| 16. DEK | NP_003463 | NM_003472.2 |
| 17. ASK | NP_006707 | NM_006716.3 |
| 18. POLR3D | NP_001713, | NM_001722.2 |
| 19. HEC | NP_006092 | NM_006101.1 |
| 20. ACTN1 | NP_001093 | NM_001102.2 |
| 21. FANCG | NP_004620 | NM_004629.1 |
| 22. HDGF | NP_004485 | NM_004494.1 |
| 23. TNFRSF10B | NP_003833, | NM_003842.3, |
| | NP_671716 | NM_147187.1 |

Epigenetic silencing of a gene can be determined by any method known in the art. One method is to determine that a gene which is expressed in normal cells is less expressed or not expressed in tumor cells. This method does not, on its own, however, indicate that the silencing is epigenetic, as the mechanism of the silencing could be genetic, for example, by somatic mutation. One method to determine that the silencing is epigenetic is to treat with a reagent, such as DAC (5'-deazacytidine) and observe that the silencing is reversed, i.e., that the expression of the gene is reactivated or restored. Another means to determine epigenetic silencing is to determine the presence of methylated CpG dinucleotide motifs in the silenced gene. Typically these reside near the transcription start site, for example, within about 1 kbp, within about 750 bp, or within about 500 bp.

Expression of a gene can be assessed using any means known in the art. Either mRNA or protein can be measured. Methods employing hybridization to nucleic acid probes can be employed for measuring specific mRNAs. Such methods include using nucleic acid probe arrays and using Northern blots. Messenger RNA can also be assessed using amplification techniques, such as RT-PCR. Specific proteins can be assessed using any convenient method. Most such methods will employ antibodies which are specific for the particular protein. The sequences of the mRNA (cDNA) and proteins of the markers of the present invention are provided in the sequence listing.

Methylation-sensitive restriction endonucleases can be used to detect methylated CpG dinucleotide motifs. Such endonucleases may either preferentially cleave methylated recognition sites relative to non-methylated recognition sites or preferentially cleave non-methylated relative to methylated recognition sites. Examples of the former are Acc III, Ban I, BstN I, Msp I, and Xma I. Examples of the latter are Acc II, Ava I, BssH II, BstU I, Hpa II, and Not I. Alternatively, chemical reagents can be used which selectively modify either the methylated or non-methylated form of CpG dinucleotide motifs.

Modified products can be detected directly, or after a further reaction which creates products which are easily distinguishable. Means which detect altered size and/or charge can be used to detect modified products, including but not limited to electrophoresis, chromatography, and mass spectrometry. Examples of such chemical reagents for selective modification include hydrazine and bisulfite ions. Hydrazine-modified DNA can be treated with piperidine to cleave it. Bisulfite ion-treated DNA can be treated with alkali.

One way to distinguish between modified and unmodified DNA is to hybridize oligonucleotide primers which specifically bind to one form or the other of the DNA. After hybridization, an amplification reaction can be performed and amplification products assayed. The presence of an amplification product indicates that a sample hybridized to the primer. The specificity of the primer indicates whether the DNA had been modified or not, which in turn indicates whether the DNA had been methylated or not. For example, bisulfite ions modify non-methylated cytosine bases, changing them to uracil bases. Uracil bases hybridize to adenine bases under hybridization conditions. Thus an oligonucleotide primer which comprises adenine bases in place of guanine bases would hybridize to the bisulfite-modified DNA, whereas an oligonucleotide primer containing the guanine bases would hybridize to the non-modified (methylated) cytosine residues in the DNA. Amplification using a DNA polymerase and a second primer yield amplification products which can be readily observed. Such a method is termed MSP (Methylation Specific PCR). The amplification products can be optionally hybridized to specific oligonucleotide probes which may also be specific for certain products. Alternatively, oligonucleotide probes can be used which will hybridize to amplification products from both modified and nonmodified DNA.

Another way to distinguish between modified and nonmodified DNA is to use oligonucleotide probes which may also be specific for certain products. Such probes can be hybridized directly to modified DNA or to amplification products of modified DNA. Oligonucleotide probes can be labeled using any detection system known in the art. These include but are not limited to fluorescent moieties, radioisotope labeled moieties, bioluminescent moieties, luminescent moieties, chemiluminescent moieties, enzymes, substrates, receptors, or ligands.

Test cells for diagnostic, prognostic, or personalized medicine uses can be obtained from surgical samples, such as biopsies or fine needle aspirates, from paraffin embedded tissues, from a body fluid such as bone marrow, blood, serum, lymph, cerebrospinal fluid, saliva, sputum, stool, urine, or semen. Such sources are not meant to be exhaustive, but rather exemplary.

Demethylating agents can be contacted with cells in vitro or in vivo for the purpose of restoring normal gene expression to the cell. Suitable demethylating agents include, but are not limited to 5-aza-2'-deoxycytidine, 5-aza-cytidine, Zebularine, procaine, and L-ethionine. This reaction may be used for diagnosis, for determining predisposition, and for determining suitable therapeutic regimes.

An alternative way to restore epigenetically silenced gene expression is to introduce a non-methylated polynucleotide into an ovarian cell, so that it will be expressed in the cell. Various gene therapy vectors and vehicles are known in the art and any can be used as is suitable for a particular situation. Certain vectors are suitable for short term expression and certain vectors are suitable for prolonged expression. Certain vectors are trophic for certain organs and these can be used as is appropriate in the particular situation. Vectors may be viral or non-viral. The polynucleotide can, but need not, be contained in a vector, for example, a viral vector, and can be formulated, for example, in a matrix such as a liposome, or a microbubble. The polynucleotide can be introduced into an ovarian cell by administering the polynucleotide to the subject such that it contacts the cell and is taken up by the cell and the encoded polypeptide expressed. Suitable polynucleotides are provided in the sequence listing in the odd numbered sequences of SEQ ID NO: 1-51. Polynucleotides encoding the polypeptides shown in even numbered sequences of SEQ ID NO: 2-52 can also be used. Preferably the specific polynucleotide will be one for which the patient has been tested and been found to carry a silenced version.

Marker proteins and genes as set forth in Table 2 encompass not only the particular sequences found in the publicly available database entries which are listed (as of today) and in the Sequence Listing, but also encompass variants of these sequences, including allelic variants. Variant sequences have at least 90%, at least 91%, at least 92%, at least 93%, at least 94%, at least 95%, at least 96%, at least 97%, at least 98%, or at least 99% identity to sequences in the database entries or Sequence Listing. Variant forms of the encoded proteins may comprise post-translational modifications, may result from alternatively spliced messages, etc. Any variant within the parameters described may be used if it is subject to epigenetic silencing in an ovarian cancer patient's tumor. Computer programs for determining percent identity are available in the art, including the Basic Local Alignment Search Tool (BLAST) available from the National Center for Biotechnology Information.

Cells exhibiting methylation silenced gene expression can be contacted with a demethylating agent in vivo by administering the agent to a subject. Where convenient, the demethylating agent can be administered using, for example, a catheterization procedure, at or near the site of the cells exhibiting unregulated growth in the subject, or into a blood vessel in which the blood is flowing to the site of the cells. Similarly, where an organ, or portion thereof, to be treated can be isolated by a shunt procedure, the agent can be administered via the shunt, thus substantially providing the agent to the site containing the cells. The agent also can be administered systemically or via other routes known in the art.

The polynucleotide can include, in addition to polypeptide coding sequence, operatively linked transcriptional regulatory elements, translational regulatory elements, and the like, and can be in the form of a naked DNA molecule, which can be contained in a vector, or can be formulated in a matrix such as a liposome or microbubbles that facilitates entry of the polynucleotide into the particular cell. The term "operatively linked" refers to two or more molecules that are positioned with respect to each other such that they act as a single unit and affect a function attributable to one or both molecules or a combination thereof. A polynucleotide sequence encoding a desired polypeptide can be operatively linked to a regulatory element, in which case the regulatory element confers its regulatory effect on the polynucleotide similar to the way in which the regulatory element would effect a polynucleotide sequence with which it normally is associated within a cell.

The polynucleotide encoding the desired polypeptide to be administered to a mammal or a human or to be contacted with an ovarian cell may contain a promoter sequence, which can provide constitutive or, if desired, inducible or tissue specific or developmental stage specific expression of the polynucleotide, a poly-A recognition sequence, and a ribosome recognition site or internal ribosome entry site, or other regulatory elements such as an enhancer, which can be tissue specific. The vector also may contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison, Wis.; Stratagene, La Jolla, Calif.; GIBCO/BRL, Gaithersburg, Md.) or can be constructed by one skilled in the art (see, for example, Meth. Enzymol., Vol. 185, Goeddel, ed. (Academic Press, Inc., 1990); Jolly, Canc. Gene Ther. 1:51-64, 1994; Flotte, J. Bioenerg. Biomemb. 25:37-42, 1993; Kirshenbaum et al., J. Clin. Invest. 92:381-387, 1993; each of which is incorporated herein by reference).

A tetracycline (tet) inducible promoter can be used for driving expression of a polynucleotide encoding a desired polypeptide. Upon administration of tetracycline, or a tetracycline analog, to a subject containing a polynucleotide operatively linked to a tet inducible promoter, expression of the encoded polypeptide is induced. The polynucleotide alternatively can be operatively linked to tissue specific regulatory element, for example, a liver cell specific regulatory element such as an α.-fetoprotein promoter (Kanai et al., Cancer Res. 57:461-465, 1997; He et al., J. Exp. Clin. Cancer Res. 19:183-187, 2000) or an albumin promoter (Power et al., Biochem. Biophys. Res. Comm. 203:1447-1456, 1994; Kuriyama et al., Int. J. Cancer 71:470-475, 1997); a muscle cell specific regulatory element such as a myoglobin promoter (Devlin et al., J. Biol. Chem. 264:13896-13901, 1989; Yan et al., J. Biol. Chem. 276:17361-17366, 2001); a prostate cell specific regulatory element such as the PSA promoter (Schuur et al., J. Biol. Chem. 271:7043-7051, 1996; Latham et al., Cancer Res. 60:334-341, 2000); a pancreatic cell specific regulatory element such as the elastase promoter (Ornitz et al., Nature 313:600-602, 1985; Swift et al., Genes Devel. 3:687-696, 1989); a leukocyte specific regulatory element such as the leukosialin (CD43) promoter (Shelley et al., Biochem. J. 270:569-576, 1990; Kudo and Fukuda, J. Biol. Chem. 270: 13298-13302, 1995); or the like, such that expression of the polypeptide is restricted to particular cell in an individual, or to particular cells in a mixed population of cells in culture, for example, an organ culture. Regulatory elements, including tissue specific regulatory elements, many of which are commercially available, are well known in the art (see, for example, InvivoGen; San Diego, Calif.).

Viral expression vectors can be used for introducing a polynucleotide into an ovarian cell, particularly an ovarian cell in a subject. Viral vectors provide the advantage that they can infect host cells with relatively high efficiency and can infect specific cell types. For example, a polynucleotide encoding a desired polypeptide can be cloned into a baculovirus vector, which then can be used to infect an insect host cell, thereby providing a means to produce large amounts of the encoded polypeptide. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, hepatitis virus vectors, vaccinia virus vectors, and the like (see Miller and Rosman, BioTechniques 7:980-990, 1992; Anderson et al., Nature 392: 25-30 Suppl., 1998; Verma and Somia, Nature 389:239-242, 1997; Wilson, New Engl. J. Med. 334:1185-1187 (1996), each of which is incorporated herein by reference).

A polynucleotide, which can optionally be contained in a vector, can be introduced into an ovarian cell by any of a variety of methods known in the art (Sambrook et al., supra, 1989; Ausubel et al., Current Protocols in Molecular Biology, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. A particularly useful method comprises incorporating the polynucleotide into microbubbles, which can be injected into the circulation. An ultrasound source can be positioned such that ultrasound is transmitted to the target organ or tissue, whereby circulating microbubbles containing the polynucleotide are disrupted at the site of the target due to the ultrasound, thus providing the polynucleotide at the site of the target. The selection of a particular method will depend, for example, on the cell into which the polynucleotide is to be introduced, as well as whether the cell is in culture or in situ in a body.

Introduction of a polynucleotide into an ovarian cell by infection with a viral vector can efficiently introduce the nucleic acid molecule into an ovarian cell. Moreover, viruses are very specialized and can be selected as vectors based on an ability to infect and propagate in one or a few specific cell types. Thus, their natural specificity can be used to target the nucleic acid molecule contained in the vector to specific cell types. A vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events. A polynucleotide of the invention, or a vector containing the polynucleotide can be contained in a cell, for example, a host cell, which allows propagation of a vector containing the polynucleotide, or a helper cell, which allows packaging of a viral vector containing the polynucleotide. The polynucleotide can be transiently contained in the cell, or can be stably maintained due, for example, to integration into the cell genome.

A polypeptide according to any of even numbered sequences between SEQ ID NO: 2-52 or a variant thereof, as discussed above, can be administered directly to the site of a cell exhibiting unregulated growth in the subject. The polypeptide can be produced and isolated, and formulated as desired, using methods as disclosed herein, and can be contacted with the cell such that the polypeptide can cross the cell membrane of the target cells. The polypeptide may be provided as part of a fusion protein, which includes a peptide or polypeptide component that facilitates transport across cell membranes. For example, a human immunodeficiency virus (HIV) TAT protein transduction domain or a nuclear localization domain may be fused to the marker of interest. The administered polypeptide can be formulated in a matrix that facilitates entry of the polypeptide into a cell.

An agent such as a demethylating agent, a polynucleotide, or a polypeptide is typically formulated in a composition suitable for administration to the subject. Thus, the invention provides compositions containing an agent that is useful for restoring regulated growth to a cell exhibiting unregulated growth due to methylation silenced transcription of one or more genes. The agents are useful as medicaments for treating a subject suffering from a pathological condition associated with such unregulated growth. Such medicaments generally include a carrier. Acceptable carriers are well known in the art and include, for example, aqueous solutions such as water or physiologically buffered saline or other solvents or vehicles such as glycols, glycerol, oils such as olive oil or injectable organic esters. An acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know or readily be able to determine an acceptable carrier, including a physiologically acceptable compound. The nature of the carrier depends on the physico-chemical characteristics of the therapeutic agent and on the route of administration of the composition. Administration of therapeutic agents or medicaments can be by the oral route or parenterally such as intravenously, intramuscularly, subcutaneously, transdermally, intranasally, intrabronchially, vaginally, rectally, intratumorally, or other such method known in the art. The pharmaceutical composition also can contain one more additional therapeutic agents.

The therapeutic agents can be incorporated within an encapsulating material such as into an oil-in-water emulsion, a microemulsion, micelle, mixed micelle, liposome, microsphere, microbubbles or other polymer matrix (see, for example, Gregoriadis, Liposome Technology, Vol. 1 (CRC Press, Boca Raton, Fla. 1984); Fraley, et al., Trends Biochem. Sci., 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225, 212, each of which is incorporated herein by reference) are an example of such encapsulating materials particularly useful for preparing a composition useful in a method of the invention, and other "masked" liposomes similarly can be used, such liposomes extending the time that the therapeutic agent remain in the circulation. Cationic liposomes, for example, also can be modified with specific receptors or ligands (Morishita et al., J. Clin. Invest., 91:2580-2585 (1993), which is incorporated herein by reference). In addition, a polynucleotide agent can be introduced into a cell using, for example, adenovirus-polylysine DNA complexes (see, for example, Michael et al., J. Biol. Chem. 268:6866-6869 (1993), which is incorporated herein by reference).

The route of administration of the composition containing the therapeutic agent will depend, in part, on the chemical structure of the molecule. Polypeptides and polynucleotides, for example, are not efficiently delivered orally because they can be degraded in the digestive tract. However, methods for chemically modifying polypeptides, for example, to render them less susceptible to degradation by endogenous proteases or more absorbable through the alimentary tract may be used (see, for example, Blondelle et al., supra, 1995; Ecker and Crook, supra, 1995).

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the composition to treat a pathologic condition in a subject depends on many factors including the age and general health of the subject as well as the route of administration and the number of treatments to be administered. In view of these factors, the skilled artisan would adjust the particular dose as necessary. In general, the formulation of the composition and the routes and frequency of administration are determined, initially, using Phase I and Phase II clinical trials.

The composition can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

Although accuracy and sensitivity may be achieved by using a combination of markers, such as 5 or 6 markers, practical considerations may dictate use of smaller combinations. Any combination of markers for ovarian cancer may be used which comprises 2, 3, 4, or 5 markers. Each of the combinations for two through six markers are listed in Table 1 found on CD-ROM. Other combinations of more than six markers can be readily envisioned given the specific disclosures of individual markers provided herein. Any number of markers from 1 to 23 can be used, inclusive.

Kits according to the present invention are assemblages of reagents for testing methylation. They are typically in a package which contains all elements, optionally including instructions. The package may be divided so that components are not mixed until desired. Components may be in different physical states. For example, some components may be lyophilized and some in aqueous solution. Some may be frozen. Individual components may be separately packaged within the kit. The kit may contain reagents, as described above for differentially modifying methylated and non-methylated cytosine residues. Desirably the kit will contain oligonucleotide primers which specifically hybridize to regions within 1 kb of the transcription start sites of the genes identified in Table 2. Typically the kit will contain both a forward and a reverse primer for a single gene. Specific hybridization typically is accomplished by a primer having at least 12, 14, 16, 18, or 20 contiguous nucleotides which are complementary to the target template. Often the primer will be 100% identical to the target template. If there is a sufficient region of complementarity, e.g., 12, 15, 18, or 20 nucleotides, then the primer may also contain additional nucleotide residues that do not interfere with hybridization but may be useful for other manipulations. Exemplary of such other residues may be sites for restriction endonuclease cleavage, for ligand binding or for factor binding or linkers. The oligonucleotide primers may or may not be such that they are specific for modified methylated residues. The kit may optionally contain oligonucleotide probes. The probes may be specific for sequences containing modified methylated residues or for sequences containing non-methylated residues. Like the primers as described above, specific hybridization is accomplished by having a sufficient region of complementarity to the target. The kit may optionally contain reagents for modifying methylated cytosine residues. The kit may also contain components for performing amplification, such as a DNA polymerase and deoxyribonucleotides. Means of detection may also be provided in the kit, including detectable labels on primers or probes. Kits may also contain reagents for detecting gene expression for one of the markers of the present invention (Table 2). Such reagents may include probes, primers, or antibodies, for example. In the case of enzymes or ligands, substrates or binding partners may be sued to assess the presence of the marker.

In one aspect of the invention, the maker gene(s) is contacted with hydrazine, which modifies cytosine residues, but not methylated cytosine residues, then the hydrazine treated gene sequence is contacted with a reagent such as piperidine, which cleaves the nucleic acid molecule at hydrazine modified cytosine residues, thereby generating a product comprising fragments. By separating the fragments according to molecular weight, using, for example, an electrophoretic, chromatographic, or mass spectrographic method, and comparing the separation pattern with that of a similarly treated corresponding non-methylated gene sequence, gaps are apparent at positions in the test gene that contained methylated cytosine residues. The presence of gaps is indicative of methylation of a cytosine residue in the CpG dinucleotide in the target gene of the test cell.

Bisulfite ions, for example, sodium bisulfite, convert non-methylated cytosine residues to bisulfite modified cytosine residues. The bisulfite ion treated gene sequence can be exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. The sulfonate group can be removed by exposure to alkaline conditions, resulting in the formation of uracil. The DNA can be amplified, for example, by PCR, and sequenced to determine whether CpG sites are methylated in the DNA of the sample. Uracil is recognized as a thymine by Taq polymerase and, upon PCR, the resultant product contains cytosine only at the position where 5-methylcytosine was present in the starting template DNA. One can compare the amount or distribution of uracil residues in the bisulfite ion treated gene sequence of the test cell with a similarly treated corresponding non-methylated gene sequence. A decrease in the amount or distribution of uracil residues in the gene from the test cell indicates methylation of cytosine residues in CpG dinucleotides in the gene of the test cell. The amount or distribution of uracil residues also can be detected by contacting the bisulfite ion treated target gene sequence, following exposure to alkaline conditions, with an oligonucleotide that selectively hybridizes to a nucleotide sequence of the target gene that either contains uracil residues or that lacks uracil residues, but not both, and detecting selective hybridization (or the absence thereof) of the oligonucleotide.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

Example 1

Analysis of Methylation

DNA was extracted according to standard protocols known to those of skill in the art (see, e.g., Sambrook et al., Molecular Cloning: a Laboratory Manual, 2nd Ed.; Cold Spring Harbor Laboratory Press, Plainview, N.Y., 1998, herein incorporated by reference). Briefly, methylation patterns in the CpG island of the genes were determined by chemical modification of genomic DNA with sodium bisulfite and subsequent methylation-specific PCR (MSP) according to protocols known to those of skill in the art (see, e.g. Belinsky Steven A and Palmisano William A, WO0218649). Briefly, 0.5 μg of DNA was denatured by NaOH and modified by sodium bisulfite. DNA samples were then purified using the EZ DNA Methylation Kit™ from Zymo Research, precipitated with ethanol, and resuspended in H₂O. To facilitate MSP analysis on DNA retrieved from formalin-fixed, paraffin embedded tissue, DNA was first amplified with flanking PCR primers that amplify bisulfite-modified DNA but do not preferentially amplify methylated or unmethylated DNA. The resulting fragment was used as a template for the MSP reaction. Primer sequences and the corresponding annealing temperature are indicated in Table 4.

TABLE 4

| primer | product length | filter | Tm | sequence | seq id no. |
| --- | --- | --- | --- | --- | --- |
| ASK flank up | 150 | 22 | 58.6 | 5' TTA GAA GGY GGG AAT AAT TTT G 3' | 53 |
| ASK flank down |  | 22 | 57.7 | 5' TCA ATC TCA AAC CCR AAC TCT C 3' | 54 |
| ASK Ms | 121 | 16 | 60.0 | 5' GGT GAC GGG CGG GGT 3' | 55 |
| ASK Mas |  | 20 | 60.6 | 5' AAA CCC GAA CTC TCG ATC CG 3' | 56 |
| ASK Us | 128 | 20 | 61.1 | 5' TTT TGG TGA TGG GTG GGG TT 3' | 57 |
| ASK Uas |  | 23 | 60.3 | 5' CTC AAA CCC AAA CTC TCA ATC CA 3' | 58 |
| TM4SF11 flank up | 114 | 24 | 56.7 | 5' GTA TTT GGY GTT TTA GGT TTT TAG 3' | 59 |
| TM4SF11 flank down |  | 20 | 55.7 | 5' CCC CTC CAA CRA TAA ATA CC 3' | 60 |
| TM4SF11 Ms | 91 | 25 | 60.2 | 5' TTT TAG TTT CGA CGT TTT TTG TAG C 3' | 61 |
| TM4SF11 Mas |  | 22 | 61.0 | 5' CAA CGA TAA ATA CCG ACT CCC G 3' | 62 |

TABLE 4-continued

| primer | product length | filter | Tm | sequence | seq id no. |
|---|---|---|---|---|---|
| TM4SF11 Us | 96 | 27 | 59.9 | 5' GGTTTTTAGTTTTGATGTTTTTGTAGT 3' | 63 |
| TM4SF11 Uas | | 24 | 60.4 | 5' TCCAACAATAAATACCAACTCCCA 3' | 64 |
| NDP flank up | 110 | 21 | 54.4 | 5' GGT GGG TAG AGG TTG AGT TTT 3' | 65 |
| NDP flank down | | 26 | 55.6 | 5' CCA TTA CAA TCA TAT ATC AAT CAA AC 3' | 66 |
| NDP Ms | 91 | 23 | 59.6 | 5' AGG TTG AGT TTT CGA TAA CGA GC 3' | 67 |
| NDP Mas | | 25 | 60.9 | 5' CAT ATA TCA ATC AAA CGC GTA CGA CCG 3' | 68 |
| NDP Us | 99 | 28 | 61.0 | 5' GGT AGA GGT TGA GTT TTT GAT PAT GAG T 3' | 69 |
| NDP Uas | | 28 | 59.3 | 5' AAT CAT ATA TCA ATC AAA CAT ACA ACC A 3' | 70 |
| RUNX3 flank up | 157 | 20 | 57.8 | 5' TAG TGG GGA TGG GAG GTG TT 3' | 71 |
| RUNX3 flank down | | 19 | 54.8 | 5' CCC CAA AAC CCA AAT AAA A 3' | 72 |
| RUNX3 Ms | 97 | 21 | 60.0 | 5' ATG GGA GGT GTT CGA GAC GTC 3' | 73 |
| RUNX3 Mas | | 20 | 60.3 | 5' AAC GCA TCC AAA ACG AAA CG 3' | 74 |
| RUNX3 Us | 97 | 23 | 61.2 | 5' GGA TGG GAG GTG TTT GAG ATG TT 3' | 75 |
| RUNX3 Uas | | 26 | 60.8 | 3' CTA CAA AAC ACA TCC AAA ACA AAA CA 5' | 76 |
| C11orf2 flank up | 156 | 19 | 57.6 | 5' GGG TTT GGA TTT GGG GAT T 3' | 77 |
| C11orf2 flank down | | 22 | 57.2 | 5' CAA ATC AAT CRA ATC AAA AAA A 3' | 78 |
| C11orf2 Ms | 105 | 19 | 62.9 | 5' GGG GAG GTT TCG GAG CGT C 3' | 79 |
| C11orf2 Mas | | 19 | 62.8 | 5' CAA AAA ATC GAA CCC CGC G 3' | 80 |
| C11orf2 Us | 112 | 22 | 62.8 | 5' GAG GGG GAG GTT TTG GAG TGT T 3' | 81 |
| C11orf2 Uas | | 23 | 62.2 | 5' AAT CCA AAA AAT CAA ACC CCA CA 3' | 82 |
| ACTN1 flank up | 121 | 20 | 57.5 | 5' GAG GTG GGG TGT TGG GTT AT 3' | 83 |
| ACTN1 flank down | | 19 | 57.9 | 5' CCC CCA AAA AAA CCT ACC C 3' | 84 |
| ACTN1 Ms | 91 | 18 | 61.0 | 5' TAG GCG TTT GGC GGA AGC 3' | 85 |
| ACTN1 Mas | | 18 | 60.1 | 5' ACC TAC CCG CCA ACG ACG 3' | 86 |
| ACTN1 Us | 102 | 24 | 60.6 | 5' GGG TTA TAG GTG TTT GGT GGA AGT 3' | 87 |
| ACTN1 Uas | | 23 | 60.2 | 5' AAA AAA CCT ACC CAC CAA CAA CA 3' | 88 |
| CGI-38 flank up | 160 | 24 | 56.9 | 5' GAG TYG TTT GGG TTG TAG TTT TAT 3' | 89 |
| CGI-38 flank down | | 28 | 56.1 | 5' ATC TAA ATC TCC TAT AAA CTT CTA CCT C 3' | 90 |
| CGI-38Ms | 111 | 19 | 61.0 | 5' TCG GGA GTC GGT AGG AGC 3' | 91 |
| CGI-38 Mas | | 25 | 59.7 | 5' CTC GCG ACT ACT CCT AAA ATA TAC G 3' | 92 |
| CGI-38 Us | 121 | 24 | 60.6 | 5' TTT ATT TGG GAG TTG GTA GGG AGT 3' | 93 |
| CGI-38 Uas | | 30 | 59.7 | 5' TCT ACC TCA CAA CTA CTC CTA AAA TAT ACA 3' | 94 |
| DEK flank up | 131 | 20 | 56.3 | 5' GAA GTY GTT TTT GGG GAT TG 3' | 95 |
| DEK flank down | | 19 | 56.0 | 5' ATC CTC CTA CTC CCR CAA A 3' | 96 |
| DEK Ms | 105 | 20 | 62.0 | 5' GGA TTG GAC GTT GCG GTT TC 3' | 97 |
| DEK Mas | | 19 | 61.4 | 5' CCG CAA ACA AAA CCG AAC G 3' | 98 |
| DEK Us | 110 | 22 | 59.8 | 5' GGG GAT TGA GTG TTG TGG TTT T 3' | 99 |
| DEK Uas | | 22 | 59.5 | 5' CTC CCA CAA ACA AAA CCA AAC A 3' | 100 |
| HDGF flank up | 147 | 25 | 55.4 | 5' GAY GTT TTT AGG GTT ATT TTT TAT A 3' | 101 |
| HDGF flank down | | 25 | 55.6 | 5' TCC ACA AAT ATT TAC TAA ACA CCC 3' | 102 |
| HDGF Ms | 115 | 26 | 59.0 | 5' GTT ATT TTT TAT ACG TAA GTA CGC GC 3' | 103 |
| HDGF Mas | | 20 | 59.6 | 5' ACC CGC GAT TCT AAA CAA CG 3' | 104 |
| HDGF Us | 124 | 29 | 60.3 | 5' AGG GTT ATT TTT TAT ATG GTA AGT ATG GT 3' | 105 |
| HDGF Uas | | 26 | 60.1 | 5' CTA AAC ACC CAC AAT TCT AAA CAA CA 3' | 106 |
| HPSE flank up | 133 | 19 | 56.3 | 5' GGY GGG AGG AAG TGT TAG A 3' | 107 |
| HPSE flank down | | 21 | 57.6 | 5' CCC CAA AAA CAA CAA CAT CAA 3' | 108 |
| HPSE Ms | 112 | 24 | 60.4 | 5' TTA GAG TTT TCG ATT TTT CGT TGC 3' | 109 |
| HPSE Mas | | 22 | 60.0 | 5' AAC AAC AAC ATC AAC GAC GAC G 3' | 110 |
| HPSE Us | 121 | 29 | 61.4 | 5' AAG TGT TAG AGT TTT TGA TTT TTT GTT GT 3' | 111 |
| HPSE Uas | | 26 | 61.8 | 5' CAA AAA CAA CAA CAT CAA CAA CAA CA 3' | 112 |
| TNFRFS10B flank up | 122 | 20 | 57.3 | 5' GTT TTT GGG AAG GGG AGA AG 3' | 113 |
| TNFRSF10B flank down | | 28 | 56.3 | 5' AAT TAA AAA AAA CAC TTA AAA AAT TAA C 3' | 114 |
| TNFRSF10B Ms | 81 | 22 | 60.8 | 5' GAT TAA GAC GCG TTT GGA AAG C 3' | 115 |
| TNFRSF10B Mas | | 20 | 61.2 | 5' ATT AAC GCC TCC CGA AAT CG 3' | 116 |
| TNFRSF10B Us | 93 | 28 | 62.8 | 5' GGA GAA GAT TAA GAT GTG TTT GGA AAG T 3' | 117 |
| TNFRSF10B Uas | | 26 | 61.5 | 5' TAA AAA ATT AAC ACC TCC CAA AAT CA 3' | 118 |
| TTK flank up | 134 | 25 | 56.5 | 5' TTA AAT TGG AAA GAT TAG GAA AGT T 3' | 119 |
| TTK flank down | | 18 | 57.1 | 5' TCA AAC TAA ACC CRC CCC 3' | 120 |
| TTK Ms | 104 | 23 | 61.3 | 5' ATT AGG AAA GTT CGT TTA CGG GC 3' | 121 |
| TTK Mas | | 20 | 62.6 | 5' CGA AAA AAC CTA CGA CCG CG 3' | 122 |
| TTK Us | 111 | 28 | 62.5 | 5' GAA AGA TTA GGA AAG TTT GTT TAT GGG T 3' | 123 |
| TTK Uas | | 22 | 61.2 | 5' CCC GAA AAA ACC TAC AAC CAC A 3' | 124 |

TABLE 4-continued

| primer | product length | filter | Tm | sequence | seq id no. |
|---|---|---|---|---|---|
| HEC flank up | 151 | 19 | 57.4 | 5' TTG GGG TGAY GTA GTT GGG 3' | 125 |
| HEC flank down | | 19 | 58.0 | 5' CCA AAT CCT TCC TCR ACC C 3' | 126 |
| HEC Ms | 99 | 22 | 61.5 | 5' CGT AGT TGG GCG CGA TTA GTA C 3' | 127 |
| HEC Mas | | 18 | 61.6 | 5' TCT CCG CCG ACG CTA ACG 3' | 128 |
| HEC Us | 113 | 27 | 60.3 | 5' GGT GAT GTA GTT GGG TGT GAT TAG TAT 3' | 129 |
| HEC Uas | | 27 | 60.7 | 5' ATT AAA AAT TCT CCA CCA ACA CTA ACA 3' | 130 |
| MYBL2 flank up | 139 | 23 | 57.3 | 5' GGT TTT YGT TAT GTG GGA TAT TT 3' | 131 |
| MYBL2 flank down | | 19 | 57.6 | 5' ACC CAA ACC CTC CAA AAC C 3' | 132 |
| MYBL2 Ms | 99 | 22 | 60.9 | 5' TTG GGT CGT TTC GGA TTG ATA C 3' | 133 |
| MYBL2 Mas | | 23 | 61.5 | 5' CCG ACT ACA AAA CAA AAA CGA CG 3' | 134 |
| MYBL2 Us | 104 | 24 | 59.9 | 5' TTT TGG GTT GTT TTG GAT TGA TAT 3' | 135 |
| MYBL2 Uas | | 26 | 60.0 | 5' AAA CCA ACT ACA AAA CAA AAA CAA CA 3' | 136 |
| POLR3D flank up | 149 | 24 | 57.8 | 5' TTT AGG TAA TAT GTY GGA AGG AAA 3' | 137 |
| POLR3D flank down | | 24 | 57.4 | 5' CCC TAA AAC RAA TAA AAA AAA AAC 3' | 138 |
| POLR3D Ms | 106 | 22 | 59.9 | 5' TTT AGT ACG TCG GGA GGG TTT C 3' | 139 |
| POLR3D Mas | | 23 | 60.4 | 5' AAC GAA TAA AAA AAA AAC GAC CG 3' | 140 |
| POLR3D Us | 113 | 25 | 59.8 | 5' GAG TTT AGT ATG TTG GGA GGG TTT T 3' | 141 |
| POLR3D Uas | | 27 | 59.6 | 5' CTA AAA CAA ATA AAA AAA AAA CAA CCA 3' | 142 |
| TK1 flank up | 110 | 24 | 57.7 | 5' TTT TAG GTT TTT TTA GTT TTT GGG 3' | 143 |
| TK1 flank down | | 20 | 57.4 | 5' CAT AAA ACC AAT CAA CRC CC 3' | 144 |
| TK1 Ms | 91 | 23 | 60.8 | 5' TTT AGT TTT TGG CGT ACG TT TC 3' | 145 |
| TK1 Mas | | 17 | 59.4 | 5' CAA TCA ACG CCC GAC CG 3' | 146 |
| TK1 Us | 100 | 27 | 60.8 | 5' TTT TTT TAG TTT TTG GGT GTA TGT TTT 3' | 147 |
| TK1 Uas | | 22 | 61.0 | 5' AAA ACC AAT CAA CAC CCA ACC A 3' | 148 |
| TRIP13 flank up | 114 | 22 | 56.5 | 5' TTA TYG TTT TTT GGT TTT GGT T 3' | 149 |
| TRIP13 flank down | | 20 | 56.0 | 5' ACA AAA CCA CTT CCT ACC RC 3' | 150 |
| TRIP13 Ms | 93 | 20 | 61.8 | 5' GGT TTT GGT TGG TCG TTC GC 3' | 151 |
| TRIP13 Mas | | 18 | 62.4 | 5' CTT CCT ACC GCG ACC CCG 3' | 152 |
| TRIP13 Us | 99 | 23 | 60.9 | 5' TTT GGT TTT GGT TGG TTG TTT GT 3' | 153 |
| TRIP13 Uas | | 21 | 61.0 | 5' CCA CTT CCT ACC ACA ACC CA 3' | 154 |
| BARD1 flank up | 105 | 25 | 56.6 | 5' GTT TAG TTT TTA GGT TTY GTT TTT T 3' | 155 |
| BARD1 flank down | | 24 | 57.5 | 5' AAA CAA AAC AAA ACR ACT AAA ACC 3' | 156 |
| BARD1 Ms | 81 | 22 | 60.2 | 5' GGT TTC GTT TTT TCG TTA AG C 3' | 157 |
| BARD1 Mas | | 21 | 60.5 | 5' ACG ACT AAA ACC GAA ATC CCG 3' | 158 |
| BARD1 Us | 89 | 27 | 60.4 | 5' TTT TAG TTT TGT TTT TTG GTT A AGT 3' | 159 |
| BARD1 Uas | | 24 | 59.6 | 5' AAA ACA ACT AAA ACC AAA ATC CCA 3' | 160 |
| FANCG flank up | 133 | 26 | 58.5 | 3' GTT TTT AGT TAT YGT TTT TTG GAA AT 5' | 161 |
| FANCG flank down | | 21 | 59.1 | 3' CCC CAA ATC CTC CTA AAT TCC 5' | 162 |
| FANCG Ms | 95 | 23 | 64.3 | 3' TTG GAA ATA TTA TTC GTC GGG GC 5' | 163 |
| FANCG Mas | | 19 | 65 | 3' CCG CTT CCA CCG AAA ACC G 5' | 164 |
| FANCG Us | 108 | 28 | 64.8 | 3' GTT TTT TGG AAA TAT TAT TTG TTG GGT 5' | 165 |
| FANCG Uas | | 27 | 64.2 | 3' CTA AAT TCC CTC TTC GAC CTA AAA CCT 5' | 166 |
| SMPD2 flank up | | 22 | 55.3 | 5' GGT TGG GTT TTT TTT TAA TTT T 3' | 167 |
| SMPD2 flank down | | 21 | 56.5 | 5' TTT TCC CTA AAA ATC CRA AAA 3' | 168 |
| SMPD2 Ms | | 20 | 60 | 5' GCG TTT GTT GTT GGG TCG TC 3' | 169 |
| SMPD2 Mas | | 19 | 59.4 | 5' CCC GAA TAA ACG ACT CCC G 3' | 170 |
| SMPD2 Us | | 23 | 59.3 | 5' TTT GTG TTT GTT GTT GGG TTG TT 3' | 171 |
| SMPD2 Uas | | 21 | 60.8 | 5' CCC CCA AAT AAA CAA CTC CCA 3' | 172 |

All PCRs were performed with controls for unmethylated alleles (DNA from normal lymphocytes), methylated alleles [normal lymphocyte DNA treated in vitro with SssI methyltransferase (New England Biolabs)], and a control without DNA. Ten µl of each MSP reaction were directly loaded onto nondenaturing 6% polyacrylamide gels, stained with ethidium bromide, and visualized under UV illumination. Primer sequences for the first round PCR are indicated as flank up and flank down. Primer sequences for the subsequent unmethylated reaction are indicated as Us (sense) and Uas (antisense) and for the methylated reaction Ms (sense) and Mas (antisense).

Example 2

Specimens

Specimens comprised normal tubae (n=8; derived from women with an extra-uterine pregnancy), serous borderline tumors (SBT n=36 of which 24 were paraffin-embedded samples, and 12 were fresh frozen) and grade I and grade III serous carcinomas(SCA n=75, of which 46 were paraffin-embedded samples, and 26 were fresh frozen). Tumor material was retrieved from the tumor bank of the department of Pathology, University Medical Centre Leiden (see JCO 2005 Sieben et al) and from the department of Pathology, University Hospital Maastricht. Tubae were.

Cell line material was obtained from Ovar3, T29 and T29K cell lines.

Example 3

Promoter hypermethylation was examined in all specimen. Tables 5 and 6 show the results obtained and the SCA grading for each of the subjects.

TABLE 5

| | | | | Tubae | | | | | |
|---|---|---|---|---|---|---|---|---|---|
| sample | RASSF1A | RASSF2A | WIF1 | APC | SFRP1 | SFRP2 | SFRP4 | SFRP5 | MGMT |
| T1 | U | U | U | U | U | U | U | U | U |
| T2 | U | U | U | U | U | U | M | U | U |
| T3 | U | U | U | U | U | U | U | U | U |
| T4 | U | U | U | U | U | U | U | U | M |
| T5 | U | U | U | U | U | U | U | U | U |
| T6 | U | U | U | U | U | U | U | U | U |
| T7 | U | U | U | U | U | U | M | U | U |
| T8 | U | U | U | M | U | U | M | U | U |

| sample | BRCA1 | MLH1 | FANCF | p14 | p16 | CHFR | GATA4 | GATA5 | HLTF |
|---|---|---|---|---|---|---|---|---|---|
| T1 | M | U | U | U | U | U | U | U | U |
| T2 | U | U | U | U | M | U | M | U | U |
| T3 | U | U | U | U | U | U | U | U | U |
| T4 | U | U | U | U | U | U | U | U | U |
| T5 | U | U | U | U | U | U | U | U | U |
| T6 | U | U | U | U | M | U | U | U | U |
| T7 | U | U | U | U | U | U | U | U | U |
| T8 | U | U | U | U | U | U | M | U | U |

| gene | frequency |
|---|---|
| RASSF1A | 0/8 |
| RASSF2A | 0/8 |
| WIF1 | 0/8 |
| APC | 1/8 (13%) |
| SFRP1 | 0/8 |
| SFRP2 | 0/8 |
| SFRP4 | 3/8 (38%) |
| SFRP5 | 0/8 |
| MGMT | 1/8 (13%) |
| BRCA1 | 1/8 (13%) |
| MLH1 | 0/8 |
| FANCF | 0/8 |
| p14 | 0/8 |
| p16 | 2/8 (25%) |
| CHFR | 0/8 |
| GATA4 | 2/8 (25%) |
| GATA5 | 0/8 |
| HLTF | 0/8 |

U = unmethylated;
M = methylated

TABLE 6

| | | | | | | | | CGI- | | | | | | | |
|---|---|---|---|---|---|---|---|---|---|---|---|---|---|---|---|
| sample | diagnosis | grade | NDP | TM4SF11 | RUNX3 | TNFRSF10B | DEK | 38 | HEC | MYBL2 | TTK | BARD1 | ACTN1 | C11ORF2 | SMPD2 |
| T1 | tuba | | U | U | U | U | U | U | U | U | U | U | U | U | U |
| T2 | tuba | | u | U | U | M | U | U | U | U | U | U | U | U | U |
| T3 | tuba | | U | U | U | U | U | U | U | M | U | U | U | U | U |
| T4 | tuba | | U | U | U | U | U | U | U | U | U | M | M | U | M |
| T5 | tuba | | M | U | U | U | M | U | U | M | U | U | U | U | U |
| T6 | tuba | | U | U | U | U | U | U | M | U | U | U | U | U | U |
| T7 | tuba | | M | U | U | U | U | U | U | M | U | U | U | U | U |
| T8 | tuba | | M | U | U | U | U | M | M | M | U | U | U | U | M |
| 529 | SBT | | M | U | U | U | U | U | U | U | U | U | U | U | U |
| 530 | SBT | | U | U | U | M | U | U | U | U | U | U | U | GR | U |
| 531 | SBT | | U | U | U | M | U | U | U | U | U | M | U | U | U |
| 533 | SBT | | U | U | U | M | U | U | U | U | U | U | U | U | U |
| 535C | SBT | | U | U | U | U | U | U | U | U | U | U | U | U | U |
| 536 | SBT | | U | U | U | M | U | U | U | U | U | U | U | U | U |
| 536A | SBT | | M | U | U | U | U | U | U | U | U | U | U | U | U |
| 537A | SBT | | U | M | M | U | U | U | M | M | U | U | U | U | U |
| 537B | SBT | | M | U | M | U | U | U | U | U | U | U | U | U | U |
| 538 | SBT | | U | U | U | U | U | U | U | U | U | U | U | U | U |
| 539A | SBT | | M | U | M | M | U | U | M | M | U | U | U | U | U |
| 540 | SBT | | U | U | M | M | M | U | U | U | U | U | U | U | U |
| 541A | SBT | | U | U | M | M | M | U | U | M | U | U | U | U | U |
| 542 | SBT | | U | U | U | U | U | U | U | U | U | U | U | GR | U |
| 550C | SBT | | M | U | M | M | U | U | U | M | U | U | U | U | U |
| 584 | SBT | | M | U | U | U | U | U | U | U | U | U | U | U | U |
| 592A | SBT | | U | U | U | M | U | U | U | U | U | U | U | U | U |
| 594A | SBT | | U | U | U | M | U | M | M | U | U | U | U | U | U |
| 596A | SBT | | M | U | U | U | U | U | U | M | U | U | U | U | U |
| 597A | SBT | | M | U | U | U | U | U | U | M | U | U | U | U | M |
| 598A | SBT | | U | U | U | U | U | U | U | U | U | U | U | U | U |
| 599A | SBT | | U | U | U | U | U | U | U | U | U | U | U | U | U |
| 600A | SBT | | U | U | U | U | U | U | U | U | U | U | U | U | U |
| 601A | SBT | | U | U | U | U | U | U | M | U | U | U | U | U | U |
| 602A | SBT | | U | U | U | U | U | U | U | U | U | U | U | U | U |
| 615-1 | SBT | | U | U | U | M | U | U | U | U | U | U | M | U | U |
| 615-2 | SBT | | U | U | U | U | U | U | U | U | U | U | U | U | GR |
| V2 | SBT | | M | U | M | U | U | U | U | U | U | U | U | U | U |
| V7 | SBT | | M | U | U | M | U | U | U | U | U | U | M | U | U |
| V11 | SBT | | U | U | U | U | U | U | U | U | U | U | U | U | U |
| V61 | SBT | | M | U | M | U | U | U | U | U | U | U | U | U | U |
| V61A | SBT | | U | U | U | U | U | U | U | U | U | U | U | U | U |
| V81 | SBT | | U | U | M | U | U | M | M | U | U | U | M | U | U |
| V82 | SBT | | U | U | M | M | U | U | M | U | U | U | U | U | U |
| V82A | SBT | | U | U | U | U | U | U | U | U | U | U | U | U | U |
| V110 | SBT | | U | U | U | U | U | U | U | U | U | U | U | U | U |
| V150 | SBT | | M | U | U | M | U | U | GR | U | U | U | M | U | U |
| V195 | SBT | | U | U | U | U | U | U | U | U | U | U | M | U | U |
| V220 | SBT | | U | U | U | U | U | U | U | U | U | U | M | U | M |
| V244 | SBT | | U | U | U | M | U | M | M | M | U | U | M | U | U |
| V245 | SBT | | U | U | U | M | U | M | U | U | U | M | M | U | U |
| 544B | SCA | II | M | U | U | M | U | U | U | M | U | U | M | U | U |
| 545A | SCA | II | U | U | U | GR | GR | GR | GR | U | GR | GR | GR | U | U |
| 546 | SCA | III | U | U | M | U | U | U | U | U | U | U | M | M | U | M |
| 547 | SCA | II | U | U | U | U | U | U | U | U | U | U | U | U | U |
| 548 | SCA | II | U | U | U | U | U | U | U | U | U | M | M | U | M |
| 549A | SCA | II | U | U | U | M | U | U | U | U | U | M | M | U | U |
| 549C | SCA | II | U | U | U | M | U | U | M | M | U | M | U | U | M |
| 551A | SCA | II | U | U | U | M | U | U | M | U | U | U | U | U | U |
| 551B | SCA | II | U | U | U | U | U | U | U | U | U | U | U | U | U |
| 552 | SCA | II | U | M | U | U | U | U | U | U | U | U | U | U | U |
| 553 | SCA | III | U | U | U | U | U | U | U | U | U | M | M | U | U |
| 554 | SCA | III | M | M | M | M | U | M | U | U | U | M | M | U | U |
| 555 | SCA | III | M | U | M | U | U | U | U | U | U | U | U | U | U |
| 556 | SCA | III | U | U | U | M | U | U | U | U | U | U | U | U | U |
| 557C | SCA | I | M | U | U | U | U | U | U | U | M | U | M | U | U |
| 558 | SCA | III | U | U | U | M | U | U | M | U | U | U | U | U | U |
| 559 | SCA | ? | M | U | M | U | U | GR | U | U | U | U | U | U | U |
| 560 | SCA | III | U | U | U | M | U | U | U | U | U | U | M | U | U |
| 561A | SCA | I | U | U | U | U | U | U | U | U | U | U | M | U | U |
| 561B | SCA | I | U | M | M | M | U | U | U | U | U | U | U | U | U |
| 562 | SCA | II | U | U | U | U | U | U | U | U | U | U | U | U | U |
| 563 | SCA | III | M | U | M | U | M | U | U | U | U | U | U | U | U |
| 564B | SCA | III | U | U | U | U | U | U | U | U | U | U | M | U | U |
| 565 | SCA | III | U | U | U | U | U | U | U | U | U | U | U | U | U |
| 566 | SCA | III | U | U | U | U | U | U | U | U | U | U | U | U | U |

TABLE 6-continued (below) MSP Metascore

| | | | | | | | | | | | | | | | | |
|---|---|---|---|---|---|---|---|---|---|---|---|---|---|---|---|---|
| 567 | SCA | ? | U | M | U | M | U | U | M | U | U | U | U | U | U | U |
| 568A | SCA | ? | U | U | U | U | U | U | U | U | U | U | GR | U | U |
| 569 | SCA | III | M | U | U | M | U | U | M | M | U | U | M | U | U |
| 570A | SCA | II | U | M | U | U | U | U | M | U | U | U | U | U | U |
| 571A | SCA | III | U | M | U | U | U | U | U | M | U | M | M | U | M |
| 572A | SCA | II | U | U | M | U | U | U | U | U | U | U | U | U | U |
| 572B | SCA | II | U | U | U | U | U | U | U | U | U | U | U | U | U |
| 573 | SCA | ? | U | U | U | U | U | U | U | U | U | U | U | U | U |
| 574 | SCA | III | U | U | U | M | M | U | U | U | U | U | U | U | U |
| 575 | SCA | II | M | U | U | M | M | U | M | U | U | M | U | U | U |
| 576 | SCA | I | U | M | U | M | U | M | U | U | U | U | U | U | U |
| 578 | SCA | III | U | U | U | U | U | U | U | U | U | U | U | U | U |
| 579 | SCA | III | U | U | U | U | U | U | U | M | U | U | M | U | U |
| 580 | SCA | I | U | U | U | U | U | U | U | U | U | U | M | U | U |
| 581 | SCA | II | M | U | U | U | U | U | U | U | U | U | U | U | U |
| 582 | SCA | ? | U | U | U | U | U | U | U | U | U | U | U | U | U |
| 583 | SCA | ? | U | U | U | M | U | U | U | U | U | U | U | U | U |
| 585 | SCA | III | U | U | U | U | U | U | U | U | U | M | M | U | U |
| 586 | SCA | III | U | U | U | U | U | GR | U | U | U | U | U | U | U |
| 587 | SCA | III | U | U | U | M | U | U | U | U | U | U | U | U | U |
| 588 | SCA | III | GR | GR | GR | U | GR | GR | U | U | GR | GR | GR | GR | GR |
| 589 | SCA | II | U | U | U | U | U | U | U | U | U | U | U | U | U |
| 591 | SCA | ? | M | U | U | U | U | U | U | U | U | U | U | U | U |
| 593 | SCA | III | U | U | M | M | M | U | U | U | U | U | U | U | M |
| 595 | SCA | II | U | U | M | M | U | U | U | U | U | U | U | U | U |
| V1 | SCA | I | M | U | U | M | U | U | M | U | U | U | U | U | U |
| V27 | SCA | III | U | U | U | M | M | M | U | M | U | U | M | U | U |
| V40 | SCA | III | U | U | U | M | U | U | U | U | U | M | U | U | U |
| V46 | SCA | III | U | U | M | M | M | U | M | U | U | M | U | U | U |
| V73 | SCA | ? | U | U | U | M | U | U | U | U | U | U | M | U | U |
| V122 | SCA | II | M | U | M | U | U | U | U | U | U | U | M | U | U |
| V132 | SCA | I | U | U | M | M | M | U | M | U | U | U | M | U | U |
| V143 | SCA | I | U | U | U | M | M | U | U | U | U | U | U | U | U |
| V151 | SCA | III | U | U | M | U | U | U | M | U | U | U | M | U | U |
| V154 | SCA | III | M | U | U | U | U | U | U | U | U | U | U | U | U |
| V171 | SCA | I | U | U | M | M | U | M | U | U | U | U | U | U | U |
| V176 | SCA | III | U | U | U | M | U | U | U | U | U | U | U | U | U |
| V179 | SCA | III | U | U | U | M | U | U | U | U | U | U | U | U | U |
| V180 | SCA | I | U | U | U | M | U | U | U | U | U | U | U | U | U |
| V181 | SCA | I | U | U | U | M | U | M | U | U | M | U | U | U | U |
| V187 | SCA | III | M | U | U | U | U | U | U | U | U | U | U | U | U |
| V221 | SCA | I | M | U | M | U | U | U | U | U | U | U | U | U | U |
| V229 | SCA | I | U | U | U | U | M | U | U | U | U | U | U | U | U |
| V239 | SCA | III | U | U | U | U | U | U | U | U | U | U | U | U | U |
| V240 | SCA | III | U | U | U | U | U | U | U | U | U | U | U | U | U |
| V241 | SCA | III | U | U | U | U | U | U | U | U | U | U | U | U | M |
| V242 | SCA | III | M | U | U | U | U | U | U | U | U | U | U | U | U |
| V243 | SCA | III | U | U | U | U | U | U | U | U | U | U | M | U | U |
| V246 | SCA | I | GR | U | U | U | U | U | U | U | U | U | M | U | U |
| V249 | SCA | I | U | U | U | M | U | M | U | U | U | U | U | U | U |
| V249A | SCA | I | U | U | M | U | U | GR | M | M | U | U | U | U | U |
| V251 | SCA | III | M | U | U | M | M | U | U | U | U | U | M | U | U |

| sample | TK1 | HDGF | POLR3D | FANCG | TRIP13 | HPSE | ASK | gene | tuba | SBT |
|---|---|---|---|---|---|---|---|---|---|---|
| T1 | U | U | U | U | U | U | U | NDP | 3/8 (38%) | 12/36 (33%) |
| T2 | U | U | U | U | U | U | U | TM4SF11 | 0/8 | 1/36 (2%) |
| T3 | U | U | U | U | U | U | U | RUNX3 | 0/8 | 9/36 (25%) |
| T4 | M | U | M | U | U | U | U | TNFRSF10B | 1/8 (13%) | 16/36 (44%) |
| T5 | U | U | U | U | U | U | U | DEK | 1/8 (13%) | 2/36 (6%) |
| T6 | U | U | U | U | U | U | U | CGI-38 | 1/8 (13%) | 3/36 (8%) |
| T7 | U | U | U | U | U | U | U | HEC | 2/8 (25%) | 8/35 (23%) |
| T8 | U | U | M | U | M | U | M | MYBL2 | 4/8 (50%) | 7/36 (19%) |
| | | | | | | | | TTK | 0/8 | 0/36 |
| 529 | U | U | U | U | U | U | U | BARD1 | 1/8 (13%) | 2/36 (6%) |
| 530 | U | U | U | GR | U | U | U | ACTN1 | 1/8 (13%) | 8/36 (22%) |
| 531 | U | U | GR | U | U | U | U | C11ORF2 | 0/8 | 0/34 |
| 533 | U | U | U | U | U | U | U | SMPD2 | 2/8 (25%) | 2/35 (%) |
| 535C | U | U | U | U | U | U | U | TK1 | 1/8 (13%) | 3/36 (8%) |
| 536 | U | U | U | U | U | U | U | HDGF | 0/8 | 0/36 |
| 536A | U | U | U | U | U | U | U | POLR3D | 2/8 (25%) | 0/32 |
| 537A | M | U | U | U | U | U | U | FANCG | 0/8 | 0/31 |
| 537B | U | U | U | U | U | U | U | TRIP13 | 1/8 (13%) | 0/36 |
| 538 | U | U | U | U | U | GR | U | HPSE | 0/8 | 1/36 (3%) |
| 539A | U | U | U | U | U | U | U | ASK | 1/8 (13%) | 1/35 (3%) |
| 540 | U | U | U | U | U | U | U | | | |
| 541A | U | U | U | U | U | U | U | | | |

TABLE 6-continued (below) MSP Metascore

| | | | | | | | |
|---|---|---|---|---|---|---|---|
| 542 | U | U | GR | GR | U | U | U |
| 550C | U | U | U | U | U | U | U |
| 584 | U | U | U | U | U | U | U |
| 592A | U | U | U | GR | U | U | U |
| 594A | U | U | U | U | U | U | U |
| 596A | M | U | U | U | U | U | U |
| 597A | U | U | U | U | U | U | U |
| 598A | U | U | U | U | U | U | U |
| 599A | U | U | U | U | U | U | U |
| 600A | U | U | U | U | U | U | U |
| 601A | U | U | U | U | U | U | U |
| 602A | U | U | U | U | U | U | U |
| 615-1 | U | U | U | U | U | U | U |
| 615-2 | U | U | GR | U | U | M | U |
| V2 | U | U | U | U | U | U | U |
| V7 | U | U | U | GR | U | U | U |
| V11 | U | U | U | U | U | U | U |
| V61 | U | U | U | GR | U | U | U |
| V61A | U | U | U | U | U | U | U |
| V81 | U | U | U | U | U | U | U |
| V82 | U | U | U | U | U | U | U |
| V82A | U | U | GR | U | U | U | U |
| V110 | U | U | U | U | U | U | U |
| V150 | M | U | U | U | U | U | M |
| V195 | U | U | U | U | U | U | U |
| V220 | U | U | U | U | U | U | U |
| V244 | U | U | U | U | U | U | U |
| V245 | U | U | U | U | U | U | U |
| 544B | U | U | U | U | GR | U | U |
| 545A | GR | GR | GR | GR | GR | GR | GR |
| 546 | U | U | U | U | U | U | U |
| 547 | U | U | U | U | U | U | U |
| 548 | M | U | U | M | U | U | M |
| 549A | U | U | U | U | U | U | U |
| 549C | M | U | U | U | U | U | M |
| 551A | U | U | U | U | U | U | U |
| 551B | U | U | U | U | U | U | U |
| 552 | U | U | U | U | U | U | U |
| 553 | U | U | U | U | M | U | U |
| 554 | U | U | U | U | U | U | U |
| 555 | U | U | U | U | U | U | U |
| 556 | U | U | U | U | U | U | U |
| 557C | U | U | U | U | U | U | M |
| 558 | U | U | U | U | U | U | U |
| 559 | U | U | U | GR | U | U | U |
| 560 | U | M | U | U | U | U | U |
| 561A | U | U | U | U | U | U | U |
| 561B | U | M | U | U | U | U | U |
| 562 | U | U | U | U | U | U | U |
| 563 | U | U | U | U | U | U | U |
| 564B | U | U | U | U | U | U | U |
| 565 | U | U | U | U | U | U | U |
| 566 | U | U | U | U | U | U | U |
| 567 | U | U | U | U | U | U | U |
| 568A | U | U | U | U | U | U | U |
| 569 | U | U | U | U | U | U | U |
| 570A | U | U | U | U | U | U | U |
| 571A | U | U | U | U | U | U | U |
| 572A | U | U | U | U | U | U | U |
| 572B | U | U | U | U | U | U | U |
| 573 | U | U | U | U | U | U | U |
| 574 | U | U | U | U | U | U | U |
| 575 | U | U | U | U | U | U | U |
| 576 | M | U | U | U | U | U | U |
| 578 | U | U | U | U | U | U | U |
| 579 | U | U | U | U | U | U | U |
| 580 | U | U | U | U | U | U | U |
| 581 | U | U | U | U | U | U | U |
| 582 | U | U | U | U | U | U | U |
| 583 | U | U | U | U | U | U | U |
| 585 | U | U | U | U | U | U | U |
| 586 | U | GR | GR | GR | U | U | GR |
| 587 | M | U | U | U | U | U | U |
| 588 | GR | GR | GR | GR | U | GR | GR |
| 589 | U | U | U | U | U | U | U |
| 591 | U | U | U | U | U | U | U |
| 593 | U | U | U | U | U | U | M |

TABLE 6-continued (below) MSP Metascore

| | | | | | | | |
|---|---|---|---|---|---|---|---|
| 595 | M | U | U | U | U | U | U |
| V1 | U | U | U | M | M | U | U |
| V27 | U | U | U | U | U | U | U |
| V40 | U | U | U | U | U | U | U |
| V46 | U | U | U | U | U | U | U |
| V73 | U | U | U | U | U | U | U |
| V122 | U | U | U | U | U | U | M |
| V132 | U | U | U | M | U | U | M |
| V143 | U | U | U | U | U | U | M |
| V151 | U | U | U | M | U | U | U |
| V154 | U | U | U | U | U | U | U |
| V171 | U | U | U | U | U | U | U |
| V176 | U | U | U | U | U | U | M |
| V179 | U | U | U | U | U | U | U |
| V180 | U | U | U | U | U | U | U |
| V181 | U | U | U | M | U | U | U |
| V187 | U | U | U | U | U | U | U |
| V221 | U | U | U | U | U | U | U |
| V229 | U | U | U | U | U | U | U |
| V239 | U | U | U | U | U | U | U |
| V240 | U | U | U | U | U | U | U |
| V241 | U | U | M | U | U | U | U |
| V242 | U | U | U | U | U | U | U |
| V243 | U | U | U | U | U | U | U |
| V246 | U | U | U | U | U | U | U |
| V249 | U | U | U | U | U | U | U |
| V249A | U | U | U | U | U | U | U |
| V251 | U | U | U | U | U | U | U |

M = methylated;
U = unmethylated;
GR = no results

In ovarian cell lines the genes NDP, TM4SF11, RUNX3, TNFRSF10B, DEK, HEC, CGI-38, MYBL2 were found to be hypermethylated, whereas TTK, BARD1, ACTN1, C11ORF2, SMPD2, TK1, HDGF, POLR3D, FANCG, TRIP13, HPSE, ASK were non-methylated.

From the genes methylated in cell lines, TM4SF11 and RUNX3 were non-methylated in the Tubae test population, whereas TNFRSF10B, DEK, and CGI-38 were methylated only in one out of the eight (13%). NDP, HEC, MYBL2 were methylated in more than one out of the eight (>13%) specimen of the Tubae test population.

The genes TNFRSF10B, RUNX3, TM4SF11, ACTN1 and FANCG were found to be methylated in a higher degree in SBT and/or SCA when compared to their methylation status in Tubae.

Of the genes TTK, BARD1, ACTN1, C11ORF2, SMPD2, TK1, HDGF, POLR3D, FANCG, TRIP13, HPSE, ASK which were non-methylated in cell-lines, two genes SMPD2 and POLR3D appeared to be methylated in 2 out of the 8 Tubae specimen. TTK, C11ORF2, HDGF, FANCG and HPSE were unmethylated in all of the 8 Tubae. The remainder genes were methylated in 1 out of the 8 Tubae.

The genes ACTN1, HDGF, FANCG and HPSE were found to be methylated in a higher degree in SBT and/or SCA when compared to their methylation status in Tubae.

REFERENCES

The disclosure of each reference cited is expressly incorporated herein.

Reeves et al., U.S. Pat. No. 6,596,493
Sidransky, U.S. Pat. No. 6,025,127
Sidransky, U.S. Pat. No. 5,561,041
Nelson et al., U.S. Pat. No. 5,552,277
Herman, et al., U.S. Pat. No. 6,017,704
Baylin et al, U.S. Patent Application Publication No. 2003/0224040 A1
Belinsky et al., U.S. Patent Application Publication No. 2004/0038245 A1
Sidransky, U.S. Patent Application Publication No. 2003/0124600 A1
Sidransky, U.S. Patent Application Publication No. 2004/0081976 A1
Sukumar et al., U.S. Pat. No. 6,756,200 B2
Herman et al., U.S. Patent Application Publication No. 2002/0127572 A1

We claim:

1. A method for identifying an ovarian cell as neoplastic, comprising:
   detecting in a test ovarian cell epigenetic silencing of a gene encoding TM4SF11 transmembrane 4 superfamily member 11 (plasmolipin); and identifying the test ovarian cell as neoplastic when epigentic silencing of transmembrane 4 superfamily member 11 (plasmolipin) is detected.

2. The method of claim 1 further comprising detecting in the test ovarian cell epigenetic silencing of at least one gene encoding a protein selected from the group consisting of: TNFRSF10B tumor necrosis factor receptor superfamily (member 10b), RUNX3 runt-related transcription factor 3, ACTN1 actinin (alpha 1), and FANCG Fanconi anemia (complementation group G).

3. The method of claim 1 wherein methylation of a CpG dinucleotide motif in the gene is detected.

4. The method of claim 3 wherein methylation is detected by contacting at least a portion of the gene with a methylation-sensitive restriction endonuclease, said endonuclease preferentially cleaving methylated recognition sites relative to non-methylated recognition sites, whereby cleavage of the portion of the gene indicates methylation of the portion of the gene.

5. The method of claim 4 wherein the methylation-sensitive restriction endonuclease is selected from the group consisting of Acc III, Ban I, BstN I, Msp I, and Xma I.

6. The method of claim 5 wherein methylation is detected by contacting at least a portion of the gene with a methylation-sensitive restriction endonuclease, said endonuclease preferentially cleaving non-methylated recognition sites relative to methylated recognition sites, whereby cleavage of the portion of the gene indicates non-methylation of the portion of the gene provided that the gene comprises a recognition site for the methylation-sensitive restriction endonuclease.

7. The method of claim 6 wherein the methylation-sensitive restriction endonuclease is selected from the group consisting of Acc II, Ava I, BssH II, BstU I, Hpa II, and Not I.

8. The method of claim 3 wherein methylation is detected by:
contacting at least a portion of the gene of the test cell with bisulfite ions, which selectively modify a non-methylated cytosine residue relative to a methylated cytosine residue, or with hydrazine, which selectively modifies a methylated cytosine residue relative to a non-methylated cytosine residue; and
detecting a product generated due to said contacting.

9. The method of claim 8 wherein the step of detecting comprises amplification with at least one primer that hybridizes to a sequence comprising a modified non-methylated CpG dinucleotide motif but not to a sequence comprising an unmodified methylated CpG dinucleotide motif thereby forming amplification products.

10. The method of claim 8 wherein the step of detecting comprises amplification with at least one primer that hybridizes to a sequence comprising an unmodified methylated CpG dinucleotide motif but not to a sequence comprising a modified non-methylated CpG dinucleotide motif thereby forming amplification products.

11. The method of claim 9 wherein the amplification products are detected using (a) a first oligonucleotide probe which hybridizes to a sequence comprising a modified non-methylated CpG dinucleotide motif but not to a sequence comprising an unmodified methylated CpG dinucleotide motif, (b) a second oligonucleotide probe that hybridizes to a sequence comprising an unmodified methylated CpG dinucleotide motif but not to sequence comprising a modified non-methylated CpG dinucleotide motif, or (c) both said first and second oligonucleotide probes.

12. The method of claim 10 wherein the amplification products are detected using (a) a first oligonucleotide probe which hybridizes to a sequence comprising a modified non-methylated CpG dinucleotide motif but not to a sequence comprising an unmodified methylated CpG dinucleotide motif, (b) a second oligonucleotide probe that hybridizes to a sequence comprising an unmodified methylated CpG dinucleotide motif but not to sequence comprising a modified non-methylated CpG dinucleotide motif, or (c) both said first and second oligonucleotide probes.

13. The method of claim 8 wherein the product is detected by a method selected from the group consisting of electrophoresis, chromatography, and mass spectrometry.

14. The method of claim 8 wherein the at least a portion of the gene is contacted with hydrazine and the hydrazine-contacted at least a portion of the gene is cleaved with piperidine.

15. The method of claim 8 wherein the at least a portion of the gene is contacted with bisulfite ions and the bisulfite ions-contacted at least a portion of the gene is treated with alkali.

16. The method of claim 3 wherein methylation is detected by:
amplifying at least a portion of the gene, said portion comprising a CpG dinucleotide motif, to form amplification products;
contacting the amplification products with bisulfite ions, which selectively modify a non-methylated cytosine residue relative to a methylated cytosine residue, or with hydrazine, which selectively modifies a methylated cytosine residue relative to a non-methylated cytosine residue; and
detecting a product generated due to said contacting using (a) a first oligonucleotide probe which hybridizes to a sequence comprising a modified non-methylated CpG dinucleotide motif but not to a sequence comprising an unmodified methylated CpG dinucleotide motif, (b) a second oligonucleotide probe that hybridizes to a sequence comprising an unmodified methylated CpG dinucleotide motif but not to sequence comprising a modified non-methylated CpG dinucleotide motif, or (c) both said first and second oligonucleotide probes.

17. The method of claim 1 wherein the test ovarian cell is obtained from a surgical sample.

* * * * *

UNITED STATES PATENT AND TRADEMARK OFFICE
CERTIFICATE OF CORRECTION

PATENT NO.        : 7,507,536 B2
APPLICATION NO.   : 11/543986
DATED             : March 24, 2009
INVENTOR(S)       : Wim Van Criekinge et al.

It is certified that error appears in the above-identified patent and that said Letters Patent is hereby corrected as shown below:

In the Claims Section, Column 189, Claim 6, Line 6:
    Please replace "The method of claim 5 wherein" with --The method of claim 3 wherein--.

Signed and Sealed this

Twenty-ninth Day of September, 2009

David J. Kappos
*Director of the United States Patent and Trademark Office*